US011129621B2

United States Patent
Hamel et al.

(10) Patent No.: US 11,129,621 B2
(45) Date of Patent: Sep. 28, 2021

(54) DEVICES, SYSTEMS, AND METHODS FOR THE TREATMENT OF VASCULAR DEFECTS

(71) Applicant: Covidien LP, Mansfield, MA (US)

(72) Inventors: Gregory Hamel, Oakland, CA (US); Patrick Quinn, Stockton, CA (US); Arturo Rosqueta, San Jose, CA (US); Stephen Sosnowski, Sherrills Ford, NC (US); Christopher Andrews, Lake Elsinore, CA (US); Hieu Dang, Westminster, CA (US); Dinh Nguyen, Garden Grove, CA (US); Robert Pecor, Aliso Viejo, CA (US); Minh Q. Dinh, Fremont, CA (US); Ahramahzd Tatavoosian, Mission Viejo, CA (US)

(73) Assignee: Covidien LP, Mansfield, MA (US)

( * ) Notice: Subject to any disclaimer, the term of this patent is extended or adjusted under 35 U.S.C. 154(b) by 108 days.

(21) Appl. No.: 16/718,165

(22) Filed: Dec. 17, 2019

(65) Prior Publication Data

US 2020/0197017 A1 Jun. 25, 2020

Related U.S. Application Data

(60) Provisional application No. 62/780,540, filed on Dec. 17, 2018, provisional application No. 62/928,745,
(Continued)

(51) Int. Cl.
*A61B 17/12* (2006.01)
*A61B 17/00* (2006.01)

(52) U.S. Cl.
CPC .. *A61B 17/12113* (2013.01); *A61B 17/00234* (2013.01); *A61B 17/1214* (2013.01);
(Continued)

(58) Field of Classification Search
CPC ........ A61B 17/12113; A61B 17/00234; A61B 17/1214; A61B 17/12145;
(Continued)

(56) References Cited

U.S. PATENT DOCUMENTS

| 5,250,071 A | 10/1993 | Palermo |
| 5,312,415 A | 5/1994 | Palermo |

(Continued)

FOREIGN PATENT DOCUMENTS

| AU | 2002316320 B2 | 8/2008 |
| DE | 102011102933 A1 | 12/2012 |

(Continued)

OTHER PUBLICATIONS

Bhogal, Pervinder et al., Endovascular flow disruption: where are we now?, J. NeuroIntervent Surg., 2019, 11: 1024-1035.
(Continued)

*Primary Examiner* — Katrina M Stransky
*Assistant Examiner* — Paige A Codrington
(74) *Attorney, Agent, or Firm* — Fortem IP LLP; Mary L. Fox

(57) ABSTRACT

Devices, systems, and methods for treating vascular defects are disclosed herein. One aspect of the present technology, for example, includes an occlusive device comprising a mesh having a low-profile state for intravascular delivery to the aneurysm and a deployed state, the mesh comprising a first end portion, a second end portion, and a length extending between the first and second end portions, and a first lateral edge, a second lateral edge, and a width extending between the first and second lateral edges. The mesh may have a predetermined shape in the deployed state in which (a) the mesh is curved along its width, (b) the mesh is curved along its length, and (c) the mesh has an undulating contour across at least a portion of one or both of its length or its
(Continued)

width. The mesh is configured to be positioned within the aneurysm in the deployed state such that the mesh extends over the neck of the aneurysm.

20 Claims, 36 Drawing Sheets

Related U.S. Application Data filed on Oct. 31, 2019, provisional application No. 62/928,765, filed on Oct. 31, 2019.

(52) U.S. Cl.
CPC .. *A61B 17/12145* (2013.01); *A61B 17/12172* (2013.01); *A61B 17/12177* (2013.01); *A61B 2017/00867* (2013.01); *A61B 2017/1205* (2013.01)

(58) Field of Classification Search
CPC ........ A61B 17/12172; A61B 17/12177; A61B 17/12168; A61B 17/12022; A61B 17/12031; A61B 2017/00867; A61B 2017/1205; A61B 2017/12063
USPC ........................................................ 606/191
See application file for complete search history.

(56) References Cited

U.S. PATENT DOCUMENTS

| | | | |
|---|---|---|---|
| 5,350,397 A | 9/1994 | Palermo et al. | |
| 5,354,295 A * | 10/1994 | Guglielmi | A61B 17/12022 606/32 |
| 5,382,259 A | 1/1995 | Phelps et al. | |
| 5,645,558 A | 7/1997 | Horton | |
| 5,669,931 A | 9/1997 | Kupiecki et al. | |
| 5,725,552 A | 3/1998 | Kotula et al. | |
| 5,733,294 A | 3/1998 | Forber et al. | |
| 5,741,333 A | 4/1998 | Frid | |
| 5,749,891 A | 5/1998 | Ken et al. | |
| 5,749,919 A | 5/1998 | Blanc | |
| 5,814,062 A | 9/1998 | Sepetka et al. | |
| 5,911,731 A | 6/1999 | Pham et al. | |
| 5,916,235 A | 6/1999 | Guglielmi | |
| 5,925,060 A | 7/1999 | Forber | |
| 5,928,260 A | 7/1999 | Chin et al. | |
| 5,935,148 A | 8/1999 | Villar et al. | |
| 5,944,738 A | 8/1999 | Amplatz et al. | |
| 5,951,599 A | 9/1999 | McCrory | |
| 5,964,797 A | 10/1999 | Ho | |
| 5,976,169 A | 11/1999 | Imran | |
| 5,980,554 A | 11/1999 | Lenker et al. | |
| 6,022,374 A | 2/2000 | Imran | |
| 6,033,423 A | 3/2000 | Ken et al. | |
| 6,036,720 A | 3/2000 | Abrams et al. | |
| 6,059,812 A | 5/2000 | Clerc et al. | |
| 6,063,070 A | 5/2000 | Eder | |
| 6,063,104 A | 5/2000 | Villar et al. | |
| 6,086,577 A | 7/2000 | Ken et al. | |
| 6,090,125 A | 7/2000 | Horton | |
| 6,093,199 A | 7/2000 | Brown et al. | |
| 6,096,021 A | 8/2000 | Helm et al. | |
| 6,123,715 A | 9/2000 | Amplatz | |
| 6,139,564 A | 10/2000 | Teoh | |
| 6,152,144 A | 11/2000 | Lesh et al. | |
| 6,159,531 A | 12/2000 | Dang et al. | |
| 6,168,615 B1 | 1/2001 | Ken et al. | |
| 6,168,622 B1 | 1/2001 | Mazzocchi | |
| 6,309,367 B1 | 10/2001 | Boock | |
| 6,344,048 B1 | 2/2002 | Chin et al. | |
| 6,346,117 B1 | 2/2002 | Greenhalgh | |
| 6,350,270 B1 | 2/2002 | Roue | |
| 6,368,339 B1 | 4/2002 | Amplatz | |
| 6,371,980 B1 | 4/2002 | Rudakov et al. | |
| 6,375,668 B1 | 4/2002 | Gifford et al. | |
| 6,383,174 B1 | 5/2002 | Eder | |
| 6,391,037 B1 | 5/2002 | Greenhalgh | |
| 6,428,558 B1 | 8/2002 | Jones et al. | |
| 6,447,531 B1 | 9/2002 | Amplatz | |
| 6,451,050 B1 | 9/2002 | Rudakov et al. | |
| 6,454,780 B1 | 9/2002 | Wallace | |
| 6,494,884 B2 | 12/2002 | Gifford et al. | |
| 6,506,204 B2 | 1/2003 | Mazzocchi | |
| 6,511,468 B1 | 1/2003 | Cragg et al. | |
| 6,547,804 B2 | 4/2003 | Porter et al. | |
| 6,551,303 B1 | 4/2003 | Van et al. | |
| 6,579,303 B2 | 6/2003 | Amplatz | |
| 6,585,748 B1 | 7/2003 | Jeffree | |
| 6,589,256 B2 | 7/2003 | Forber | |
| 6,589,265 B1 | 7/2003 | Palmer et al. | |
| 6,599,308 B2 | 7/2003 | Amplatz | |
| 6,602,261 B2 | 8/2003 | Greene et al. | |
| 6,605,101 B1 | 8/2003 | Schaefer et al. | |
| 6,605,102 B1 | 8/2003 | Mazzocchi et al. | |
| 6,605,111 B2 | 8/2003 | Bose et al. | |
| 6,613,074 B1 * | 9/2003 | Mitelberg | A61B 17/12022 606/200 |
| 6,626,939 B1 | 9/2003 | Burnside et al. | |
| 6,635,068 B1 | 10/2003 | Dubrul et al. | |
| 6,652,556 B1 | 11/2003 | Vantassel et al. | |
| 6,666,882 B1 | 12/2003 | Bose et al. | |
| 6,669,721 B1 | 12/2003 | Bose et al. | |
| 6,682,546 B2 | 1/2004 | Amplatz | |
| 6,689,486 B2 | 2/2004 | Ho et al. | |
| 6,730,108 B2 | 5/2004 | Van et al. | |
| 6,746,468 B1 | 6/2004 | Sepetka et al. | |
| 6,746,890 B2 | 6/2004 | Gupta et al. | |
| 6,780,196 B2 | 8/2004 | Chin et al. | |
| 6,802,851 B2 | 10/2004 | Jones et al. | |
| 6,811,560 B2 | 11/2004 | Jones et al. | |
| 6,855,153 B2 | 2/2005 | Saadat | |
| 6,855,154 B2 | 2/2005 | Abdel-Gawwad | |
| 6,878,384 B2 | 4/2005 | Cruise et al. | |
| 6,905,503 B2 | 6/2005 | Gifford et al. | |
| 6,936,055 B1 | 8/2005 | Ken et al. | |
| 6,991,617 B2 | 1/2006 | Hektner et al. | |
| 6,994,092 B2 | 2/2006 | Van et al. | |
| 6,994,717 B2 | 2/2006 | Konya et al. | |
| 7,011,671 B2 | 3/2006 | Welch | |
| 7,029,487 B2 | 4/2006 | Greene et al. | |
| 7,083,632 B2 | 8/2006 | Avellanet et al. | |
| 7,128,073 B1 | 10/2006 | Van et al. | |
| 7,128,736 B1 | 10/2006 | Abrams et al. | |
| 7,169,177 B2 | 1/2007 | Obara | |
| 7,195,636 B2 | 3/2007 | Avellanet et al. | |
| 7,229,461 B2 | 6/2007 | Chin et al. | |
| 7,232,461 B2 | 6/2007 | Ramer | |
| 7,326,225 B2 | 2/2008 | Ferrera et al. | |
| 7,331,980 B2 * | 2/2008 | Dubrul | A61B 17/12022 606/213 |
| 7,419,503 B2 | 9/2008 | Pulnev et al. | |
| 7,465,316 B2 | 12/2008 | Kujawski | |
| 7,597,704 B2 | 10/2009 | Frazier et al. | |
| 7,601,160 B2 | 10/2009 | Richter | |
| 7,708,754 B2 | 5/2010 | Balgobin et al. | |
| RE42,625 E | 8/2011 | Guglielmi | |
| 8,043,326 B2 | 10/2011 | Hancock et al. | |
| 8,142,456 B2 | 3/2012 | Rosqueta et al. | |
| 8,211,160 B2 | 7/2012 | Garrison et al. | |
| 8,333,783 B2 | 12/2012 | Braun et al. | |
| 8,343,167 B2 | 1/2013 | Henson | |
| 8,361,104 B2 | 1/2013 | Jones et al. | |
| 8,361,138 B2 | 1/2013 | Adams | |
| 8,388,650 B2 * | 3/2013 | Gerberding | A61B 17/12172 606/213 |
| 8,425,541 B2 | 4/2013 | Masters et al. | |
| 8,470,013 B2 | 6/2013 | Duggal et al. | |
| 8,715,317 B1 | 5/2014 | Janardhan et al. | |
| 8,834,515 B2 | 9/2014 | Win et al. | |
| 8,864,790 B2 | 10/2014 | Strauss et al. | |
| 8,906,057 B2 | 12/2014 | Connor et al. | |
| 8,968,382 B2 * | 3/2015 | Riina | A61B 17/1214 623/1.11 |

(56) References Cited

U.S. PATENT DOCUMENTS

| | | |
|---|---|---|
| 8,974,512 B2 | 3/2015 | Aboytes et al. |
| 8,979,893 B2 * | 3/2015 | Gerberding ...... A61B 17/12118 606/213 |
| 8,998,947 B2 | 4/2015 | Aboytes et al. |
| 9,211,202 B2 | 12/2015 | Strother et al. |
| 9,259,229 B2 * | 2/2016 | Abrams ........... A61B 17/12113 |
| 9,277,924 B2 * | 3/2016 | Clarke ............. A61B 17/12022 |
| 9,339,275 B2 | 5/2016 | Trommeter et al. |
| 9,486,224 B2 | 11/2016 | Riina et al. |
| 9,687,245 B2 * | 6/2017 | Molaei ............. A61B 17/12113 |
| 9,833,309 B2 | 12/2017 | Levi et al. |
| 9,844,380 B2 | 12/2017 | Furey |
| 9,844,382 B2 | 12/2017 | Aboytes et al. |
| 9,855,051 B2 | 1/2018 | Aboytes et al. |
| 9,855,052 B2 | 1/2018 | Aboytes et al. |
| 9,907,684 B2 | 3/2018 | Connor et al. |
| 9,962,146 B2 | 5/2018 | Hebert et al. |
| 10,028,745 B2 | 7/2018 | Morsi |
| 10,716,573 B2 * | 7/2020 | Connor ............ A61B 17/12163 |
| 10,856,880 B1 * | 12/2020 | Badruddin ....... A61B 17/12177 |
| 2001/0000797 A1 | 5/2001 | Mazzocchi |
| 2001/0001835 A1 | 5/2001 | Greene et al. |
| 2002/0062145 A1 | 5/2002 | Rudakov et al. |
| 2002/0169473 A1 | 11/2002 | Sepetka et al. |
| 2002/0193812 A1 | 12/2002 | Patel et al. |
| 2002/0193813 A1 | 12/2002 | Helkowski et al. |
| 2002/0198561 A1 | 12/2002 | Amplatz |
| 2003/0004533 A1 | 1/2003 | Dieck et al. |
| 2003/0004568 A1 | 1/2003 | Ken et al. |
| 2003/0018294 A1 | 1/2003 | Cox |
| 2003/0028209 A1 | 2/2003 | Teoh et al. |
| 2003/0040772 A1 | 2/2003 | Hyodoh et al. |
| 2003/0055440 A1 | 3/2003 | Jones et al. |
| 2003/0093111 A1 | 5/2003 | Ken et al. |
| 2003/0113478 A1 | 6/2003 | Dang et al. |
| 2003/0114918 A1 | 6/2003 | Garrison et al. |
| 2004/0064093 A1 | 4/2004 | Hektner et al. |
| 2004/0115164 A1 | 6/2004 | Pierce et al. |
| 2004/0161451 A1 | 8/2004 | Pierce et al. |
| 2004/0172056 A1 | 9/2004 | Guterman et al. |
| 2005/0085836 A1 | 4/2005 | Raymond |
| 2005/0222580 A1 | 10/2005 | Gifford et al. |
| 2005/0228434 A1 | 10/2005 | Amplatz et al. |
| 2005/0267511 A1 | 12/2005 | Marks et al. |
| 2005/0277978 A1 | 12/2005 | Greenhalgh |
| 2006/0052816 A1 | 3/2006 | Bates et al. |
| 2006/0064151 A1 | 3/2006 | Guterman et al. |
| 2006/0089618 A1 | 4/2006 | McFerran et al. |
| 2006/0116709 A1 | 6/2006 | Sepetka et al. |
| 2006/0116712 A1 | 6/2006 | Sepetka et al. |
| 2006/0116713 A1 | 6/2006 | Sepetka et al. |
| 2006/0116714 A1 | 6/2006 | Sepetka et al. |
| 2006/0155323 A1 | 7/2006 | Porter et al. |
| 2006/0190025 A1 | 8/2006 | Lehe et al. |
| 2006/0190070 A1 | 8/2006 | Dieck et al. |
| 2006/0200234 A1 | 9/2006 | Hines |
| 2006/0206140 A1 | 9/2006 | Shaolian et al. |
| 2006/0206198 A1 | 9/2006 | Churchwell et al. |
| 2006/0206199 A1 | 9/2006 | Churchwell et al. |
| 2006/0241686 A1 | 10/2006 | Ferrera et al. |
| 2006/0247680 A1 | 11/2006 | Amplatz et al. |
| 2006/0271162 A1 | 11/2006 | Vito et al. |
| 2007/0010850 A1 | 1/2007 | Balgobin et al. |
| 2007/0083226 A1 | 4/2007 | Buiser et al. |
| 2007/0100426 A1 | 5/2007 | Rudakov et al. |
| 2007/0167876 A1 | 7/2007 | Euteneuer et al. |
| 2007/0167877 A1 | 7/2007 | Euteneuer et al. |
| 2007/0167972 A1 | 7/2007 | Euteneuer et al. |
| 2007/0175536 A1 | 8/2007 | Monetti et al. |
| 2007/0179520 A1 | 8/2007 | West |
| 2007/0185442 A1 | 8/2007 | Euteneuer et al. |
| 2007/0185443 A1 | 8/2007 | Euteneuer et al. |
| 2007/0185444 A1 | 8/2007 | Euteneuer et al. |
| 2007/0185457 A1 | 8/2007 | Euteneuer et al. |
| 2007/0191924 A1 | 8/2007 | Rudakov |
| 2007/0219619 A1 | 9/2007 | Dieck et al. |
| 2007/0276426 A1 | 11/2007 | Euteneuer |
| 2007/0276427 A1 | 11/2007 | Euteneuer |
| 2007/0282373 A1 | 12/2007 | Ashby et al. |
| 2007/0288083 A1 | 12/2007 | Hines |
| 2008/0082176 A1 | 4/2008 | Slazas |
| 2008/0097401 A1 | 4/2008 | Trapp et al. |
| 2008/0114391 A1 | 5/2008 | Dieck et al. |
| 2008/0114436 A1 | 5/2008 | Dieck et al. |
| 2008/0200945 A1 | 8/2008 | Amplatz et al. |
| 2008/0200979 A1 | 8/2008 | Dieck et al. |
| 2008/0221600 A1 | 9/2008 | Dieck et al. |
| 2008/0281350 A1 | 11/2008 | Sepetka et al. |
| 2009/0043375 A1 | 2/2009 | Rudakov et al. |
| 2009/0062841 A1 | 3/2009 | Amplatz et al. |
| 2009/0062899 A1 | 3/2009 | Dang et al. |
| 2009/0112251 A1 | 4/2009 | Qian et al. |
| 2009/0187214 A1 | 7/2009 | Amplatz et al. |
| 2009/0264978 A1 | 10/2009 | Dieck et al. |
| 2009/0275974 A1 | 11/2009 | Marchand et al. |
| 2009/0287291 A1 | 11/2009 | Becking et al. |
| 2009/0287292 A1 | 11/2009 | Becking et al. |
| 2009/0287294 A1 | 11/2009 | Rosqueta et al. |
| 2009/0318892 A1 | 12/2009 | Aboytes et al. |
| 2009/0318941 A1 | 12/2009 | Sepetka et al. |
| 2009/0319023 A1 | 12/2009 | Hildebrand et al. |
| 2010/0030200 A1 | 2/2010 | Strauss et al. |
| 2010/0036410 A1 | 2/2010 | Krolik et al. |
| 2010/0094335 A1 * | 4/2010 | Gerberding ............... A61F 2/06 606/213 |
| 2010/0121350 A1 | 5/2010 | Mirigian |
| 2010/0139465 A1 | 6/2010 | Christian et al. |
| 2010/0144895 A1 | 6/2010 | Porter |
| 2010/0174269 A1 | 7/2010 | Tompkins et al. |
| 2010/0185271 A1 | 7/2010 | Zhang |
| 2010/0256527 A1 | 10/2010 | Lippert et al. |
| 2010/0256528 A1 | 10/2010 | Lippert et al. |
| 2010/0256601 A1 | 10/2010 | Lippert et al. |
| 2010/0256602 A1 | 10/2010 | Lippert et al. |
| 2010/0256603 A1 | 10/2010 | Lippert et al. |
| 2010/0256604 A1 | 10/2010 | Lippert et al. |
| 2010/0256605 A1 | 10/2010 | Lippert et al. |
| 2010/0256606 A1 | 10/2010 | Lippert et al. |
| 2010/0262014 A1 | 10/2010 | Huang |
| 2010/0268201 A1 | 10/2010 | Tieu et al. |
| 2011/0022149 A1 | 1/2011 | Cox et al. |
| 2011/0046658 A1 | 2/2011 | Connor et al. |
| 2011/0077620 A1 | 3/2011 | Debeer |
| 2011/0137332 A1 | 6/2011 | Sepetka et al. |
| 2011/0137405 A1 | 6/2011 | Wilson et al. |
| 2011/0144669 A1 | 6/2011 | Becking et al. |
| 2011/0152993 A1 | 6/2011 | Marchand et al. |
| 2011/0202085 A1 | 8/2011 | Loganathan et al. |
| 2011/0208227 A1 | 8/2011 | Becking |
| 2011/0224776 A1 | 9/2011 | Sepetka et al. |
| 2011/0265943 A1 | 11/2011 | Rosqueta et al. |
| 2011/0319926 A1 | 12/2011 | Becking et al. |
| 2012/0022572 A1 | 1/2012 | Braun et al. |
| 2012/0041472 A1 | 2/2012 | Tan et al. |
| 2012/0101510 A1 | 4/2012 | Lenker et al. |
| 2012/0116350 A1 | 5/2012 | Strauss et al. |
| 2012/0165919 A1 | 6/2012 | Cox et al. |
| 2012/0197283 A1 | 8/2012 | Marchand et al. |
| 2012/0239074 A1 | 9/2012 | Aboytes et al. |
| 2012/0283768 A1 | 11/2012 | Cox et al. |
| 2012/0283769 A1 | 11/2012 | Cruise et al. |
| 2012/0316598 A1 | 12/2012 | Becking et al. |
| 2012/0316632 A1 | 12/2012 | Gao |
| 2012/0330341 A1 | 12/2012 | Becking et al. |
| 2012/0330347 A1 | 12/2012 | Becking et al. |
| 2012/0330348 A1 | 12/2012 | Strauss et al. |
| 2013/0066357 A1 | 3/2013 | Aboytes et al. |
| 2013/0066360 A1 | 3/2013 | Becking et al. |
| 2013/0085522 A1 | 4/2013 | Becking et al. |
| 2013/0090682 A1 * | 4/2013 | Bachman ......... A61B 17/12177 606/200 |
| 2013/0116722 A1 | 5/2013 | Aboytes et al. |
| 2013/0150879 A1 | 6/2013 | Li et al. |
| 2013/0178886 A1 | 7/2013 | Liu et al. |

(56) References Cited

U.S. PATENT DOCUMENTS

| | | |
|---|---|---|
| 2013/0274866 A1 | 10/2013 | Cox et al. |
| 2014/0012307 A1 | 1/2014 | Franano et al. |
| 2014/0058420 A1 | 2/2014 | Hannes et al. |
| 2014/0316012 A1 | 10/2014 | Freyman et al. |
| 2014/0371734 A1 | 12/2014 | Truckai |
| 2015/0080945 A1 | 3/2015 | Michalak |
| 2015/0216684 A1 | 8/2015 | Enzmann et al. |
| 2015/0250628 A1 | 9/2015 | Monstadt et al. |
| 2015/0257751 A1 | 9/2015 | Bachar et al. |
| 2015/0272590 A1* | 10/2015 | Aboytes .......... A61B 17/12172 606/200 |
| 2015/0313605 A1 | 11/2015 | Griffin |
| 2015/0313737 A1 | 11/2015 | Tippett et al. |
| 2015/0327843 A1 | 11/2015 | Garrison |
| 2015/0342613 A1 | 12/2015 | Aboytes et al. |
| 2016/0022445 A1 | 1/2016 | Ruvalcaba et al. |
| 2016/0066921 A1 | 3/2016 | Seifert et al. |
| 2016/0135984 A1 | 5/2016 | Rudakov et al. |
| 2016/0206320 A1 | 7/2016 | Connor |
| 2016/0206321 A1 | 7/2016 | Connor |
| 2016/0262766 A1 | 9/2016 | Aboytes et al. |
| 2016/0302924 A1 | 10/2016 | Boutillette et al. |
| 2017/0035430 A1 | 2/2017 | Sarge et al. |
| 2017/0035437 A1 | 2/2017 | Sarge et al. |
| 2017/0150971 A1 | 6/2017 | Hines |
| 2017/0156903 A1 | 6/2017 | Shobayashi |
| 2017/0189035 A1 | 7/2017 | Porter |
| 2017/0266023 A1 | 9/2017 | Thomas |
| 2017/0273691 A1 | 9/2017 | Riina et al. |
| 2017/0340333 A1* | 11/2017 | Badruddin ......... A61B 17/12113 |
| 2017/0367708 A1 | 12/2017 | Mayer et al. |
| 2018/0036012 A1* | 2/2018 | Aboytes .......... A61B 17/12172 |
| 2018/0049859 A1 | 2/2018 | Stoppenhagen et al. |
| 2018/0125686 A1 | 5/2018 | Lu |
| 2018/0140305 A1 | 5/2018 | Connor |
| 2018/0161185 A1 | 6/2018 | Kresslein et al. |
| 2018/0177580 A9 | 6/2018 | Shemesh et al. |
| 2018/0193025 A1 | 7/2018 | Walzman |
| 2018/0193026 A1* | 7/2018 | Yang ...................... A61F 2/90 |
| 2018/0206852 A1 | 7/2018 | Moeller |
| 2018/0303489 A1* | 10/2018 | Walzman ......... A61B 17/12036 |
| 2019/0008522 A1* | 1/2019 | Lorenzo ........... A61B 17/12172 |
| 2019/0053811 A1* | 2/2019 | Garza ............. A61B 17/12154 |
| 2019/0059907 A1 | 2/2019 | Rosqueta et al. |
| 2019/0192167 A1* | 6/2019 | Lorenzo ........... A61B 17/12113 |
| 2019/0201592 A1 | 7/2019 | Takahashi et al. |
| 2019/0209178 A1 | 7/2019 | Richter et al. |
| 2019/0357914 A1* | 11/2019 | Gorochow ....... A61B 17/12145 |
| 2019/0365385 A1* | 12/2019 | Gorochow ....... A61B 17/12168 |
| 2020/0187953 A1 | 6/2020 | Hamel et al. |
| 2020/0187954 A1 | 6/2020 | Hamel et al. |
| 2020/0197018 A1 | 6/2020 | Hamel et al. |
| 2020/0197020 A1 | 6/2020 | Hamel et al. |

FOREIGN PATENT DOCUMENTS

| | | |
|---|---|---|
| WO | 02054980 A2 | 7/2002 |
| WO | 2007054116 A1 | 5/2007 |
| WO | 2010027363 A1 | 3/2010 |
| WO | 2011066962 A1 | 6/2011 |

OTHER PUBLICATIONS

Jia, Zhen Yu et al., Development of New Endovascular Devices for Aneurysm Treatment, Journal of Stroke, 2018, 20(1): 46-56.

Pierot, Laurent et al., Safety and efficacy of aneurysm treatment with WEB in the cumulative population of three prospective, multicenter series, J. NeuroIntervent Surg., 2018, 10: 556-562.

Bor et al., Long-term, serial screening for intracranial aneurysms in individuals with a family history of aneurysmal subarachnoid haemorrhage: a cohort study. Lancet Neurol 2014;13:385-392.

Brown et al., Unruptured intracranial aneurysms: epidemiology, natural history, management options, and familial screening. Lancet Neurol 2014;13:393-404.

Guglielmi et al., Endovascular treatment of posterior circulation aneurysms by electrothrombosis using electrically detachable coils. J Neurosurg 1992;77:515-524.

Molyneux et al., Int subarachnoid aneurysm trial of neurosurgical clipping versus endovascular coiling in 2143 patients with ruptured intracranial aneurysms: a randomised comparison of effects on survival, dependency, seizures . . . Lancet 2005;366:809-817.

Molyneux et al., International Subarachnoid Aneurysm Trial (ISAT) of neurosurgical clipping versus endovascular coiling in 2143 patients with ruptured intracranial aneurysms: a randomised trial. Lancet 2002;360:1267-1274.

Wiebers et al., Unruptured intracranial aneurysms: natural history, clinical outcome, and risks of surgical and endovascular treatment. Lancet 2003;362:103-110.

Dmytriw, Adam A. et al., Endosaccular Flow Disruption: A New Frontier in Endovascular Aneurysm Management, NeuroSurgery, vol. 0, No. 0, 2019, 12 pages.

International Search Report and Written Opinion dated Jun. 25, 2020; International Application No. PCT/US2019/067000; 16 pages.

International Search Report and Written Opinion dated Jun. 25, 2020; International Application No. PCT/US2019/067002; 15 pages.

* cited by examiner

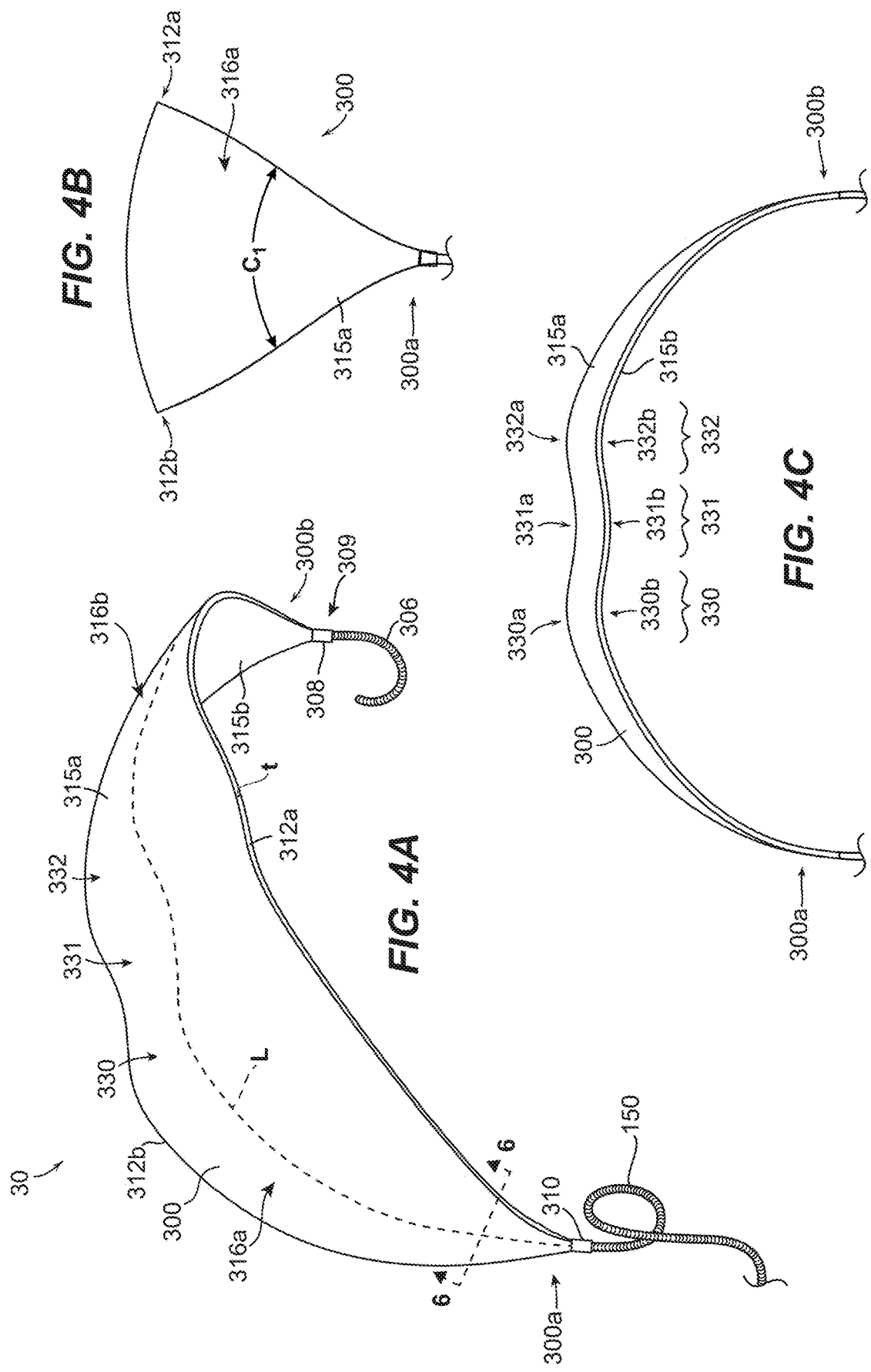

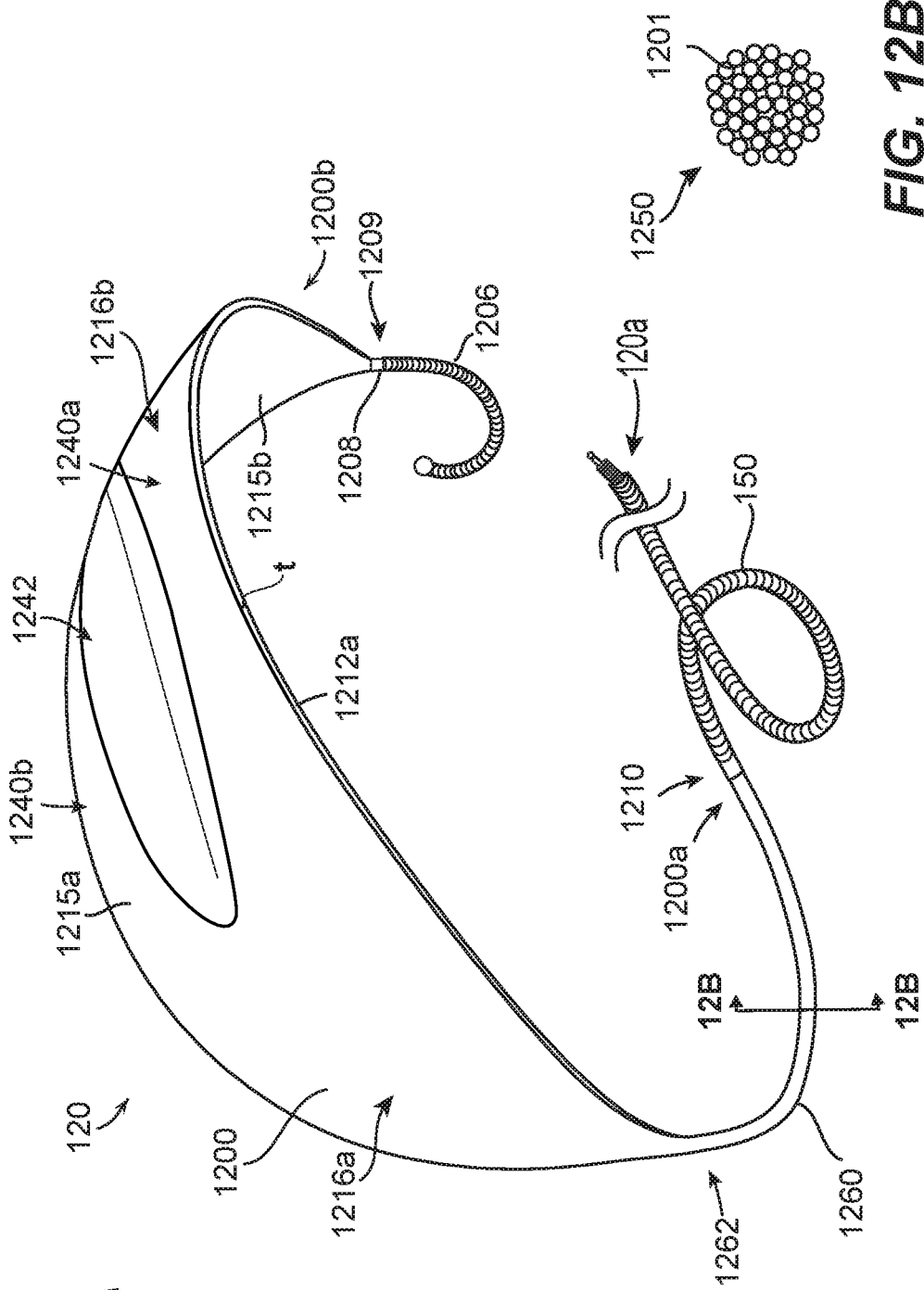

DEVICES, SYSTEMS, AND METHODS FOR THE TREATMENT OF VASCULAR DEFECTS

CROSS-REFERENCE TO RELATED APPLICATION(S)

The present application claims the benefit of priority to U.S. Provisional Application No. 62/780,540, filed Dec. 17, 2018, U.S. Provisional Application No. 62/928,745, filed Oct. 31, 2019, and U.S. Provisional Application No. 62/928,765, filed Oct. 31, 2019, all of which are incorporated by reference herein in their entireties.

TECHNICAL FIELD

The present technology is directed generally to devices, systems, and methods for the treatment of vascular defects.

BACKGROUND

Intracranial saccular aneurysms occur in 1% to 2% of the general population and account for approximately 80% to 85% of non-traumatic subarachnoid hemorrhages.[1] Recent studies show a case fatality rate of 8.3% to 66.7% in patients with subarachnoid hemorrhage.[2] Endovascular treatment of intracranial aneurysms emerged in the 1990s with the advent of the Guglielmi detachable coil system (Boston Scientific, Natick, Mass.), which includes packing the aneurysm sac with metal coils to reduce or disrupt the flow of blood into the aneurysm, thereby enabling a local thrombus or clot to form which fills and ultimately closes off the aneurysm. The use of coil embolization to treat aneurysms substantially increased after the publication of favorable clinical data,[4][5][6] including evidence that disability or death at the 1-year follow-up occurred in 30.9% of patients treated surgically but only 23.5% in patients treated with coil embolization.[4] Similarly, these trials showed the overall morbidity and mortality at 1 year was 12.6% for surgical clipping and 9.8% for endovascular coiling (amongst patients with no prior history of subarachnoid hemorrhage).[6]

Although coiling has proven to have better outcomes than surgical clipping for both ruptured and unruptured aneurysms, treating complex aneurysms using conventional coiling is challenging. This is especially true for wide-necked aneurysms. Coil segments may protrude from the aneurysm sac through the neck of the aneurysm and into the parent vessel, causing serious complications for the patient. To address this, some treatments include temporarily positioning a balloon within the parent vessel across the neck of the aneurysm to prevent the coils from migrating across the neck during delivery. Alternatively, some treatments include permanently positioning a neck-bridging stent within the parent vessel across the neck of the aneurysm to prevent the coils from migrating across the neck during delivery. While balloon-assisted or stent-assisted coiling for wide-neck aneurysms has shown better occlusion rates and lower recurrence than coiling alone, the recanalization rate of treated large/giant aneurysms can be as high as 18.2%. Moreover, the addition of a balloon or stent and its associated delivery system to the procedure increases the time, cost, and complexity of treatment. Deployment of the stent or balloon during the procedure also greatly increases the risk of an intraprocedural clot forming, and can damage the endothelial lining of the vessel wall. Permanently positioning a stent within the parent vessel increases the chronic risk of clot formation on the stent itself and associated ischemic complications, and thus necessitates the use of dual antiplatelet therapy ("DAPT"). DAPT, in turn, increases the risk and severity of hemorrhagic complications in patients with acutely ruptured aneurysms or other hemorrhagic risks. Thus, neck-bridging stents are not indicated for the treatment of ruptured aneurysms.

The above-noted drawbacks associated with balloon- and stent-assisted coiling techniques influenced the development of intraluminal flow diverting stents, or stent-like structures implanted in the parent vessel across the neck of the aneurysm that redirect blood flow away from the aneurysm, thereby promoting aneurysm thrombosis. Flow diverters have been successfully used for treating wide-neck, giant, fusiform, and blister-like aneurysms. However, because they are positioned in the parent vessel, flow diverters require DAPT to avoid clot formation on the stent itself and ischemic complications. This, in turn, increases the risk and severity of hemorrhagic complications in patients with acutely ruptured aneurysms or other hemorrhagic risks. Thus, flow diverters are not indicated for the treatment of ruptured aneurysms. Flow diverters have also shown limited efficacy in treating bifurcation aneurysms (35-50%).

Endosaccular flow disrupting devices have been gaining momentum over the last decade, generally driven by their potential to provide the intra-aneurysmal flow disruption of coiling with the definitive remodeling at the aneurysm-parent vessel interface achieved by intraluminal flow diverters. Currently existing endosaccular devices are typically mesh devices configured to be deployed completely within the aneurysm sac, with the interstices of the mesh covering the aneurysm neck and reconstructing the aneurysm-parent vessel interface. The implant disrupts the blood flow entering and exiting the aneurysm sac (resulting in stasis and thrombosis) and supports neoendothelial overgrowth without requiring DAPT (unlike endoluminal flow diverters). Thus, endosaccular devices can be used to treat wide-necked aneurysms and ruptured aneurysms. Moreover, because the device is placed completely within the aneurysm sac, the parent and branch vessels are unimpeded and can be accessed for any further retreatment or subsequent deployment of adjunctive devices during treatment.

One existing endosaccular flow disrupting device is the Woven EndoBridge (WEB®; Microvention, Aliso Viejo, Calif.). The WEB device is designed to be placed completely within the aneurysm sac and span the neck where it disrupts local flow. The device is a generally globular, radially symmetrical braid joined at its proximal, centrally located pole to a detachment zone of a delivery wire and is intended to be used as a stand-alone therapy. While the WEB device has had some success in treating classic wide-necked bifurcation aneurysms, its ability to treat a wide range of aneurysm locations, shapes and sizes remains limited. For example, because of its bulky and stiff delivery profile the WEB device is difficult to maneuver around tight turns and thus cannot adequately access the aneurysm sac to treat sidewall aneurysms. Similarly, the larger constrained size of the WEB device requires delivery through a microcatheter having a diameter of at least 0.021 inches, and thus the WEB device cannot access and treat aneurysms at the smaller, more distal intracranial vessels. In addition, because of its globular shape, the WEB device also cannot treat irregularly-shaped aneurysms and is limited to the much-less-common "berry" shaped aneurysms.

Another current endosaccular flow disrupting technology is the Contour Neurovascular System™ (Cerus Endovascular, Fremont, Calif.). The Contour device is constructed from a dual-layer radiopaque shape-memory mesh having a flat, disc-like shape in its fully unconstrained configuration joined at its proximal, centrally located pole to a detachment zone of a delivery wire and is intended to be used as a stand-alone therapy. After deployment, the device assumes a tulip-like configuration conforming to the wall of the lower hemisphere of the aneurysm and across the neck opening. The device is intentionally oversized to the neck and largest measured equatorial diameter of the aneurysm. It can be reloaded and deployed a number of times, permitting an operator to reposition across the neck of the aneurysm. The Contour device is designed to sit across the neck with the marker position below the neck in the parent artery. While the Contour device's construction (joined at its proximal, centrally located pole to the detachment zone of a delivery wire) lends itself to treating bifurcation aneurysms (where the neck is generally normal to/axially aligned with the parent vessel through which the device approaches the aneurysm), its construction does not lend itself to treating side wall aneurysms (where the aneurysm neck is generally parallel to/radially adjacent the parent vessel through which the device approaches the aneurysm). If deployed into a sidewall aneurysm, the delivery catheter will have to approach the aneurysm sac from a shallow angle. Rather than assuming a tulip-like configuration conforming to the wall of the lower hemisphere of the aneurysm and across the neck opening, as when deployed into a bifurcation aneurysm, the device will expand on an angle such that at least the distal edge of the disk will traverse the neck and extend into the parent vessel. This leaves the aneurysm inadequately treated and increases the risk of ischemic complications related to clot formation on the portion of the disk extending into the parent vessel.

The NeQstent™ Aneurysm Bridging Device (Cerus Endovascular, Fremont, Calif.) derives from the Contour device, also having a flat, disc-like shape in its fully unconstrained configuration that is joined at its proximal, centrally located pole to a detachment zone of a delivery wire. In contrast to the Contour device, the NeQstent is intended to be used in conjunction with a separate coiling microcatheter and embolization coils. As such, the NeQstent has approximately 30 to 40% of the number of wires in its double layer mesh construction compared to Contour. This is mainly to allow access through the mesh or between the mesh and aneurysm wall by a coiling microcatheter. Proceeding through or around the mesh is largely dictated by the size and shape of aneurysm and the corresponding device selected. Accordingly, the more the device is oversized to the aneurysm, the more the mesh at the neck of the device is constrained. Once the device and coiling microcatheter are positioned in a preferred position, embolization coils are delivered into the aneurysm until a desired fill is achieved. The microcatheter is then removed and the device is detached from its delivery wire. Like the Contour device, the NeQstent's construction (joined at its proximal, centrally located pole to the detachment zone of a delivery wire) lends itself to treating bifurcation aneurysms but not side wall aneurysms. If deployed into such an aneurysm, rather than assuming a tulip-like configuration conforming to the wall of the lower hemisphere of the aneurysm and across the neck opening, as when deployed into a bifurcation aneurysm, some portion of the disk will traverse the neck and extend into the parent vessel. This leaves the aneurysm neck inadequately protected and increases the risk of ischemic complications related to coil prolapse into the parent vessel or clot formation on the portion of the disk extending into the parent vessel.

Thus, there is a need for improved devices, systems, and methods for treating intracranial aneurysms

SUMMARY

The present technology is directed generally to devices, systems, and methods for the treatment of vascular defects, and in particular, to endosaccular occlusive devices for treating ruptured and un-ruptured intracranial wide-neck, bifurcation, and sidewall aneurysms. The occlusive device may comprise a self-expanding mesh structure coupled to an embolic coil. The occlusive device has a low-profile state for intravascular delivery to an aneurysm and a deployed state in which the device is configured to be positioned within the interior cavity of the aneurysm. According to some aspects of the technology, the occlusive device is configured to be advanced through a microcatheter as small as a 0.017-inch microcatheter. When the device is implanted, the mesh is configured to be positioned over at least a portion of the neck of the aneurysm while the coil fills space within the aneurysm cavity and stabilizes and/or anchors the mesh at the neck. Positioned across at least a portion of the neck, the mesh reduces blood flow entering the sac of the aneurysm, prevents herniation of the coil(s) through the neck and into the parent vessel, and provides a scaffolding that promotes endothelialization across the covered portion of the neck, thus further reducing inflow. As a result, the occlusive devices of the present technology provide the clinical benefits of intrasaccular coil embolization in wide neck aneurysms that are ruptured and unruptured, located at bifurcations or side walls, and are regularly or irregularly shaped, thus avoiding the attendant disadvantages plaguing conventional endovascular aneurysm treatment devices, such as the inability to treat wide neck aneurysms and requiring the patient to take DAPT, respectively.

As detailed herein, the occlusive devices enable efficacious coil embolization of wide neck side wall and bifurcation aneurysms (i.e., having a neck diameter greater than 4 mm or a dome-to-neck ratio less than or equal to 2) without the use of adjunctive intralumenal implants and without DAPT. Especially as compared to conventional balloon- and stent-assisted coiling methods, the devices and systems of the present technology advantageously require fewer catheters for deployment and can be deployed through smaller microcatheters (e.g., a 0.017 inch microcatheter), thereby enabling treatment of sidewall aneurysms and the ability to access the smaller, more distal intracranial vessels. Unlike existing endosaccular occlusive devices with fixed shapes (such as WEB®), the occlusive devices of the present technology—can treat a variety of complex aneurysm morphologies. The occlusive devices and methods of the present technology also reduce the risk of intraprocedural and post procedural clot formation, reduce or altogether avoid intraprocedural endothelial disruption, enable a greater coil packing density (and thus a lower incidence of aneurysm recanalization), and reduce the likelihood of coil prolapse into the parent vessel.

The subject technology is illustrated, for example, according to various aspects described below. Various examples of aspects of the subject technology are described as numbered clauses (1, 2, 3, etc.) for convenience. These are provided as examples and do not limit the subject technology. It is noted that any of the dependent clauses may be combined in any combination, and placed into a respective independent clause, e.g., clauses 1, 11, 30, etc. The other clauses can be presented in a similar manner.

Clause 1. An occlusive device for treating an aneurysm, wherein a neck of the aneurysm opens to a blood vessel, the device comprising:
- a mesh formed of a tubular braid that has been flattened along its longitudinal axis such that opposing portions of the sidewall of the braid are pressed towards one another, wherein the mesh comprises:
  - a proximal end and a distal end, and
  - a low-profile state for intravascular delivery to the aneurysm and a deployed state in which the mesh has a predetermined, three-dimensional shape that is concave and circumscribes a portion of a sphere, wherein the mesh curves about the circumscribed sphere of from about 200 degrees to about 300 degrees;
  - a flexible, atraumatic lead-in member coupled to and extending distally from the distal end of the mesh;
- a coil coupled to and extending proximally from the proximal end of the mesh, wherein a length of the coil along a longitudinal axis of the device is greater than a length of the mesh along the longitudinal axis of the device;
- wherein the coil and the mesh are connected end-to-end such that, when positioned within a catheter for delivery, the mesh is positioned distal of the coil such that the mesh deploys first and is configured to extend across and cover the neck of the aneurysm, thereby substantially covering the neck and reducing blood flow through the neck from the blood vessel.

Clause 2. The device of Clause 1, wherein the mesh is self-expanding.

Clause 3. The device of Clause 1 or Clause 2, wherein the mesh has a constant radius of curvature.

Clause 4. The device of any one of Clauses 1 to 3, wherein the coil has a tertiary structure.

Clause 5. The device of any one of Clauses 1 to 4, wherein the coil is radiopaque.

Clause 6. The device of any one of Clauses 1 to 5, wherein coil is a platinum coil.

Clause 7. The device of any one of Clauses 1 to 6, wherein the mesh is formed of a plurality of filaments, and wherein at least some of the filaments are drawn-filled tube ("DFT") wires.

Clause 8. The device of any one of Clauses 1 to 7, wherein a proximal end of the mesh is configured to be detachably coupled to an elongated delivery member.

Clause 9. The device of any one of Clauses 1 to 8, wherein, in the deployed state, the mesh has a width that tapers at its proximal and distal ends, and wherein a width of the mesh is generally constant therebetween.

Clause 10. The device of any one of Clauses 1 to 9, wherein the lead-in member is a coil.

Clause 11. An occlusive device for treating an aneurysm, wherein a neck of the aneurysm opens to a blood vessel, the device comprising:
- a mesh formed of a tubular braid that has been flattened along its longitudinal axis such that opposing portions of the sidewall of the braid are pressed towards one another, the mesh comprising:
  - a proximal end and a distal end, and
  - a low-profile state for intravascular delivery to the aneurysm and a deployed state in which the mesh has a predetermined, three-dimensional shape that is concave and circumscribes a portion of a sphere, wherein the mesh curves about the circumscribed sphere of from about 200 degrees to about 300 degrees;
  - a flexible, atraumatic lead-in member coupled to and extending distally from the distal end of the mesh;
- a coil coupled to and extending proximally from the proximal end of the mesh, wherein a length of the coil along a longitudinal axis of the device is greater than a length of the mesh along the longitudinal axis of the device;
- wherein the coil and the mesh are connected end-to-end at a joint such that, when positioned within a catheter for delivery, the mesh is positioned distal of the coil such that the mesh deploys first,
- wherein a distal end of the coil is spaced apart from a proximal end of the mesh at the joint, and wherein a tubular member extends between the proximal end of the mesh and the distal end of the coil, the tubular member having a distal portion surrounded by the proximal end of the mesh and a proximal portion surrounded by the distal end of the coil.

Clause 12. The device of Clause 11, wherein the mesh is self-expanding.

Clause 13. The device of Clause 11 or Clause 12, wherein the mesh has a constant radius of curvature.

Clause 14. The device of any one of Clauses 11 to 13, wherein the coil has a tertiary structure.

Clause 15. The device of any one of Clauses 11 to 14, wherein the coil is radiopaque.

Clause 16. The device of any one of Clauses 11 to 15, wherein coil is a platinum coil.

Clause 17. The device of any one of Clauses 11 to 16, wherein the mesh is formed of a plurality of filaments, and wherein at least some of the filaments are drawn-filled tube ("DFT") wires.

Clause 18. The device of any one of Clauses 11 to 17, wherein a proximal end of the mesh is configured to be detachably coupled to an elongated delivery member.

Clause 19. The device of any one of Clauses 11 to 18, wherein, in a deployed state, the mesh has a width that tapers at its proximal and distal ends, and wherein a width of the mesh is generally constant therebetween.

Clause 20. The device of any one of Clauses 11 to 19, wherein the lead-in member is a coil.

Clause 21. The device of any one of Clauses 11 to 20, wherein the coil is a first coil, and wherein the tubular member is a second coil.

Clause 22. The device of Clause 21, wherein a diameter of the first coil is greater than a diameter of the second coil.

Clause 23. The device of Clause 22, further comprising a third coil positioned at the proximal end of the first coil, wherein a distal portion of the third coil is surrounded by a proximal portion of the first coil.

Clause 24. The device of any one of Clauses 11 to 23, wherein the coil assumes a pre-set three-dimensional shape in a deployed state.

Clause 25. The device of any one of Clauses 11 to 24, further comprising a mesh connector extending proximally from the proximal end of the mesh into a distal end of the tubular member.

Clause 26. The device of any one of Clauses 11 to 25, further comprising a coil connector extending the length of the coil and extending distally into a proximal end of the tubular member.

Clause 27. The device of any one of Clauses 11 to 26, further comprising (a) a mesh connector extending proximally from the proximal end of the mesh into a distal end of the tubular member, and (b) a coil connector extending the length of the coil and extending distally into a proximal end of the tubular member, wherein a distal portion of the coil connector is coupled to a proximal end of the mesh connector at a coupling region that is surrounded by the tubular member.

Clause 28. The device of Clause 27, wherein the coupling region is axially aligned with a distal portion of the coil.

Clause 29. The device of Clause 27, wherein the coupling region is axially aligned with a proximal portion of the mesh.

Clause 30. An occlusive device for treating an aneurysm, wherein a neck of the aneurysm opens to a blood vessel, the device comprising:
- a mesh having a low-profile state for intravascular delivery to the aneurysm and a deployed state, the mesh comprising—
  - a first end portion, a second end portion, and a length extending between the first and second end portions, and
  - a first lateral edge, a second lateral edge, and a width extending between the first and second lateral edges,
  - wherein the mesh has a predetermined shape in an expanded, unconstrained state in which (a) the mesh is curved along its width, (b) the mesh is curved along its length, and (c) the mesh has an undulating contour across at least a portion of one or both of its length or its width, and
  - wherein the mesh is configured to be positioned within the aneurysm in a deployed state such that the mesh extends over the neck of the aneurysm.

Clause 31. The occlusive device of Clause 30, wherein the mesh has a first side, a second side opposite the first side, and a thickness measured therebetween, and wherein the mesh has a generally constant thickness along its length.

Clause 32. The occlusive device of Clause 30 or Clause 31, wherein the mesh does not define an inner cavity.

Clause 33. The occlusive device of any one of Clauses 30 to 32, wherein the mesh is formed of a tubular braid that has been flattened along it longitudinal axis such that opposing portions of a sidewall of the tubular braid are urged towards one another.

Clause 34. The occlusive device of any one of Clauses 30 to Clause 33, wherein, at least in the expanded, unconstrained state, the mesh comprises a curved member having a plurality of undulations.

Clause 35. The occlusive device of Clause 34, wherein each of the undulations extend across at least a portion of the width of the mesh.

Clause 36. The occlusive device of Clause 34 or Clause 35, wherein the mesh has a first side and a second side opposite the first side, and wherein the plurality of undulations comprise a first inflection region comprising a first peak at the first side and a first valley at the second side, a second inflection region comprising a second valley at the first side and a second peak at the second side, and a third inflection region comprising a third peak at the first side and a third valley at the second side, and wherein the mesh is configured to be positioned within an aneurysm such that the first side faces the aneurysm cavity and the second side faces the parent vessel.

Clause 37. The occlusive device of any one of Clauses 34 to 36, wherein the mesh is configured to be positioned within the aneurysm such that the protrusion is convex towards the aneurysm cavity.

Clause 38. The occlusive device of any one of Clauses 30 to 37, wherein the mesh comprises a divot extending across at least a portion of the length of the mesh.

Clause 39. The occlusive device of Clause 38, wherein the divot corresponds to a protrusion along the length of the mesh, and wherein the occlusive device is configured to be positioned within the aneurysm such that the protrusion is convex towards the aneurysm cavity.

Clause 40. The occlusive device of any one of the preceding Clauses, wherein the width of the mesh tapers in the direction of the first end portion.

Clause 41. The occlusive device of any one of the preceding Clauses, wherein the width of the mesh tapers in the direction of the second end portion.

Clause 42. The occlusive device of any one of the preceding Clauses, wherein the mesh is formed of a plurality of filaments, and wherein at least some of the filaments are drawn-filled tube ("DFT") wires.

Clause 43. The occlusive device of any one of the preceding Clauses, wherein a proximal end of the mesh is configured to be detachably coupled to an elongated delivery member.

Clause 44. The occlusive device of any one of the preceding Clauses, wherein a proximal end of the occlusive device is configured to be detachably coupled to an elongated delivery member.

Clause 45. The occlusive device of any one of the preceding Clauses, further comprising an embolic element coupled to a proximal end of the mesh.

Clause 46. The occlusive device of any one of the preceding Clauses, further comprising a lead-in member coupled to a distal end of the mesh.

Clause 47. The occlusive device of any one of the preceding Clauses, wherein a radius of curvature of the mesh increases distally along its longitudinal axis between its proximal and distal ends.

Clause 48. The occlusive device of any one of the preceding Clauses, wherein a radius of curvature of the mesh decreases distally along its longitudinal axis between its proximal and distal ends.

Clause 49. An occlusive device for treating an aneurysm, wherein a neck of the aneurysm opens to a blood vessel, the device comprising:
- a mesh having a low-profile state for intravascular delivery to the aneurysm and a deployed state, the mesh comprising—
  - a first end portion, a second end portion, and a length extending between the first and second end portions, and
  - a first lateral edge, a second lateral edge, and a width extending between the first and second lateral edges; and
- a coil;
- wherein the mesh has a predetermined shape in an expanded, unconstrained state in which (a) the mesh is curved along its width, (b) the mesh is curved along its length, and (c) the mesh has an undulating contour across at least a portion of one or both of its length or its width;
- wherein the occlusive device is configured to be positioned within the aneurysm such that the mesh extends over the neck of the aneurysm and the coil is positioned between the dome of the aneurysm and the mesh.

Clause 50. The occlusive device of Clause 49, wherein the mesh and the coil are coupled end-to-end.

Clause 51. The occlusive device of Clause 49, wherein the mesh and the coil are coupled end-to-end and, when positioned within a delivery catheter for intravascular delivery to the aneurysm, the mesh is distal of the coil such that the mesh is delivered to the aneurysm before the coil.

Clause 52. A method for treating an aneurysm, wherein a neck of the aneurysm opens to a blood vessel, the method comprising:

positioning the occlusive device of any one of Clause 30 to Clause 51 within the aneurysm such that a portion of the mesh is disposed across the neck of the aneurysm.

Clause 53. The method of Clause 52, further comprising urging the first and second end portions away from the neck of the aneurysm in response to the portion of the mesh over the neck of the aneurysm being urged towards the parent vessel.

Clause 54. The method of Clause 52 or Clause 53, further comprising urging the first and second end portions Clause 55. The method of any one of the previous Clauses, wherein the mesh comprises an inflection region that is concave towards the parent vessel and has a radius of curvature, and wherein the method further comprises reducing the curvature of the inflection region in response to the portion of the mesh over the neck of the aneurysm being urged towards the parent vessel.

Clause 56. The method of any one of the previous Clauses, wherein the inflection region extends longitudinally along the occlusive device.

Clause 57. The method of any one of the previous Clauses, wherein the inflection region extends laterally across the occlusive device.

Clause 58. The method of any one of the previous Clauses, wherein the inflection region is a first inflection region and the mesh further comprises a second inflection region, and wherein the first inflection region extends longitudinally along the occlusive device and the second inflection region extends laterally across the occlusive device.

Clause 59. The method of any one of the previous Clauses, wherein positioning the occlusive device at the aneurysm comprises deploying the mesh across the neck of the aneurysm and then deploying the coil within the aneurysm cavity between the mesh and the aneurysm wall.

Clause 60. An assembly, comprising:
a first fixture having a convex surface bound between opposing longitudinal ends and opposing side edges, the convex surface having a length between its longitudinal ends and a width between its side edges, wherein the convex surface is curved along its length and curved along its width, the convex surface having an indentation that extends inwardly from the convex surface; and
a second fixture having a convex portion configured to mate with the indentation of the convex surface.

Clause 61. The assembly of any one of the preceding Clauses, wherein the second fixture has a concave surface and the convex portion protrudes from the concave surface.

Clause 62. The assembly of any one of the preceding Clauses, wherein the concave surface of the second fixture is bound between longitudinal ends and opposing side edges, the concave surface having a length between its longitudinal ends and a width between its side edges, where the concave surface is curved along its length and curved along its width.

Clause 63. The assembly of any one of the preceding Clauses, further comprising a mesh positioned between the convex and concave surfaces.

Clause 64. The assembly of any one of the preceding Clauses, wherein the convex surface of the first fixture has a first circumferential length with a first radius of curvature and a second circumferential length with a second radius of curvature greater than the first radius of curvature.

Clause 65. The assembly of any one of the preceding Clauses, wherein the concave surface of the second fixture has a first circumferential length with a first radius of curvature and a second circumferential length with a second radius of curvature greater than the first radius of curvature.

Clause 66. The assembly of any one of the preceding Clauses, wherein the assembly is configured to receive a mesh between the first and second fixtures.

Clause 67. The assembly of any one of the preceding Clauses, wherein the assembly is configured to withstand a heat treatment process.

Clause 68. The assembly of any one of the preceding Clauses, wherein the indentation extends in a longitudinal direction along the first fixture.

Clause 69. The assembly of any one of the preceding Clauses, wherein the indentation extends laterally across the first fixture.

Clause 70. The assembly of any one of the preceding Clauses, wherein the indentation is a first indentation and the first fixture includes a second indentation in the convex surface, wherein the first indentation extends in a longitudinal direction along the first fixture and the second indentation extends laterally across a width of the first fixture.

Clause 71. A method for making an occlusive device with a forming assembly, the method comprising:
positioning a mesh between first and second members such that the mesh conforms to mating surfaces of the first and second members;
heat treating the mesh while the mesh is held between the first and second members.

Clause 72. The method of any one of the previous Clauses, wherein the mesh is a generally flat ribbon and the method further comprises forming the generally flat ribbon, wherein forming the generally flat ribbon comprises flattening a tubular mesh such that opposing portions of a sidewall of the mesh are urged towards one another.

Clause 73. The method of any one of the previous Clauses, wherein the mesh is a tubular braid.

Clause 74. The method of any one of the previous Clauses, wherein the first member has a convex surface with an indentation and the second member has a concave surface with a protrusion, and wherein the method further comprises aligning the indentation with the protrusion when the mesh is positioned between the first and second members.

Clause 75. The method of any one of the previous Clauses, wherein the first member has a convex surface that is bound between opposing longitudinal ends and opposing side edges, the convex surface having a length between its longitudinal ends and a width between its side edges, wherein the convex surface is curved along its length and curved along its width, the convex surface having an indentation that extends inwardly from the convex surface.

Clause 76. The method of any one of the preceding Clauses, wherein the second member has a convex portion configured to mate with an indentation of a convex surface of the first member.

Clause 77. The method of any one of the preceding Clauses, wherein the second member has a concave surface and the convex portion protrudes from the concave surface.

Clause 78. The method of any one of the preceding Clauses, wherein the concave surface of the second fixture is bound between longitudinal ends and opposing side edges, the concave surface having a length between its longitudinal ends and a width between its side edges, where the concave surface is curved along its length and curved along its width.

Clause 79. The method of any one of the preceding Clauses, further comprising a mesh positioned between the convex and concave surfaces.

Clause 80. The method of any one of the preceding Clauses, wherein the convex surface of the first member has a first circumferential length with a first radius of curvature and a second circumferential length with a second radius of curvature greater than the first radius of curvature.

Clause 81. The method of any one of the preceding Clauses, wherein the concave surface of the second member has a first circumferential length with a first radius of curvature and a second circumferential length with a second radius of curvature greater than the first radius of curvature.

Clause 82. The method of any one of the preceding Clauses, wherein the assembly is configured to receive a mesh between the first and second fixtures.

Clause 83. The method of any one of the preceding Clauses, wherein the assembly is configured to withstand a heat treatment process.

Clause 84. The method of any one of the preceding Clauses, wherein the indentation extends in a longitudinal direction along the first member.

Clause 85. The method of any one of the preceding Clauses, wherein the indentation extends laterally across the first member.

Clause 86. The method of any one of the preceding Clauses, wherein the indentation is a first indentation and the first member includes a second indentation in the convex surface, wherein the first indentation extends in a longitudinal direction along the first member and the second indentation extends laterally across a width of the first fixture.

Clause 87. An intrasaccular device for treating an aneurysm located along a parent cerebral blood vessel, wherein a neck of the aneurysm opens to the parent vessel, the device comprising:
- a multi-layer mesh formed of a plurality of braided filaments, the mesh having a low-profile state for intravascular delivery to the aneurysm and a deployed state in which the mesh is configured to be positioned within the aneurysm across the neck, wherein the mesh further comprises—
  - a distal end, a proximal end, and a length extending between the distal and proximal ends,
  - a first lateral edge, a second lateral edge, and a width extending between the first and second lateral edges, wherein the width of the mesh tapers towards each of the distal end and the proximal end;
  - a longitudinal divot extending along a portion of the length of the mesh,
  - a first side, a second side opposite the first side, and a thickness therebetween, the thickness corresponding to a combined thickness of the layers of the mesh, wherein (a) the first side has a ridge corresponding to the divot and first shoulder portions on either side of the ridge, and (b) the second side has a groove corresponding to the divot and second shoulder portions on either side of the groove, and
  - wherein, when the mesh is in the deployed state, the mesh is curved along its width and curved along its length such that, when the mesh is positioned within the aneurysm and across the neck of the aneurysm: (a) the first side faces the dome of the aneurysm with the first shoulder portions concave towards the dome and the ridge convex towards the dome, and (b) the second side faces the parent vessel with the second shoulder portions convex towards the parent vessel and the groove concave towards the parent vessel;
- a distal band disposed at and surrounding the distal end of the mesh;
- a proximal band disposed at and surrounding the proximal end of the mesh, wherein the proximal and distal bands are offset from one another about a plane bisecting the width of the mesh; and
- a coil having (a) a proximal end configured to be detachably coupled to a delivery device, and (b) a distal end coupled to the proximal end of the mesh, wherein the distal end of the coil is positioned over at least a portion of the proximal band;
- wherein the intrasaccular device is configured to be positioned within the aneurysm such that the mesh extends over the neck of the aneurysm and the coil is positioned between the mesh and the dome of the aneurysm.

Clause 88. The device of Clause 87, wherein the mesh further comprises an intermediate region at its proximal end, wherein the intermediate region comprises a radially-compacted portion of the mesh, and wherein the intermediate region is configured to re-orient the mesh as it is being pushed from a delivery catheter such that, when the intermediate region is pushed from the delivery catheter, the intermediate region forces the mesh to rotate around an inner wall of the aneurysm wall within a plane that crosses the neck.

Clause 89. The device of Clause 87, wherein the coil is a first coil and the device further comprises a lead-in member coupled to and extending from the distal end of the mesh, wherein the lead-member comprises a second coil having a preset curve.

Clause 90. The device of Clause 89, wherein the lead-in member further comprises a strand of a stretch-resistant material that extends through a lumen of the second coil.

Clause 91. An assembly for forming an occlusive mesh configured to treat a cerebral aneurysm, the assembly comprising:
- a first member having a first surface bound between opposing first longitudinal ends and opposing first side edges, the first surface having a first length between the first longitudinal ends and a first width between the first side edges, wherein the first surface is curved along the first length and curved along the first width, and wherein the first surface has a first convex region and a first concave region; and
- a second member having a second surface bound between opposing second longitudinal ends and opposing second side edges, the second surface having a second length between the second longitudinal ends and a second width between the second side edges, wherein the second surface is curved along the second length and curved along the second width, and wherein the second surface has a second convex region complementary to the first concave region and a second concave region complementary to the first convex region, and
- wherein the assembly is configured to receive a mesh between the first and second surfaces.

Clause 92. The assembly of any one of the preceding Clauses, wherein the first concave region is surrounded by the first convex region.

Clause 93. The assembly of any one of the preceding Clauses, wherein the second convex region is surrounded by the second concave region.

Clause 94. The assembly of any one of the preceding Clauses, wherein:
the first concave region is surrounded by the first convex region, and
the second convex region is surrounded by the second concave region.

Clause 95. The assembly of any one of the preceding Clauses, wherein the mesh is a flattened tubular braid.

Clause 96. The assembly of any one of the preceding Clauses, wherein the first convex region has a radius of curvature that increases continuously along the first length.

Clause 97. The assembly of any one of the preceding Clauses, wherein the second concave region has a radius of curvature that increases continuously along the second length.

Clause 98. The assembly of any one of the preceding Clauses, wherein a radius of curvature of the first convex region is greater than a radius of curvature of the first concave region.

Clause 99. The assembly of any one of the preceding Clauses, wherein a radius of curvature of the second convex region is less than a radius of curvature of the second concave region.

Clause 100. The assembly of any one of the preceding Clauses, wherein the assembly is configured to withstand the application of heat at a temperature sufficient to shape set the mesh while the mesh is between the first and second surfaces.

Clause 101. The assembly of any one of the preceding Clauses, wherein the first concave region is a divot.

Clause 102. The assembly of Clause 101, wherein the divot extends laterally across at least a portion of the first width.

Clause 103. The assembly of Clause 101, wherein the divot extends lengthwise across at least a portion of the first surface.

Clause 104. The assembly of any one of the preceding Clauses, wherein the side edges of the first surface are generally parallel to one another.

Clause 105. The assembly of any one of the preceding Clauses, wherein the side edges of the second surface are generally parallel to one another.

Clause 106. The assembly of any one of the preceding Clauses, further comprising a groove in the first surface, wherein the groove extends diagonally relative to the first side edges.

Clause 107. The assembly of Clause 106, wherein the groove is a first groove disposed at one of the first longitudinal ends and the first surface further comprises a second groove disposed at the other of the first longitudinal ends.

Clause 108. The assembly of any one of the preceding Clauses, wherein the first concave region is a first longitudinal concave region that extends along at least a portion of the first length and the first surface further includes a first lateral concave region that extends along at least a portion of the first width.

Clause 109. The assembly of Clause 108, wherein the first longitudinal concave region and the second longitudinal concave region intersect one another.

Clause 110. The assembly of Clause 108, wherein the first longitudinal concave region and the second longitudinal concave region are spaced apart from one another.

Clause 111. The assembly of Clause 108, wherein:
the first longitudinal concave region has a first average radius of curvature, the first lateral concave region has a second average radius of curvature, and the first convex region has a third average radius of curvature, and
each of the first and second average radii of curvature are less than the third average radius of curvature.

Clause 112. A method for making an occlusive device configured to treat an aneurysm, the method comprising:
positioning a mesh between first and second members of a forming assembly such that the mesh conforms to first and second surfaces of the first and second members, respectively, wherein:
the first surface is bound between opposing first longitudinal ends and opposing first side edges, the first surface having a first length between the first longitudinal ends and a first width between the first side edges, wherein the first surface is curved along the first length and curved along the first width, and wherein the first surface has a first convex region and a first concave region; and
the second surface bound between opposing second longitudinal ends and opposing second side edges, the second surface having a second length between the second longitudinal ends and a second width between the second side edges, wherein the second surface is curved along the second length and curved along the second width, and wherein the second surface has a second convex region complementary to the first concave region and a second concave region complementary to the first convex region, and
applying heat to the assembly forming assembly and the mesh while the mesh is held between the first and second members.

Clause 113. The method of any one of the previous Clauses, wherein the mesh is a generally flat ribbon and the method further comprises forming the generally flat ribbon, wherein forming the generally flat ribbon comprises flattening a tubular mesh such that opposing portions of a sidewall of the mesh are urged towards one another.

Clause 114. The method of any one of the previous Clauses, further comprising compressing the mesh between the first and second members.

Clause 115. The method of any one of the preceding Clauses, wherein the first concave region is surrounded by the first convex region.

Clause 116. The method of any one of the preceding Clauses, wherein the second convex region is surrounded by the second concave region.

Clause 117. The method of any one of the preceding Clauses, wherein:
the first concave region is surrounded by the first convex region, and
the second convex region is surrounded by the second concave region.

Clause 118. The method of any one of the preceding Clauses, wherein the mesh is a flattened tubular braid.

Clause 119. The method of any one of the preceding Clauses, wherein the first convex region has a radius of curvature that increases continuously along the first length.

Clause 120. The method of any one of the preceding Clauses, wherein the second concave region has a radius of curvature that increases continuously along the second length.

Clause 121. The method of any one of the preceding Clauses, wherein a radius of curvature of the first convex region is greater than a radius of curvature of the first concave region.

Clause 122. The method of any one of the preceding Clauses, wherein a radius of curvature of the second convex region is less than a radius of curvature of the second concave region.

Clause 123. The method of any one of the preceding Clauses, wherein the assembly is configured to withstand the application of heat at a temperature sufficient to shape set the mesh while the mesh is between the first and second surfaces.

Clause 124. The method of any one of the preceding Clauses, wherein the first concave region is a divot.

Clause 125. The method of Clause 124, wherein the divot extends laterally across at least a portion of the first width.

Clause 126. The method of Clause 124, wherein the divot extends lengthwise across at least a portion of the first surface.

Clause 127. The method of any one of the preceding Clauses, further comprising positioning the mesh between the first lateral edges such that the mesh, as positioned on the first surface, is laterally bound between the first lateral edges.

Clause 128. The method of any one of the preceding Clauses, wherein the side edges of the first surface are generally parallel to one another.

Clause 129. The method of any one of the preceding Clauses, wherein the side edges of the second surface are generally parallel to one another.

Clause 130. The method of any one of the preceding Clauses, further comprising a groove in the first surface, wherein the groove extends diagonally relative to the first side edges.

Clause 131. The method of Clause 130, further comprising securing an edge of the mesh along the first groove.

Clause 132. The method of Clause 130, wherein the groove is a first groove disposed at one of the first longitudinal ends and the first surface further comprises a second groove disposed at the other of the first longitudinal ends.

Clause 133. The method of Clause 132, wherein the mesh comprises a sheet having opposing first and second lateral edges, the method further comprising securing a first lateral edge along the first groove and a second lateral edge along the second groove.

Clause 134. The method of any one of the preceding Clauses, wherein the first concave region is a first longitudinal concave region that extends along at least a portion of the first length and the first surface further includes a first lateral concave region that extends along at least a portion of the first width.

Clause 135. The method of Clause 134, wherein the first longitudinal concave region and the second longitudinal concave region intersect one another.

Clause 136. The method of Clause 134, wherein the first longitudinal concave region and the second longitudinal concave region are spaced apart from one another.

Clause 137. The method of Clause 134, wherein:
the first longitudinal concave region has a first average radius of curvature, the first lateral concave region has a second average radius of curvature, and the first convex region has a third average radius of curvature, and
each of the first and second average radii of curvature are less than the third average radius of curvature.

Clause 138. An occlusive device for treating an aneurysm, wherein a neck of the aneurysm opens to a blood vessel, the device comprising:

a mesh having a low-profile state for intravascular delivery to the aneurysm and a deployed state, the mesh comprising—
a distal end, a proximal end, and a length extending between the distal and proximal ends,
a first lateral edge, a second lateral edge, and a width extending between the first and second lateral edges, and
a first side and a second side opposite the first side along a thickness of the mesh,
wherein the mesh is curved along its length and its width;
an embolic element coupled to the proximal end of the mesh at a joint, the embolic element having a proximal end and a distal end; and
a guide positioned between the mesh and the embolic element, the guide having a preset curve along its length configured to orient the mesh relative to the joint such that a first side of the mesh is facing the joint and the second side of the mesh is facing away from the joint,
wherein the mesh is configured to be positioned within the aneurysm in the deployed state such that the mesh extends over the neck of the aneurysm and the embolic element is positioned between the mesh and the dome of the aneurysm.

Clause 139. The device of any one of the preceding Clauses, wherein the guide comprises a radially-compacted portion of the mesh.

Clause 140. The device of any one of the preceding Clauses, wherein the guide is a component separate from the mesh.

Clause 141. The device of any one of the preceding Clauses, wherein an average cross-sectional dimension of the guide in a delivery configuration is substantially the same as an average cross-sectional dimension of the guide in a deployed configuration.

Clause 142. The device of any one of the preceding Clauses, wherein a greatest cross-sectional dimension of the guide in a deployed configuration is less than a greatest cross-sectional dimension of the mesh in the deployed state.

Clause 143. The device of any one of the preceding Clauses, wherein the first side of the mesh is concave.

Clause 144. The device of any one of the preceding Clauses, wherein the second side of the mesh is convex.

Clause 145. The device of any one of the preceding Clauses, wherein the guide includes a curved portion that includes a turn between about 120 degrees and about 240 degrees.

Clause 146. The device of any one of the preceding Clauses, wherein the guide includes a curved portion that includes a turn between about 150 degrees and 210 degrees.

Clause 147. The device of any one of the preceding Clauses, wherein the guide includes a curved portion that includes a turn of about 180 degrees.

Clause 148. The device of any one of the preceding Clauses, wherein the mesh is formed of a plurality of braided filaments.

Clause 149. The device of any one of the preceding Clauses, wherein the mesh includes a first layer and a second layer, and wherein, in an expanded, unconstrained state, the first layer generally conforms to the second layer such that the mesh does not include an interior volume.

Clause 150. The device of any one of the preceding Clauses, wherein the mesh includes a first layer and a second layer, and wherein, in an expanded, unconstrained state, the thickness of the mesh is generally equivalent to a combined thickness of the individual first and second layers.

Clause 151. The device of any one of the preceding Clauses, wherein the embolic element is a coil.

Clause 152. An occlusive device for treating an aneurysm of a patient, wherein a neck of the aneurysm opens to a blood vessel, the device comprising:
- a mesh having a low-profile state for intravascular delivery to the aneurysm and a deployed state, the mesh comprising—
  - a distal end, a proximal end, and a length extending between the distal and proximal ends,
  - a first lateral edge, a second lateral edge, and a width extending between the first and second lateral edges, and
  - a first side and a second side opposite the first side along a thickness of the mesh,
  - wherein the mesh is curved along the length and the width;
- an embolic element coupled to the proximal end of the mesh at a joint, the embolic element having a proximal end and a distal end; and
- a guide positioned between the mesh and the embolic element, the guide having a preset curve along its length,
- wherein, when the occlusive device is positioned within a delivery catheter and a portion of the occlusive device extending between a proximal terminus of the guide and a distal terminus of the mesh have been pushed from the delivery catheter into an open space outside of a body of the patient such that the mesh and guide are in respective expanded, unconstrained configurations, the preset curve is configured to orient the mesh relative to the delivery catheter such that a concave surface of the mesh is facing the same direction as a convex portion of the preset curve,
- wherein the mesh is configured to be positioned within the aneurysm in the deployed state such that the mesh extends over the neck of the aneurysm and the embolic element is positioned between the mesh and the dome of the aneurysm.

Clause 153. The device of any one of the preceding Clauses, wherein, when the occlusive device is positioned within the delivery catheter and the portion of the occlusive device extending between the proximal terminus of the guide and the distal terminus of the mesh have been pushed from the delivery catheter into the open space outside of the body of the patient such that the mesh and guide are in respective expanded, unconstrained configurations, the preset curve is configured to orient the mesh relative to the delivery catheter such that one of the first or second lateral edges is adjacent the delivery catheter.

Clause 154. The device of any one of the preceding Clauses, wherein, when the occlusive device is positioned within the delivery catheter and the portion of the occlusive device extending between the proximal terminus of the guide and the distal terminus of the mesh have been pushed from the delivery catheter into the open space outside of the body of the patient such that the mesh and guide are in respective expanded, unconstrained configurations, the preset curve is configured to orient the mesh relative to the delivery catheter such that a concave surface of the mesh and a concave portion of the curve are facing towards one another.

Clause 155. The device of any one of the preceding Clauses, wherein the guide comprises a radially-compacted portion of the mesh.

Clause 156. The device of any one of the preceding Clauses, wherein the guide is a component separate from the mesh.

Clause 157. The device of any one of the preceding Clauses, wherein an average cross-sectional dimension of the guide in a delivery configuration is substantially the same as an average cross-sectional dimension of the guide in a deployed configuration.

Clause 158. The device of any one of the preceding Clauses, wherein a greatest cross-sectional dimension of the guide in a deployed configuration is less than a greatest cross-sectional dimension of the mesh in the deployed state.

Clause 159. The device of any one of the preceding Clauses, wherein the first side of the mesh is concave.

Clause 160. The device of any one of the preceding Clauses, wherein the second side of the mesh is convex.

Clause 161. The device of any one of the preceding Clauses, wherein the guide includes a curved portion that includes a turn between about 120 degrees and about 240 degrees.

Clause 162. The device of any one of the preceding Clauses, wherein the guide includes a curved portion that includes a turn between about 150 degrees and 210 degrees.

Clause 163. The device of any one of the preceding Clauses, wherein the guide includes a curved portion that includes a turn of about 180 degrees.

Clause 164. The device of any one of the preceding Clauses, wherein the mesh is formed of a plurality of braided filaments.

Clause 165. The device of any one of the preceding Clauses, wherein the mesh includes a first layer and a second layer, and wherein, in an expanded, unconstrained state, the first layer generally conforms to the second layer such that the mesh does not include an interior volume.

Clause 166. The device of any one of the preceding Clauses, wherein the mesh includes a first layer and a second layer, and wherein, in an expanded, unconstrained state, the thickness of the mesh is generally equivalent to a combined thickness of the individual first and second layers.

Clause 167. The device of any one of the preceding Clauses, wherein the embolic element is a coil.

Clause 168. An occlusive device for treating an aneurysm, wherein a neck of the aneurysm opens to a blood vessel, the device comprising:
- a mesh having a low-profile state for intravascular delivery to the aneurysm and a deployed state, the mesh comprising—
  - a first end portion, a second end portion, and a length extending between the first and second end portions, and
  - a first lateral edge, a second lateral edge, and a width extending between the first and second lateral edges,
  - wherein the mesh has a predetermined shape in an expanded, unconstrained state in which (a) the mesh is curved along its width, (b) the mesh is curved along its length, and (c) the mesh has an undulating contour across at least a portion of its length, and
- wherein the mesh is configured to be positioned within the aneurysm in the deployed state such that the mesh extends over the neck of the aneurysm.

Clause 169. The occlusive device of any one of the preceding Clauses, wherein, at least in the deployed state, the mesh comprises a curved member having a plurality of undulations.

Clause 170. The occlusive device of claim 2, wherein the mesh has a first side and a second side opposite the first side, and wherein the plurality of undulations comprise a first inflection region comprising a first peak at the first side and a first valley at the second side, a second inflection region comprising a second valley at the first side and a second peak at the second side, and a third inflection region comprising a third peak at the first side and a third valley at the second side, and wherein the mesh is configured to be positioned within an aneurysm such that the first side faces a cavity of the aneurysm and the second side faces the blood vessel.

Clause 171. The occlusive device of claim 3, wherein the mesh is configured to be positioned within the aneurysm such that the second peak is convex towards the aneurysm cavity.

Clause 172. The occlusive device of any one of the preceding Clauses, wherein the mesh has a first side, a second side opposite the first side, and a thickness measured therebetween, and wherein the mesh has a generally constant thickness along its length.

Clause 173. The occlusive device of any one of the preceding Clauses, wherein the mesh does not define an inner cavity.

Clause 174. The occlusive device of any one of the preceding Clauses, wherein the mesh is formed of a tubular braid that has been flattened along its longitudinal axis such that opposing portions of a sidewall of the tubular braid are urged towards one another.

Clause 175. The occlusive device of any one of the preceding Clauses, wherein the width of the mesh tapers in the direction of the first end portion.

Clause 176. The occlusive device of any one of the preceding Clauses, wherein the width of the mesh tapers in the direction of the second end portion.

Clause 177. The occlusive device of any one of the preceding Clauses, wherein the mesh is formed of a plurality of filaments, and wherein at least some of the filaments are drawn-filled tube ("DFT") wires.

Clause 178. The occlusive device of any one of the preceding Clauses, wherein a proximal end of the mesh is configured to be detachably coupled to an elongated delivery member.

Clause 179. The occlusive device of any one of the preceding Clauses, wherein a proximal end of the occlusive device is configured to be detachably coupled to an elongated delivery member.

Clause 180. The occlusive device of any one of the preceding Clauses, further comprising an embolic element coupled to a proximal end of the mesh.

Clause 181. The occlusive device of any one of the preceding Clauses, further comprising a lead-in member coupled to a distal end of the mesh.

Clause 182. The occlusive device of any one of the preceding Clauses, wherein a radius of curvature of the mesh increases distally along its longitudinal axis between its proximal and distal ends.

Clause 183. The occlusive device of any one of the preceding Clauses wherein a radius of curvature of the mesh decreases distally along its longitudinal axis between its proximal and distal ends.

Clause 184. The occlusive device of any one of the preceding Clauses, wherein a radius of curvature of the mesh is generally constant along its longitudinal axis between its proximal and distal ends.

Clause 185. The occlusive device of any one of the preceding Clauses, wherein, when the occlusive device is positioned in the aneurysm, the proximal end of the mesh does not overlap the distal end of the mesh.

Clause 186. An occlusive device for treating an aneurysm, wherein a neck of the aneurysm opens to a blood vessel, the device comprising:
- a mesh having a low-profile state for intravascular delivery to the aneurysm and a deployed state, the mesh comprising—
  - a first end portion, a second end portion, and a length extending between the first and second end portions, and
  - a first lateral edge, a second lateral edge, and a width extending between the first and second lateral edges; and
- an elongated embolic element coupled to the mesh;
- wherein the mesh has a predetermined shape in an expanded, unconstrained state in which (a) the mesh is curved along its width, (b) the mesh is curved along its length, and (c) the mesh has a first region, a second region, and a third region extending along its length, the second region being disposed between the first and third regions, and
- wherein the occlusive device is configured to be positioned within the aneurysm such that the mesh extends over the neck of the aneurysm and the elongated embolic element is positioned between a dome of the aneurysm and the mesh, and
- wherein, wherein the mesh is in the deployed state and positioned within the aneurysm with the mesh positioned across the neck of the aneurysm, the first and third regions of the mesh are concave towards the dome of the aneurysm and the second region of the mesh is convex towards the dome of the aneurysm.

Clause 187. The occlusive device of any one of the preceding Clauses, wherein the mesh and the embolic element are coupled end-to-end.

Clause 188. The occlusive device of any one of the preceding Clauses, wherein the mesh and the embolic element are coupled end-to-end and such that, when positioned within a delivery catheter for intravascular delivery to the aneurysm, the mesh is distal of the embolic element in the delivery catheter so that the mesh is delivered to the aneurysm before the embolic element.

Clause 189. The occlusive device of any one of the preceding Clauses, wherein the embolic element is a coil.

Clause 190. The occlusive device of any one of the preceding Clauses, wherein the embolic element and the mesh are coupled at a joint, and wherein the embolic element and the mesh are configured to bend and twist relative to one another at the joint.

Clause 191. The occlusive device of Clause 190, wherein the first end portion of the mesh includes a band, and wherein an end portion of the embolic element is positioned over at least a portion of the band at the joint.

Clause 192. An occlusive device for treating an aneurysm, wherein a neck of the aneurysm opens to a blood vessel, the device comprising:
- a mesh having a low-profile state for intravascular delivery to the aneurysm and a deployed state, the mesh comprising—
  - a first end portion, a second end portion, and a length extending between the first and second end portions,
  - a first lateral edge, a second lateral edge, and a width extending between the first and second lateral edges, and
  - a first side, a second side opposite the first side, and a thickness extending therebetween, and
- wherein, in the deployed state, the mesh has a first surface at the first side and a second surface at the second side, the first surface is bound between opposing first longitudinal ends and opposing first side edges, the first surface having a first length between the first longitudinal ends and a first width between the first side edges, wherein the first surface has a first convex region and a first concave region; and the second surface is bound between opposing second longitudinal ends and opposing second side edges, the second surface having a second length between the second longitudinal ends and a second width between the second side edges, wherein the second surface has a second convex region and a second concave region, and wherein the mesh is configured to be positioned within the aneurysm in the deployed state such that the mesh extends over the neck of the aneurysm.

Clause 193. The device of any one of the preceding Clauses, wherein the first concave region is surrounded by the first convex region.

Clause 194. The device of any one of the preceding Clauses, wherein the second convex region is surrounded by the second concave region.

Clause 195. The device of any one of the preceding Clauses, wherein:
the first concave region is surrounded by the first convex region, and
the second convex region is surrounded by the second concave region.

Clause 196. The device of any one of the preceding Clauses, wherein the mesh is a flattened tubular braid.

Clause 197. The device of any one of the preceding Clauses, wherein the first convex region has a radius of curvature that increases continuously along the first length.

Clause 198. The device of any one of the preceding Clauses, wherein the second concave region has a radius of curvature that increases continuously along the second length.

Clause 199. The device of any one of the preceding Clauses, wherein a radius of curvature of the first convex region is greater than a radius of curvature of the first concave region.

Clause 200. The device of any one of the preceding Clauses, wherein a radius of curvature of the second convex region is less than a radius of curvature of the second concave region.

Clause 201. The device of any one of the preceding Clauses, wherein the first concave region and the second convex region correspond to a longitudinal divot extending along at least a portion of the length of the mesh.

Clause 202. The device of any one of the preceding Clauses, wherein the mesh comprises a first layer and a second layer that meet at the first and second lateral edges.

Clause 203. The device of any one of the preceding Clauses, wherein the mesh has a generally constant thickness along its length.

Clause 204. An occlusive device for treating an aneurysm, wherein a neck of the aneurysm opens to a blood vessel, the device comprising:
a mesh having a low-profile state for intravascular delivery to the aneurysm and a deployed state, the mesh comprising—
a first end portion, a second end portion, and a length extending between the first and second end portions, and
a first lateral edge, a second lateral edge, and a width extending between the first and second lateral edges;
a first side, a second side opposite the first side, and a thickness therebetween; and
an elongated embolic element coupled to the mesh;
wherein the mesh has a predetermined shape in the deployed state in which (a) the mesh is curved along its width, (b) the mesh is curved along its length, and (c) the mesh has a first region, a second region, and a third region extending along its width such that the first region is closest to the first lateral edge and the third region is closest to the second lateral edge, the second region being disposed between the first and third regions, and
wherein, wherein the mesh is in an expanded, unconstrained configuration, the first and third regions of the mesh are concave towards the first side and the second region of the mesh is convex towards the first side,
wherein the occlusive device is configured to be positioned within the aneurysm such that the mesh extends over the neck of the aneurysm and the elongated embolic element is positioned between a dome of the aneurysm and the mesh.

Clause 205. The occlusive device of any one of the preceding Clauses, wherein the occlusive device is configured to be positioned in the aneurysm in a deployed state such that the first side of the mesh faces a dome of the aneurysm and a second side of the mesh faces the neck of the aneurysm.

Clause 206. The occlusive device of any one of the preceding Clauses, wherein the mesh and the embolic element are coupled end-to-end.

Clause 207. The occlusive device of any one of the preceding Clauses, wherein the mesh and the embolic element are coupled end-to-end and such that, when positioned within a delivery catheter for intravascular delivery to the aneurysm, the mesh is distal of the embolic element in the delivery catheter so that the mesh is delivered to the aneurysm before the embolic element.

Clause 208. The occlusive device of any one of the preceding Clauses, wherein the embolic element is a coil.

Clause 209. The occlusive device of any one of the preceding Clauses, wherein the embolic element and the mesh are coupled at a joint, and wherein the embolic element and the mesh are configured to bend and twist relative to one another at the joint.

Clause 210. The occlusive device of Clause 210, wherein the first end portion of the mesh includes a band, and wherein an end portion of the embolic element is positioned over at least a portion of the band at the joint.

Clause 211. The occlusive device of any one of the preceding Clauses, wherein the mesh is formed of a flattened tubular braid.

BRIEF DESCRIPTION OF THE DRAWINGS

FIG. 4A is a bottom isometric view of a portion of an occlusive device in an unconstrained state outside of an aneurysm according to some embodiments of the present technology.

FIG. 4B is an end view of the occlusive device shown in FIG. 4A.

FIG. 4C is a side view of the occlusive device shown in FIG. 4A.

FIGS. 12A-12D are different views of an occlusive device of the present technology.

In FIG. 20, the forming assembly is shown prior to assembly with a mesh to be formed.

In FIG. 23, the forming assembly is shown in an assembled configuration, without a mesh between the base and outer members.

DETAILED DESCRIPTION

Figure 1A:
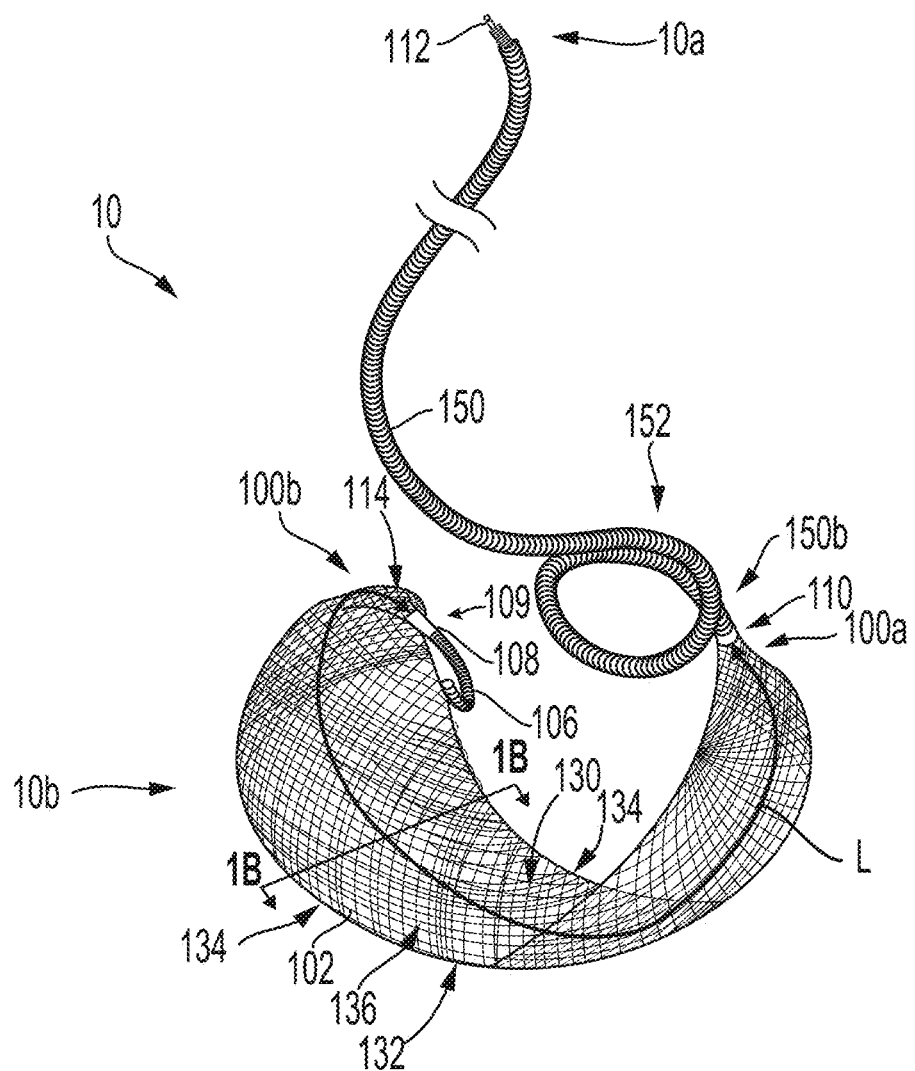
FIG. 1A shows an occlusive device in an unconstrained state outside of an aneurysm according to some embodiments of the present technology.

FIG. 1A shows an occlusive device 10 (or "device 10") in accordance with the present technology, shown in an expanded configuration. The occlusive device 10 may comprise a mesh structure 100 (or "mesh 100") coupled to a coil 150. For delivery to the aneurysm, the occlusive device 10 is configured to be positioned in a compressed or low-profile state within a delivery catheter (e.g., a microcatheter) (not shown) so that the distal end portion 100b of the mesh 100 is closest to the distal opening of the delivery catheter and thus will be released from the delivery catheter before the coil 150. As a result, the coil 150 deploys within and fills an interior region at least partially defined by the already-expanded mesh 100.

The occlusive device 10 is configured to be deployed within the interior cavity of an aneurysm (such as a cerebral aneurysm) such that the mesh 100 is positioned over the neck of the aneurysm while the coil 150 fills space within the aneurysmal cavity and stabilizes and/or anchors the mesh 100 at the neck. The presence of the mesh 100 over the neck prevents any portion of the coil 150 from protruding from the aneurysm sac into the parent vessel. When positioned across the neck of the aneurysm, the mesh 100 also (a) substantially reduces and/or prevents further blood flow from the parent vessel into the aneurysm sac by disrupting blood flow from the parent vessel into the aneurysm, and (b) provides a scaffold for endothelial cell attachment. The growth and development of an endothelial layer over the neck of an aneurysm can wall off the aneurysm from the parent vessel and allow flow dynamics to equilibrate at the defect. As such, the device 10 is configured to facilitate healing of the defect and preventing recanalization by promoting tissue creation that resists aberrant blood flow and redistributes the flow pressure that may have created the defect. Upon healing with endothelialization, the pressure is evenly distributed along the parent vessel in a manner that prevents recanalization at the defect post-treatment. Moreover, blood from within the parent vessel no longer has access to the walled off defect once the endothelialization process is complete.

Figure 1B:
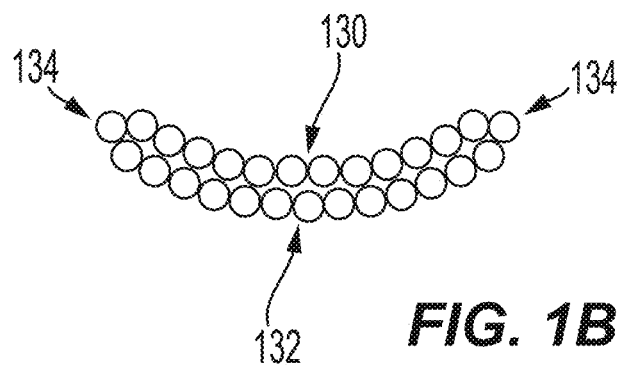
FIG. 1B is a cross-sectional end view of the occlusive device of FIG. 1A taken along line 1B-1B.

FIG. 1B is a top view of the occlusive device 10 after being unfurled from the configuration shown in FIG. 1A and held in a laid-flat configuration to provide a better view of the entire length of the occlusive device 10. Referring to FIGS. 1A and 1B together, the occlusive device 10 has a proximal end portion 10a, a distal end portion 10b, and a longitudinal axis L extending between the proximal and distal end portions 10a, 10b. In some embodiments, the occlusive device 10 may optionally have a soft, curved lead-in member 106 at its distal end portion 10b, and a detach element 112 at its proximal end portion 10a. The occlusive device 10 may have a distal joint 109 between the lead-in member 106 and a distal end 100b of the mesh 100, an intermediate joint 110 between a proximal end portion 100a of the mesh 100 and a distal end 150b of the coil 150, and a proximal joint 107 (shown in FIG. 1C only) between a proximal end 150a of the coil 150 and the detach element 112.

Figure 1C:
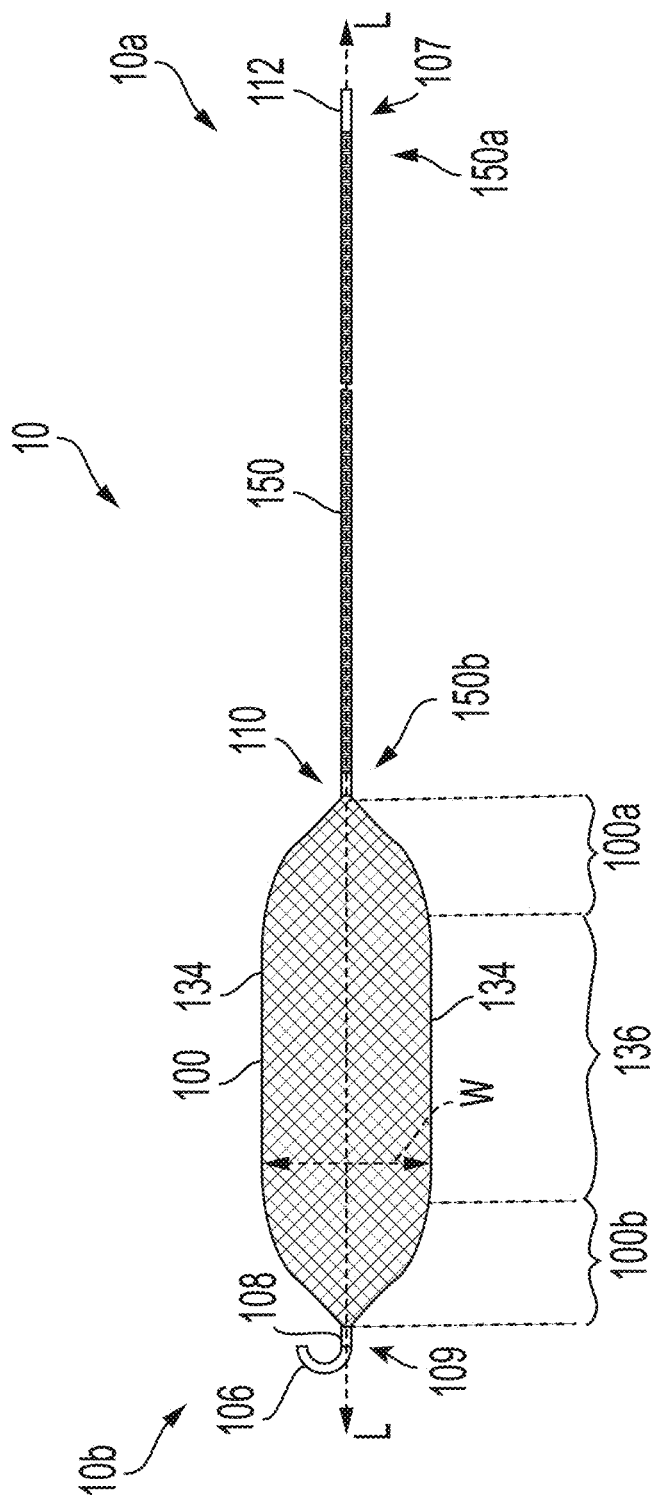
FIG. 1C is a top view of the occlusive device shown in FIG. 1A, unfurled and held in a laid-flat configuration.

The lead-in member 106 may have a preset, curved shape in a deployed configuration such that the curved portion of the lead-in member 106 forms an atraumatic surface for engaging an inner surface of the aneurysm wall. As shown in FIGS. 1A-1C, the lead-in member 106 may extend distally from the mesh 100 and/or distal joint 109 along the longitudinal axis L of the device 10 then curve proximally. In some embodiments, the lead-in member 106 may have a J-shape, and in some embodiments the lead-in member 106 may have a C-shape. Because the lead-in member 106 is the first portion of the occlusive device 10 that exits the delivery catheter and contacts the aneurysm wall, the soft material and/or curved shape of the lead-in member 106 reduces or eliminates stress on the aneurysm wall when delivering the occlusive device 10 to the aneurysm sac.

In some embodiments, such as that shown in FIGS. 1A-1C, the lead-in member 106 may be a flexible, soft tubular coil. For example, the lead-in member 106 may comprise a coil formed of a wire made of a soft and/or radiopaque metal or metal alloy, such as platinum, platinum tungsten alloy, and others. The wire may have a diameter of about 0.0010 to about 0.0020 inches (i.e., about 0.0010 inches, about 0.0011 inches, about 0.0012 inches, about 0.0013 inches, about 0.0014 inches, about 0.0015 inches, about 0.0016 inches, about 0.0017 inches, about 0.0018 inches, about 0.0019 inches, or about 0.0020 inches). In any case, the lead-in member 106 may comprise one or more radiopaque materials to improve visualization of the lead-in member 106 during delivery and positioning within the aneurysm sac.

In those embodiments where the lead-in member 106 is a tubular member, such as a tubular coil, the lead-in member 106 can optionally include a strand of material extending through the tubular member and fixed to either end of the tubular member such that the strand is configured to resist stretching of the tubular member. For example, the strand may have a proximal end coupled to a distal end of the mesh and a distal end coupled to a distal tip comprising the distal terminus of the lead-in member 106. The stretch-resistant member may be a suture strand, such as a polypropylene suture strand. The stretch-resistant member may have a diameter of about 0.0010 inches to about 0.0015 inches (i.e., about 0.0010 inches, 0.0011 inches, 0.0012 inches, 0.0013 inches, 0.0014 inches, or 0.0015 inches).

In some aspects of the technology, the lead-in member 106 may be generally straight (not shown) and/or have other atraumatic yet sufficiently resilient configurations. In some embodiments, the lead-in member 106 is a curled mesh (e.g., a braid) extending from the distal joint 109. The curled mesh can be integral with the mesh that forms the mesh 100, or the curled mesh can be a separate mesh coupled to the distal connector 108. In some embodiments, the lead-in member 106 can be formed integrally or monolithically with the occlusive device 10. In yet other embodiments, the occlusive device 10 does not include a lead-in member 106 and the distal portion of the occlusive device 10 is comprised solely of the distal connector 108 and/or distal end portion 100b of the mesh 100.

In some embodiments, the mesh 100 may include a directing region 114 (see FIG. 1A) that is heat set to form a predetermined bend in the mesh 100 (in the expanded configuration) that positions the lead-in member 106 at a predetermined angle relative to the mesh 100. The angle of the directing region 114 with respect to the mesh 100 directs the distal portion 10b of the device 10 away from exiting the aneurysm through the neck, and instead guides the distal portion 10b across the neck of the aneurysm A. The combination of (a) the preset angle between the directing region 114 and the mesh 100 and (b) the length of the directing region 114 relative to a diameter of the aneurysm enables the directing region 114 to direct the distal portion 10b as the occlusive device 10 is being pushed distally out of a delivery catheter into the aneurysm. As such, the directing region 114 inhibits the distal portion 10b from exiting the aneurysm through the neck and instead directs the mesh 100 to cross the neck and generally remain within the aneurysm. Examples of suitable directing regions for use with the occlusive devices of the present technology, including exemplary angles and lengths, can be found in U.S. patent Ser. No. 15/228,278, filed Aug. 4, 2016, which is incorporated by reference herein in its entirety.

The distal connector 108 may include a band at the distal joint (such as a marker band) that surrounds and holds together the distal ends of the mesh 100. In those embodiments wherein the lead-in member 106 includes a coil, a proximal end of the coil may be positioned within the band, thereby coupling the mesh 100 to the lead-in member 106. In some embodiments, a distal portion of the band (with the mesh ends therein) may be positioned within a lumen of the coil forming the lead-in member 106.

The proximal joint 107 may comprise a proximal end of the coil 150 coupled to a detach element 112 that is configured to detachably couple the occlusive device 10 to a delivery system, such as a pusher member (not shown). When coupled to the occlusive device 10, a pusher member may be configured to push the occlusive device 10 through the distal opening of a delivery catheter into the aneurysm cavity, and in some aspects pull the occlusive device 10 back into a distal end of the delivery catheter for repositioning. Detachment methods to disconnect the occlusive device 10 from a delivery system and/or pusher member include, for example, electrolytic detachment, mechanical detachment, thermal detachment, and electromagnetic detachment. An example of a suitable detachment means for use with the present technology is the Axium™ or Axium™ Prime Detachable Coil System (Medtronic).

Figure 1D:
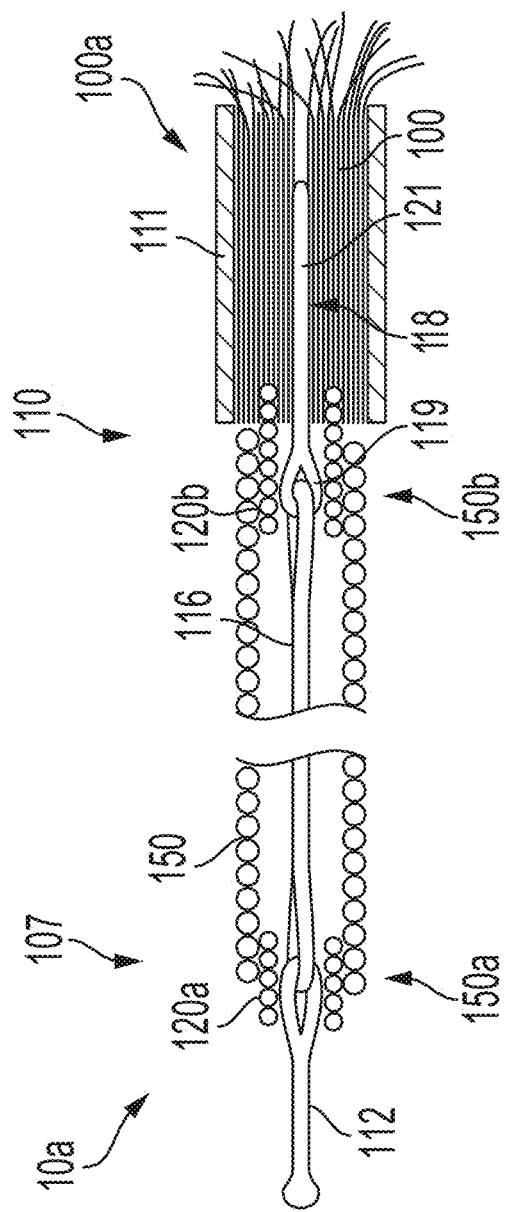
FIG. 1D is a schematic representation of attachment regions of the occlusive devices of the present technology.

In some embodiments, such as that shown in FIG. 1C, the detach element 112 comprises the proximal terminus of the occlusive device 10. An enlarged, cross-sectional view of portions of the occlusive device 10, including the proximal end 10a of the device 10, is shown in FIG. 1D. In those embodiments where the coil 150 comprises the proximal-most component of the device 10, the detach element 112 may be coupled to and extend proximally beyond a proximal end 150a of the coil 150 for engagement with a delivery system (for example, a pusher member as described above). In other embodiments, the detach element 112 may be coupled to another, more proximal component of the device 10.

As shown in FIG. 1D, a distal portion of the detach element 112 may be coupled to the proximal end 150a of the coil 150 via a securing element 120a. In some embodiments, the securing element 120a may be a generally tubular member configured to be at least partially positioned within the lumen of the coil 150 and defining a lumen configured to receive a distal portion of the detach element 112 therein. The tubular member may be, for example, a stent, a marker band, a coil, a tubular braid, a polymer tube, and others. In some embodiments, a distal portion of the securing element 120a may be positioned within a lumen of a proximal portion of the coil 150 while a proximal portion of the securing element 120a may extend proximally beyond the proximal end of the coil 150. The securing element 120a and coil 150 may be welded together to secure the connection. In some embodiments, the entire length of the securing element 120a may be positioned within the lumen of the coil 150. As depicted in the example shown at FIG. 1D, the detach element 112 may couple to the proximal end of an intermediate member 116 that extends distally from the detach element 112 through all or a portion of the length of the coil 150 (as described in greater detail below). In some embodiments the coupling region between the detach element 112 and the intermediate member 116 may be disposed within the lumen of the securing element 120a such that the securing element 120a secures that connection between the detach element 112 and the intermediate member 116.

In some embodiments, such as that shown in FIG. 1D, the securing element 120a may be a coil formed of one or more wires wound in a helical fashion about an axis to form an elongated tubular member. The wire(s) forming the coil 120a may be circular, square, or rectangular in cross-section, and may have a cross-sectional dimension of from about 0.001 inches to about 0.0045 inches, of from about 0.001 inches to about 0.004 inches, or of from about 0.0015 inches to about 0.0035 inches. In some embodiments, the wire(s) forming the coil 120a has a cross-sectional dimension, no greater than 0.004 inches, no greater than 0.0035 inches, no greater than 0.003 inches, no greater than 0.0025 inches, or no greater than 0.002 inches. The coil 120a may be circular, square, or rectangular in cross-section, and may have an outer cross-sectional dimension of from about 0.004 inches to about 0.012 inches, of from about 0.005 inches to about 0.01 inches, or from about 0.006 inches to about 0.01 inches. In some embodiments, the coil 120a may have an outer cross-sectional dimension that is no greater than 0.01 inches, and in some embodiments no greater than 0.009 inches. The coil 120a may be circular, square, or rectangular in cross-section, and may have an outer cross-sectional dimension of from about 0.001 inches to about 0.009 inches, of from about 0.002 inches to about 0.008 inches, or from about 0.003 inches to about 0.007 inches. In some embodiments, the coil 120a may have an inner cross-sectional dimension that is no greater than 0.006 inches, and in some embodiments no greater than 0.005 inches, and in some embodiments no greater than 0.004 inches.

Referring again to FIGS. 1A and 1C, the mesh 100 of the present technology has a low-profile state (not shown) for intravascular delivery through a catheter (e.g., a microcatheter) to the aneurysm and a deployed state in which the mesh 100 is configured to be positioned across the neck of the aneurysm. Once implanted, the mesh 100 provides substantially full coverage of the neck. To achieve such coverage, the mesh 100 may have a predetermined three-dimensional shape that is generally concave and defines a generally constant radius of curvature such that the shape of the mesh 100 conforms to the curvature of the aneurysm wall near the neck.

The mesh 100 may have a proximal end portion 100a, a distal end portion 100b, a body portion 136 extending between the proximal and distal end portions 100a, 100b, and a length measured along the longitudinal axis L of the device 10 between the distal joint 109 and the intermediate joint 110. The mesh 100 may have opposing side edges 134 extending longitudinally along its length and a width w extending between its side edges 134. In some embodiments, such as that shown in FIGS. 1A-1C, the width w may be generally constant along the body portion 136 and taper proximally and distally at its proximal and distal end portions 100a, 100b, respectively. In such embodiments, the side edges 134 may be generally parallel to one another at least along the body portion 136. In some embodiments, the width w may increase and/or decrease between the tapered portions. For example, in some embodiments, the width w of the mesh 100 may increase from the distal end portion 100b in a proximal direction, then decrease as it tapers down to the proximal end portion 100a such that the mesh 100 has a petal-like shape. In some embodiments, the mesh 100 does not have any tapered portions and maintains a generally constant width along its entire length. In some embodiments, the mesh 100 has a length that is about 10 to about 100 mm when the mesh is in an unconstrained state.

Figure 2B:
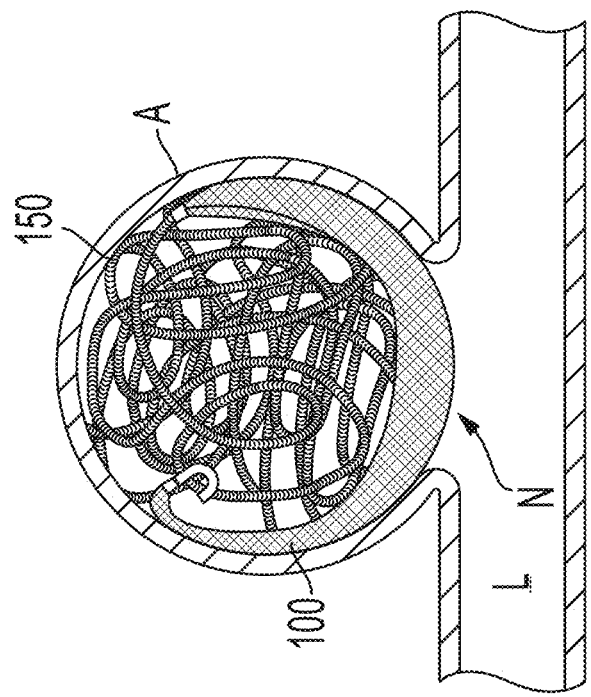
FIGS. 2A and 2B illustrate a method of deploying an occlusive device of the present technology.

The mesh 100 may be heat set to form an elongated ribbon that is curved along both its width w and its length, as best shown in cross-section of the mesh 100 in FIG. 1B. The mesh 100 may thus include a concave surface 130 and a convex surface 132. When the device 10 is positioned at an aneurysm, the mesh 100 may be positioned across the neck of the aneurysm such that the concave surface 130 faces the aneurysm cavity and the convex surface 132 faces the parent vessel with the coil 150 positioned between the concave surface 130 and the dome of the aneurysm (as shown in FIG. 2B).

As best shown in the cross-sectional view of FIG. 1B, the mesh 100 may be formed of a flattened, tubular braid such that the mesh comprises two mesh layers that meet at folds at the side edges 134. For example, in some embodiments, the mesh 100 may be formed of a tubular braid that has been heat set after being wrapped around a portion of a spherical mold. For example, in one method of manufacture in accordance with the present technology, the tubular braid is wrapped less than 360 degrees around a spherical mold having a radius of curvature equivalent to the radius of curvature of the resulting mesh 100. As the tubular braid is wrapped around the spherical mold, opposing portions of the tubular sidewall are pressed toward one another along the length of the tubular braid, thereby "flattening" the tubular braid while conforming the braid to the curvature of the spherical mold. The braid can be wrapped no more than about 180 degrees, no more than about 190 degrees, no more than about 200 degrees, no more than about 210 degrees, no more than about 220 degrees, no more than about 225 degrees, no more than about 230 degrees, no more than about 235 degrees, no more than about 240 degrees, no more than about 245 degrees, no more than about 250 degrees, no more than about 255 degrees, no more than about 260 degrees, no more than about 265 degrees, no more than about 270 degrees, no more than about 275 degrees, no more than about 280 degrees, no more than about 285 degrees, no more than about 290 degrees, no more than about 295 degrees, or no more than about 300 degrees around the mold. As such, when the mesh 100 is deployed within an aneurysm, the mesh 100 generally curves around an axis A1 (see FIG. 2A) to generally the same degree as the mesh 100 was wrapped around the mold. Because of this, in many embodiments the proximal end 100a of the mesh 100 does not meet the distal end 100b (for example, as shown and described in FIGS. 2C and 2D).

It may be beneficial to have an "open" curved structure (i.e., mesh wraps less than 360 degrees around the aneurysm and does not overlap), as the open configuration is more readily filled with coils and reduces the chance of compartmentalization of the embolic filler (such as coil 150 and/or subsequently placed coils) between the mesh and the aneurysm wall. An example of an overlapping endosaccular design is the Medina Embolic Device (MED; Medtronic, Irvine, Calif.), which is a three-dimensional layered structure created from a flattened tubular braid. When allowed to self-expand, the mesh contains multiple leaflets resembling petals that provide density and flow diversion. However, the multi-petal structure did not adequately isolate/prevent endosaccular inflow/outflow and the aneurysm would remain active. Moreover, the petals isolated/excluded the microcatheter from the cavity of the aneurysm and prevented adequate filling with other petals or coils (compartmentalization). The petals would trap the microcatheter against the wall of the aneurysm or sandwich it between adjacent petals. Even though the microcatheter tip was still within the aneurysm, subsequent petals or coils could not access the aneurysm cavity and instead became compartmentalized. The non-overlapping embodiments of the present technology avoid such drawbacks.

An open structure mesh structure also allows for a decrease in the overall length of the mesh 100, thus making the occlusive device 10 easier to deliver through a catheter to the aneurysm, and also frees up some of the length of the device 10 to be used for the coil 150 (which has significantly less friction with the catheter wall and is easier to push). The "open" curved mesh structure also self-anchors at the aneurysm neck and forms a basket-like structure that captures the coil 150 between the aneurysm dome and the neck.

Figure 2A:
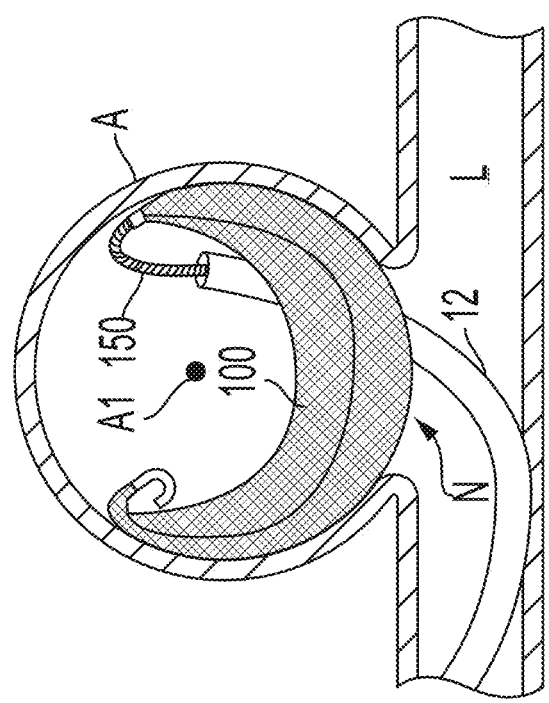
Figure 2C:
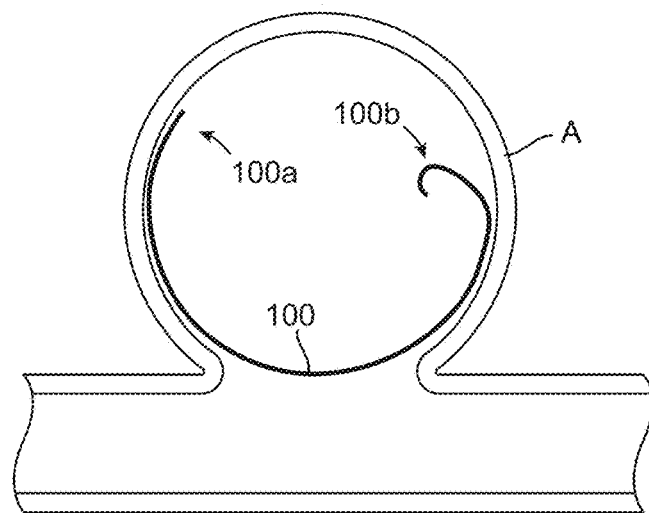
FIGS. 2C-2E show different meshes of the present technology as deployed within an aneurysm.
Figure 2D:
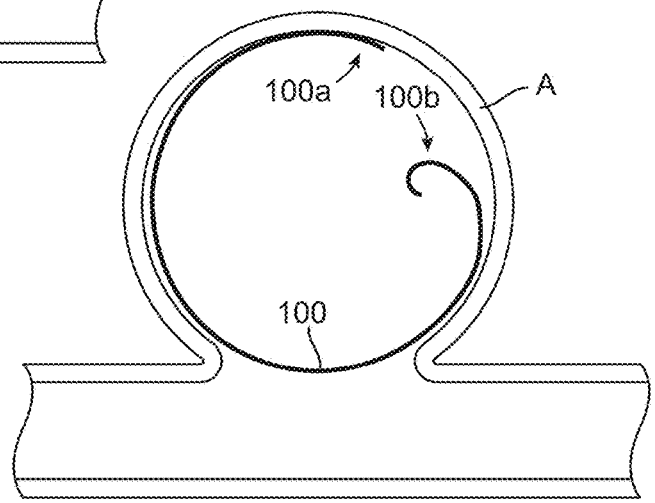
Figure 2E:
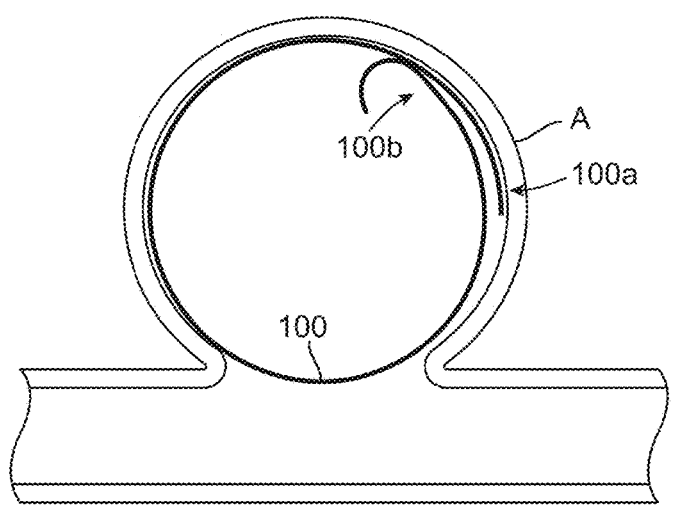

In other embodiments, the mesh 100 may wrap around the axis A1 360 degrees or more such that it meets or overlaps itself (i.e., the proximal end 100a extends circumferentially beyond the distal end 100b) along at least a portion of the length of the mesh 100, thereby forming a closed loop (as shown in FIG. 2E).

Depending on the geometry of the aneurysm to be treated, the mesh 100 may have other shapes or configurations and may be formed in a similar manner on molds having other shapes or sizes, such as non-spherical shapes, cylinders, hemispheres, polyhedrons (e.g., cuboids, tetrahedrons (e.g. pyramids), octahedrons, prisms, etc.), prolate spheroids, oblate spheroids, plates (e.g., discs, polygonal plates), bowls, non-spherical surfaces of revolution (e.g., toruses, cones, cylinders, or other shapes rotated about a center point or a coplanar axis), and combinations thereof.

In those embodiments where the mesh 100 comprises a braid, such as that shown in FIGS. 1A-1C, the braid may be formed of a plurality of wires, at least some of which (e.g., 25% of the wires, 50% of the wires, 80% of the wires, 100% of the wires, etc.) are made of one or more shape memory and/or superelastic materials (e.g., Nitinol). The braid may have, for example, 44 to about 144 wires, such as 64 or 72 wires. Some or all of the wires may have a diameter between about 0.0010 inches and about 0.0012 inches, about 0.0010 inches, about 0.0011 inches, 0.0012 inches (at least prior to etching). In some embodiments, some or all of the wires may be drawn-filled tubes ("DFT") having a radiopaque core (e.g., platinum) surrounded by a shape memory alloy and/or superelastic alloy (e.g., Nitinol, cobalt chromium, etc.). All or a portion of the length of some or all of the wires may have one or more coatings or surface treatments. For example, some or all of the wires may have a lubricious coating or treatment that reduces the delivery force of the mesh 100 as the device 10 is advanced through the delivery catheter. In some embodiments, the coating may be relatively hydrophilic, such as a phosphorocholine compound. Additionally or alternatively, some or all of the wires may have a coating or treatment (the same as the lubricious coating, or a different coating) that enhances blood compatibility and reduces the thrombogenic surface activity of the braid. In these and other embodiments, at least a portion of the wires can be made of other suitable materials.

The coil 150 of the present technology may be formed of one or more wires wound in a helical fashion about an axis to form an elongated tubular member. The wire(s) forming the coil 150 may be circular, square, or rectangular in cross-section, and may have a cross-sectional dimension of from about 0.001 inches to about 0.003 inches, or of from about 0.0015 inches to about 0.0025 inches. In some embodiments, the wire(s) forming the coil 150 has a cross-sectional dimension no greater than 0.003 inches, no greater than 0.0025 inches, or no greater than 0.002 inches. The coil 150 may be circular, square, or rectangular in cross-section, and may have a cross-sectional dimension of from about 0.01 inches to about 0.02 inches, of from about 0.012 inches to about 0.018 inches, or from about 0.014 inches to about 0.016 inches. In some embodiments, the coil 150 may have a cross-sectional dimension that is no greater than 0.0145 inches, and in some embodiments no greater than 0.0140 inches.

The coil 150 may have a length along the longitudinal axis L of the device 10 that is significantly longer than that of the mesh 100. For example, the coil 150 may have a length of about 2 cm to about 30 cm, about 3 cm to about 25 cm, about 4 cm to about 20 cm. In some embodiments, the length of the coil 150 may depend on the size of the aneurysm being treated. For example: for an aneurysm 4 mm in diameter or less, the coil 150 may have a length of about 6 cm; for an aneurysm 5 mm in diameter or less, the coil 150 may have a length of about 8 cm; for an aneurysm 6 mm in diameter or less, the coil 150 may have a length of about 15 cm; for an aneurysm 7 mm in diameter or less, the coil 150 may have a length of about 15 cm; for an aneurysm 8 mm in diameter or less, the coil 150 may have a length of about 20 cm; and, for an aneurysm 9 mm in diameter or less, the coil 150 may have a length of about 20 cm.

The coil 150 may be made from metals, alloys, polymers, shape memory materials (e.g., Nitinol), platinum, rhodium, palladium, tungsten, gold, silver, cobalt-chromium, platinum tungsten, and/or various alloys of these materials. In some embodiments, the coil 150 may be heat set to form a tertiary structure (i.e., a pre-determined three-dimensional structure) when in a deployed state. For example, the coil 150 may have a preset tertiary structure that biases the coil into a bundled or more globular state that facilitates positioning of the coil 150 between the deployed mesh and the aneurysm wall. In some embodiments, the coil 150 does not have a tertiary structure.

Additionally or alternatively, the coil 150 may optionally include a loop 152 (see FIG. 1A) at its distal portion 150b adjacent the intermediate joint 110. The loop 152 may be configured to absorb the release of energy that occurs when a proximal end 100a of the mesh clears the distal end of the delivery catheter. As the device 10 is pushed from the microcatheter, the mesh 100 experiences greater friction/ resistance to the forward motion and the coil 150 compresses to absorb this energy. Release of the distal end of the coil 150 from the microcatheter releases the stored energy, which can result in a "kick-back" or "lunging" from the coil 150, which can displace the microcatheter from the aneurysm cavity. To prevent this uncontrolled release of energy, the coil 150 may optionally include the loop 152 at its distal end 150b to neutralize any sudden coil movement that may occur as a result of the distal end 150b of the coil 150 being released from the microcatheter. While only a single loop is shown in FIG. 1A, it will be appreciated that the coil 150 may have multiple loops and/or different configurations of loops along its length.

Additional thrombogenic elements (e.g., particles, radial filaments, polymer fibers etc.) may be attached to at least a portion of the coil 150 using any suitable binding technique; e.g., by tying or otherwise adhering them to the coil 150.

In some embodiments, the stiffness of the mesh 100 and/or occlusive device 10 may be generally constant along the longitudinal axis L, and in some embodiments, the stiffness of the mesh 100 and/or occlusive device 10 varies along the longitudinal axis L. For example, the stiffness of one or more portions of the mesh 100 can be different than other portions of the mesh 100 by varying one or more parameters such as the materials, porosity, thickness, wire size, braid count (if applicable), and/or braid pitch (if applicable). Likewise, the stiffness of one or more portions of the coil 150 can be different than other portions of the coil 150 by varying one or more parameters along the length of the coil, such as wire size, pitch, and/or cross-sectional dimension (e.g., diameter). Moreover, in some embodiments the mesh 100 may be generally stiffer than the coil 150 so that the mesh 100 better frames and anchors the device 10 within the aneurysm, and the coil 150 may be flexible and/or malleable enough to pack and fill the aneurysmal sac.

The mesh 100 and the coil 150 may be coupled end-to-end at the intermediate joint 110 which is configured to flex, bend, rotate, twist, or otherwise articulate such that the distal end 150b of the coil 150 may be positioned at an angle relative to the proximal end 100a of the mesh 100. Likewise, the mesh 100 and the lead-in member 106 may be coupled end-to-end at the distal joint 109 which is configured to flex, bend, rotate, twist, or otherwise articulate such that the distal end 100b of the mesh 100 may be positioned at an angle relative to the proximal end 100a of the lead-in member 106. It will be appreciated that joint construction on any intravascular device that must navigate the tortuous cerebral vasculature must be sufficiently flexible. If the joint is too long or too stiff, the device will not be able to navigate sharp turns and cross the neck of small aneurysms. Bulky or stiff joints also cause increased friction with the microcatheter, which can lead to "lunging" of the microcatheter, mesh, and/or coil during delivery. The joints of the present technology are configured to provide improved flexibility without compromising the security of the connection.

Figure 1E:
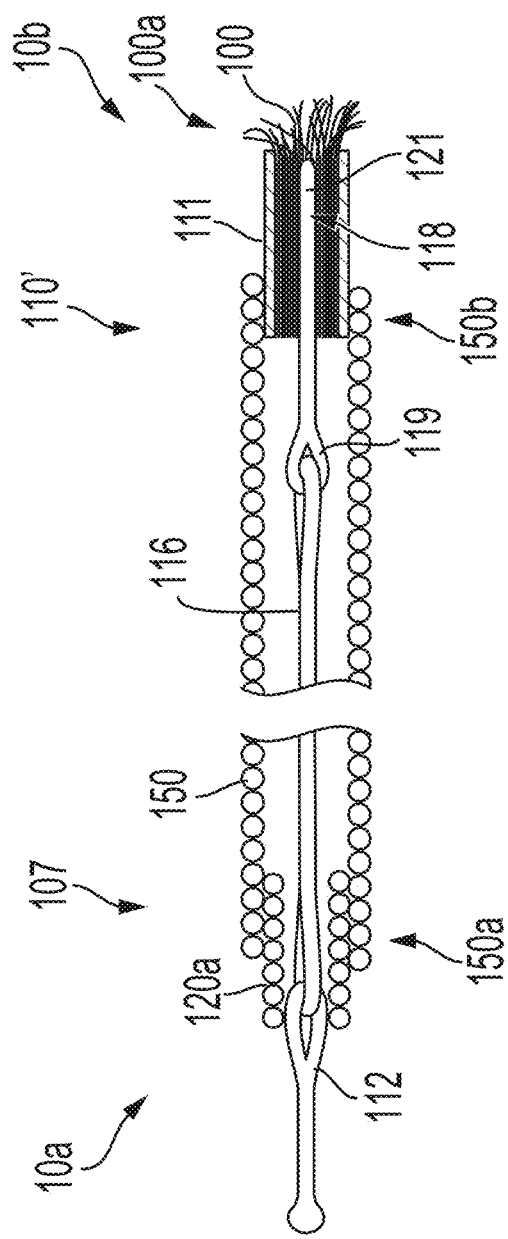
FIG. 1E is a schematic representation of attachment regions of the occlusive devices of the present technology.

As shown in FIG. 1D, in some embodiments the joint 110 may comprise a connector, such as band 111, surrounding a proximal end of the mesh 100a, the distal portion of the intermediate member 116, a connector 118 extending through at least a portion of the band 111, and a securing element 120b extending between the coil 150 and the band 111. In some embodiments, the proximal end of the band 111 is spaced apart from a distal end of the coil 150 and the securing element 120b spans the gap. In some embodiments, the band 111 is in contact with and/or co-extensive with a distal end of the coil 150 (for example as shown in FIG. 1E, detailed below).

The intermediate member 116 may be configured to extend through the coil 150 and attach to either end of the coil 150 to prevent overstretching of the coil 150. In some embodiments, the intermediate member 116 may be a flexible filament, such as a suture strand. The suture strand may be formed of polyethylene terephthalate (PET) monofilament, polypropylene (PP) monofilament, or other suitable, stretch-resistant materials.

Referring still to FIG. 1D, the connector 118 may include a coupling region 119 and an extension portion 121 extending from the coupling region 119 and configured to be secured within the band 111. The band 111 may be crimped down over the extension portion 121 and the filaments forming the proximal end of the mesh 100, thereby securing the mesh 100 to the connector 118. In some embodiments, the connector 118 is a wire, such as a platinum wire, that is folded back on itself then twisted such that the folded back portion forms the coupling region 119 and the twisted portion forms the extension portion 121.

The coupling between the intermediate member 116 and connector 118 may be surrounded by the securing element 120b to secure the connection. The securing element 120b may have a proximal portion surrounding by a distal end of the coil 150, and a distal portion surrounded by a proximal end of the mesh 100 and/or band 111. In other embodiments, the proximal end of the securing element 120b may be adjacent or spaced apart from the distal end of the coil 150 and/or the distal end of the securing element 120b may be adjacent to or spaced apart from the proximal end of the mesh 100 and/or band 111.

In some embodiments, such as that shown in FIG. 1D, the securing element 120b may be a coil formed of one or more wires wound in a helical fashion about an axis to form an elongated tubular member. The tubular member may have a generally constant cross-sectional diameter along its length, or at least a portion of the tubular may taper in a proximal or distal direction. The wire(s) forming the coil 120b may be circular, square, or rectangular in cross-section, and may have a cross-sectional dimension of from about 0.001 inches to about 0.003 inches, or of from about 0.0015 inches to about 0.0025 inches. In some embodiments, the wire(s) forming the coil 120b has a cross-sectional dimension no greater than 0.003 inches, no greater than 0.0025 inches, or no greater than 0.002 inches. The coil 120b may be circular, square, or rectangular in cross-section, and may have an outer cross-sectional dimension of from about 0.004 inches to about 0.012 inches, of from about 0.005 inches to about 0.01 inches, or from about 0.006 inches to about 0.01 inches. In some embodiments, the coil 120b may have an outer cross-sectional dimension that is no greater than 0.01 inches, and in some embodiments no greater than 0.009 inches. The coil 120b may be circular, square, or rectangular in cross-section, and may have an outer cross-sectional dimension of from about 0.001 inches to about 0.012 inches, of from about 0.002 inches to about 0.008 inches, or from about 0.003 inches to about 0.007 inches. In some embodiments, the coil 120b may have an inner cross-sectional dimension that is no greater than 0.008 inches, and in some embodiments no greater than 0.006 inches, and in some embodiments no greater than 0.004 inches.

In some aspects of the technology, one or both of the securing element 120a and/or securing element 120b may have a cross-sectional dimension (e.g., diameter) less than a cross-sectional dimension (e.g., diameter) of the coil 150, and/or one or both of the securing element 120a and/or the securing element 120b have a length that is less than a length of the coil 150. Moreover, the intermediate joint 110 between the coil 150 and the mesh 100 may be used with any of the occlusive device embodiments described herein. For example, the connection between the coil 150 and the mesh 300 of occlusive device 30 may comprise intermediate joint 110, the connection between the coil 150 and the mesh 800 may comprise intermediate joint 110, the connection between the coil 150 and the mesh 1000 may comprise intermediate joint 110, etc.

FIG. 1E illustrates another example of an intermediate joint 110' configured for use with the occlusive devices of the present technology to couple one or more coils (such as coil 150) to one or more occlusive meshes disclosed herein. As shown in FIG. 1E, the intermediate joint 110' may be configured to flex, bend, twist, rotate, or otherwise articulate such that the distal end 150b of the coil 150 may move and be positioned at an angle relative to the proximal end 100a of the mesh 100. Similar to intermediate joint 110, intermediate joint 110' may comprise the distal end portion 150b of the coil 150, a proximal end portion of the band 111, and at least a portion of connector 118. Unlike intermediate joint 110, however, intermediate joint 110' does not include a distal securing element 120b and instead the distal end portion of the coil 150b extends over and surrounds a proximal end portion of the band 111. Thus, at least at the joint 110', in some embodiments the coil 150 may have a greater diameter than that of the band 111. In some embodiments, the band 111 and proximal portion of the mesh 100a within may be crimped to a smaller diameter (for example, 50% of its diameter in the configuration of FIG. 1D), then swaged to smoothen any edges that may catch on the catheter lumen or distal opening during delivery. The coil 150 may then be welded to the band 111 to secure the connection. The positioning of the coil 150 over the band 111 allows for the removal of the distal securing element 120b, which reduces the length and diameter of the joint, thereby making the joint 110' more flexible than joint 110'. For example, the straight portion of the joint 110' may be less than or equal to 2 mm, less than or equal to 1.5 mm, or less than or equal to 1 mm.

Moreover, as shown in FIG. 1E, the coupling region between the distal end portion of the intermediate member 116 and the coupling region 119 of the connector 118 may be disposed within the lumen of the coil 150. In some embodiments, the coupling region between the intermediate member 116 and the coupling region 119 may be disposed within the band 111.

Although intermediate joint 110' is described herein with reference to occlusive device 10 and mesh 100, intermediate joint 110' may be used with any of the occlusive devices of the present technology. For example, occlusive device 30 may include intermediate joint 110' between coil 150 and mesh 300, occlusive device 80 may include intermediate joint 110' between coil 150 and mesh 800, occlusive device 101 may include intermediate joint 110' between coil 150 and mesh 1000, occlusive device 120 may include intermediate joint 110' between coil 150 and mesh 1200, etc.

Moreover, the joints or coupling means between the coils and meshes disclosed herein may have configurations other than those shown and described in FIGS. 1D and 1E. For example, in some embodiments the distal end portion 150b of the coil 150 may be disposed within the lumen of the band 111. In those embodiments where the distal end portion 150b of the coil 150 and the proximal end portion 100a of the mesh 100 (and/or a component thereof, such as band 111) are co-extensive with one another, the joint may include an additional securing and/or stabilization member (such as securing element 120a or securing element 120b) that extends between the overlapping coil and mesh.

Although the foregoing embodiments are described with respect to a single continuous mesh and a single coil, these and other embodiments of the occlusive device 10 may include more than one mesh and/or more than one coil. The mesh(es) and coil(s) may be arranged end-to-end (as described above), or one or more of the mesh(es) or coil(s) may be arranged in parallel or otherwise overlapping along at least a portion of their lengths. The mesh(es) and coil(s) may be alternating and/or the occlusive device 10 may include two or more consecutive mesh(es) and/or two or more consecutive coil(s).

FIGS. 2A and 2B illustrate a method of deploying the occlusive device 10 in accordance with the present technology. In use, the occlusive device 10 may be intravascularly delivered to a location within a blood vessel lumen L adjacent a target aneurysm A in a low-profile configuration (not shown) within a delivery catheter 12. The distal portion of the delivery catheter 12 is then advanced through the neck N of the aneurysm A to an interior region of the aneurysm A. As shown in FIG. 2A, the occlusive device 10 is then deployed by pushing the occlusive device 10 distally through the distal opening of the delivery catheter 12 towards the inner wall of the aneurysm A. The mesh 100 exits the delivery catheter 12 first and, as it's deployed, the mesh 100 curves around the curved inner surface of the aneurysm A, crosses the neck N, and continues to curve around the other side of the aneurysm A. As shown in FIG. 2B, the coil 150 deploys next and fills space within the aneurysmal sac. Then, with the tip of the delivery catheter still within the aneurysm sac, the occlusive device 10 may be detached from the delivery member (such as a pusher member) via one or more of the detachment mechanisms described elsewhere herein.

In some cases, the physician may choose to deliver additional coils or embolic material (such as a liquid embolic) to the aneurysm. In these scenarios, the physician may withdraw the pusher member from the delivery catheter and, while maintaining the tip of the delivery catheter within the aneurysm sac (beyond the mesh positioned across the neck), the physician may push the additional embolic material through the delivery catheter and into the aneurysm.

In some embodiments, the mesh 100 may have a length such that, when deployed within the aneurysm A, the mesh 100 does not wrap around the entire 360 degrees of the aneurysm sac. As shown in FIG. 2C, in such embodiments the proximal and distal ends 100a, 100b of the mesh 100 do not overlap. The mesh 100 be configured to wrap around less than 270 degrees of the aneurysm. According to some embodiments, the mesh 100 may be configured to wrap around more than 270 degrees but less than 360 degrees, as shown in FIG. 2D. In some embodiments, the mesh 100 may be configured to wrap around greater than 360 degrees of the aneurysm such that the distal and proximal ends 100b, 100a overlap, as shown in FIG. 2E. In many cases, however, it may be beneficial to utilize a mesh configured to wrap around less than 360 degrees to avoid any overlapping portions of the mesh. Such overlapping portions can trap the microcatheter against the mesh and the wall such that the coil gets delivered to an exterior portion of the wrapped braid rather than the desired interior region. One or more of the meshes 300, 800, 1000, and 1200 described below may also be configured to wrap around less than 270 degrees or less than 360 degrees of the aneurysm when positioned therein.

The methods of the present technology may be performed under fluoroscopy such that the radiopaque portions of the device 10 may be visualized by the physician to ensure proper neck coverage. In those embodiments where the coil 150 is radiopaque (for example, when the coil 150 is a platinum coil), should the physician observe the coil 150 protruding from the neck N during deployment, the physician may pull the occlusive device 10 at least partially back into the delivery catheter 12, reposition, and redeploy in a new position.

As previously mentioned, embolic coils can be very effective at filling space within an aneurysm cavity. One of the challenges in treating aneurysms with embolic coils, however, is the associated risk of the coils prolapsing through the neck of the aneurysm into the parent vessel. Current solutions to this problem include positioning an occlusive device over the neck of the aneurysm to prevent the coils from migrating through the neck. However, despite these recent advances, wide-necked aneurysms (defined by neck diameters greater than 4 mm or dome-to-neck ratios less than 2) remain difficult to treat. Because of the wide neck, intrasaccular neck-covering devices have less aneurysm wall to grip, making these devices less stable and thus more susceptible to bulging into the parent vessel in response to the outward pressure (i.e., towards the parent vessel) exerted by the packed coils. The occlusive devices of the present technology address these challenges by providing a mesh structure configured to be positioned over the neck of an aneurysm with a novel shape that imparts increased longitudinal and/or lateral rigidity to the mesh so that the mesh can resist bulging into the parent vessel under pressure from the coils.

Figure 3A:
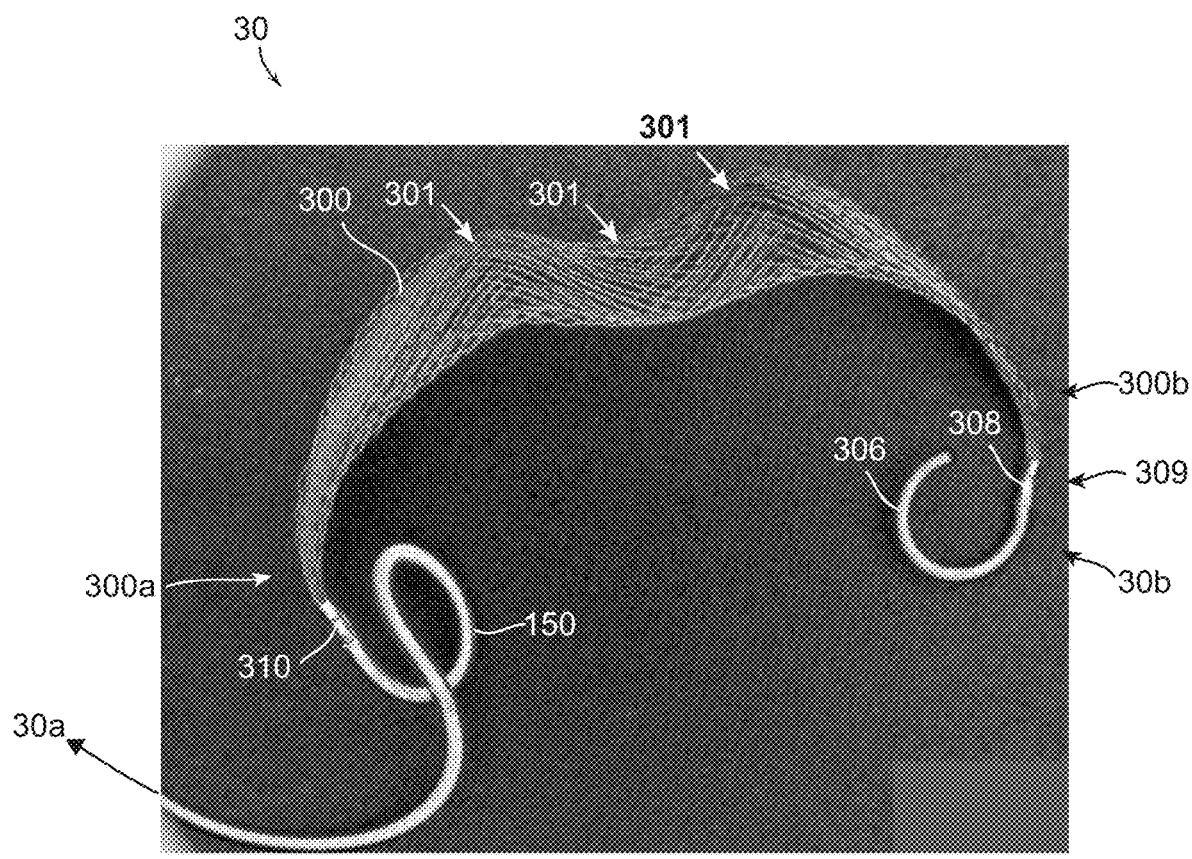
FIG. 3A shows a portion of an occlusive device in an unconstrained state outside of an aneurysm according to some embodiments of the present technology.
Figure 3B:
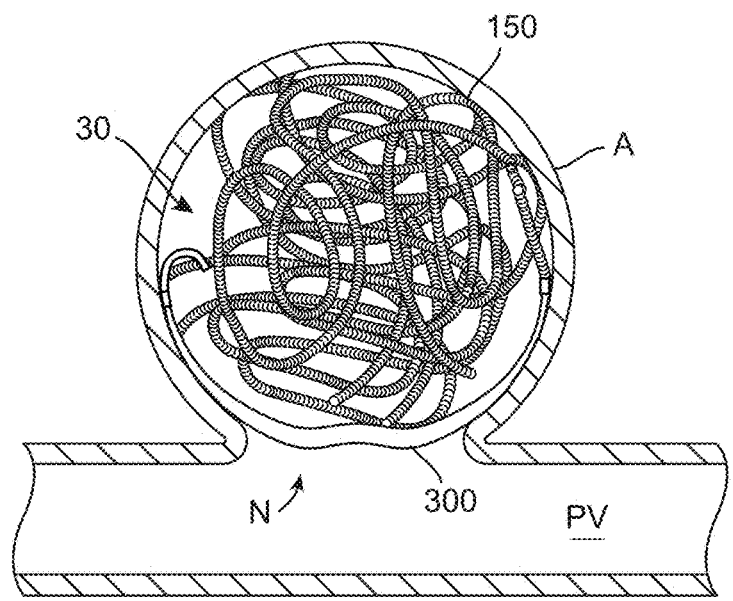
FIG. 3B shows the occlusive device of FIG. 3A positioned within an aneurysm of a human patient.

FIG. 3A, for example, depicts a portion of an occlusive device 30 (or "device 30") in accordance with embodiments of the present technology, shown in an expanded, unconstrained state. FIG. 3B shows the occlusive device 30 deployed in an aneurysm A of a human patient. The occlusive device 30 may comprise a mesh 300 configured to be positioned across the neck N of the aneurysm and a coil 150 coupled to and extending away from an end portion of the mesh 300. As shown in FIG. 3B, the coil 150 is configured to be deployed between the mesh 300 and the dome of the aneurysm A to fill space within the aneurysm cavity. As such, the mesh 300 and the coil 150 occupy substantially separate regions of the aneurysm cavity once implanted. In some embodiments, the occlusive device 30 comprises only the mesh 300, and an embolic material (such as an embolization coil) may be delivered to the aneurysm separately. As described in greater detail below, the mesh 300 may have one or more laterally-extending undulations 301 along its length that resist and redistribute the outwardly-directed forces exerted by the coil 150 on the neck-covering portion of the mesh 300.

The occlusive device 30 may have several components that are generally similar to the components of occlusive device 10. For example, the occlusive device 30 may include a lead-in member 306 similar to lead-in member 106 and a distal joint 309 similar to distal joint 109. The mesh 300 may be coupled to the coil 150 via a joint 310 that is generally similar to intermediate joint 110 or intermediate joint 110'. The proximal portion of the occlusive device 30 may include a detach element (not shown) generally similar to detach element 112 that is configured to be detachably coupled to a delivery device. In some embodiments, the occlusive device 30 may not include one or more of the lead-in member 306, the distal joint 309, the intermediate joint 310, and the detach element.

FIGS. 4A-4C show different views of portions of the occlusive device 30 in an unconstrained, expanded state with the mesh 300 illustrated as an opaque, non-porous surface so the contour of the mesh 300 may be better appreciated without being obfuscated by the wires of the mesh 300. FIG. 4A is an isometric view of a portion of the occlusive device 30, FIG. 4B is an end view of the mesh 300, and FIG. 4C is a side view of the mesh. As shown, the mesh 300 may have a proximal end portion 300a proximate the joint 310, a distal end portion 300b proximate the distal joint 309, and a length measured along the longitudinal axis L of the mesh 300 between the joint 310 and the distal joint 309. The mesh 300 may have opposing side edges 312a and 312b (collectively, "side edges 312") extending longitudinally along its length and a circumferential width $C_1$ (FIG. 4B) extending between its side edges 312. The mesh 300 may be curved along both its longitudinal dimension (see FIGS. 4A and 4B) and its width dimension (see FIG. 4B). The radius of curvature along the width may be constant or may vary, and the radius of curvature along the length may be constant or may vary.

The mesh 300 may further include a first side 315a, a second side 315b opposite the first side 315a, and a thickness t (FIG. 4A) measured between the first and second sides 315a and 315b. When the occlusive device 30 is positioned within an aneurysm, the first side 315a is configured to face towards the parent vessel PV (FIG. 3B) and the second side 315b is configured to face the aneurysm cavity. The mesh 300 may have a generally constant thickness t along its length such that the contour of the first side 315a follows the contour of the second side 315b (and vice versa). In some embodiments, the mesh 300 may have a thickness t that varies along all or a portion of its length. In particular embodiments, the mesh 300 does not define an interior volume in the unconstrained, expanded state and/or in the deployed state.

As shown, the mesh 300 may include proximal and distal tapered portions 316a and 316b (collectively, tapered portions 316) along which the width $C_1$ tapers towards the joint 310 and the distal joint 309, respectively. In some embodiments, the side edges 312 may extend at an angle relative to one another along the entire length of the mesh 300 between the tapered portions 316 such that the mesh 300 has a petal- or -orange-peel shape. In some embodiments, the side edges 312 may be parallel to one another along at least a portion of the length of the mesh 300 between the tapered portions 316 (for example as shown in FIG. 1C). As such, in these and other embodiments, the mesh 300 may have a width $C_1$ that is generally constant along at least a portion of the length of the mesh 300. In some embodiments, the mesh 300 does not have any tapered portions and maintains a generally constant width $C_1$ along its entire length.

The mesh 300 may include a plurality of laterally-extending undulations 330, 331, 332 (not shown in FIG. 4B) disposed along its longitudinal axis L, each corresponding to an inflection region along the curved body the mesh 300 at which the shape of the mesh 300 changes from convex to concave (or vice versa). Each of the undulations 330, 331, 332 may extend between the first and second lateral side edges 312a and 312b such that the undulations extend across the entire width $C_1$ of the mesh 300. In some embodiments, one, some, or all of the undulations may extend across less than the entire width $C_1$ of the mesh 300. Although only three inflection regions are depicted in FIGS. 4A-4C, in some embodiments the mesh 300 may include more or fewer inflection regions (e.g., two inflection regions, four inflection regions, five inflection regions, etc.).

In the embodiment shown in FIGS. 4A-4C, the first side 315a of the mesh 300 includes first and second peaks 330a and 332a separated by a valley 331a. The mesh 300 is configured to be positioned over the neck of an aneurysm such that the first and second peaks 330a and 332a are convex towards the parent vessel while the valley 331a is concave towards the parent vessel. The second side 315b of the mesh 300 includes first and second valleys 330b and 332b separated by a peak 331b. Because the thickness t of the mesh 300 is generally constant along the length of the mesh 300 (at least in the present example), the axial locations of the first and second peaks 330a and 332a correspond to the axial locations of the first and second valleys 330b and 332b, and the axial location of the valley 331a corresponds to the axial location of the peak 331b. The mesh 300 is configured to be positioned over the neck of an aneurysm such that the first and second valleys 330b and 332b are concave towards the aneurysm cavity while the peak 331b is convex towards the aneurysm cavity.

Figure 5A:
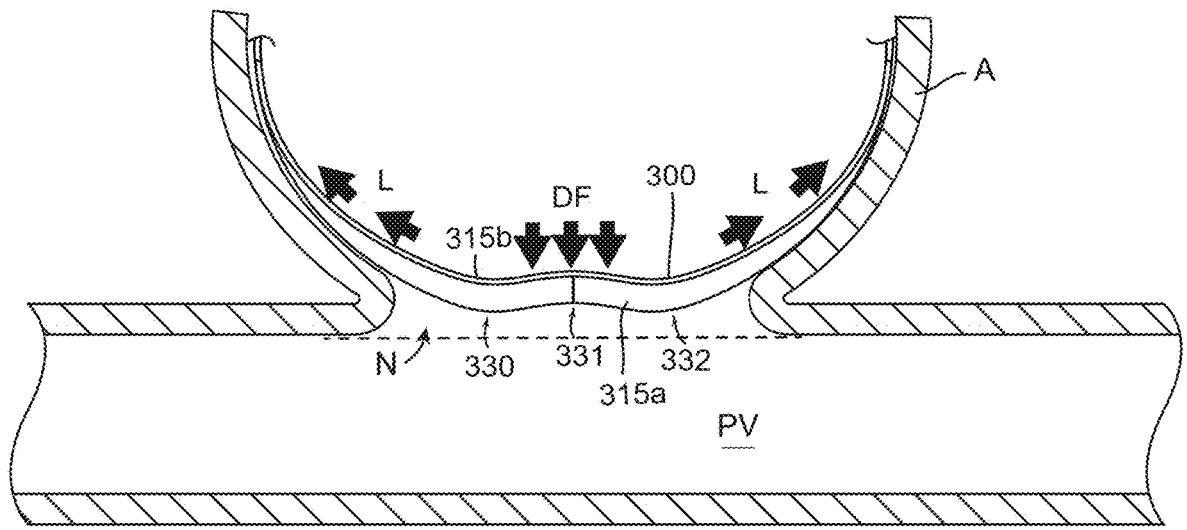
FIGS. 5A and 5B are side views of the mesh of the occlusive device of FIGS. 4A-4C showing an example response of the mesh to deformation forces in accordance with the present technology.
Figure 5B:
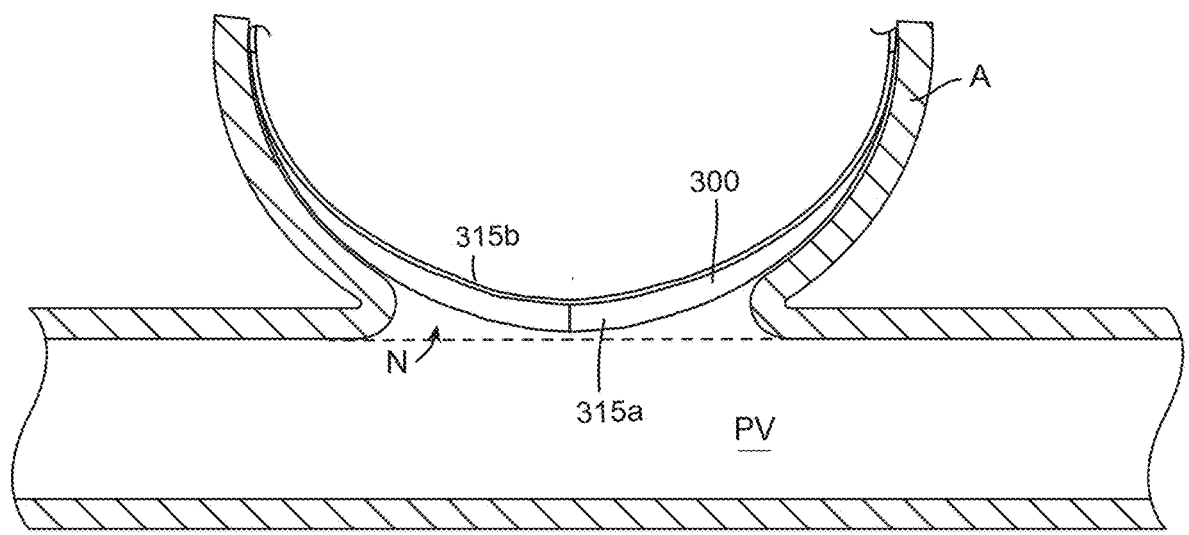

As depicted schematically in FIGS. 5A and 5B, when the mesh 300 is positioned over the neck N of an aneurysm A and the coil 150 (or other embolic material) exerts an outwardly-directed force DF (i.e., towards the parent vessel V) on the portion of the mesh 300 spanning the neck N, the convex or arched portion 331 at the second side 315b of the mesh 300 absorbs the force DF and redistributes the force longitudinally and upwardly along the tapered portions 316 of the mesh 300 (indicated by arrows L). As such, in response to the outwardly-directed forces, the curvature of the inflection regions 330, 331, and 332 lessen and the tissue-engaging wings of the mesh 300 get pushed farther up and around an inner surface of the aneurysm wall. After being deformed, one or both of the first and second end portions 300a and 300b may be positioned at an aneurysm wall height that is greater than the height where each end portion 300a, 300b was positioned prior to the deformation. This way, more of the mesh 300 engages the inner surface of the aneurysm wall, which further secures and stabilizes the mesh 300 within the aneurysm A. Even more importantly, the deformation of the mesh 300 does not break the plane of the aneurysm neck N and thus does not protrude into the parent vessel PV. Accordingly, the meshes of the present technology are configured to absorb and deform in response to outwardly-directed forces without causing a prolapse of the mesh 300 into the parent vessel PV.

Figure 6:
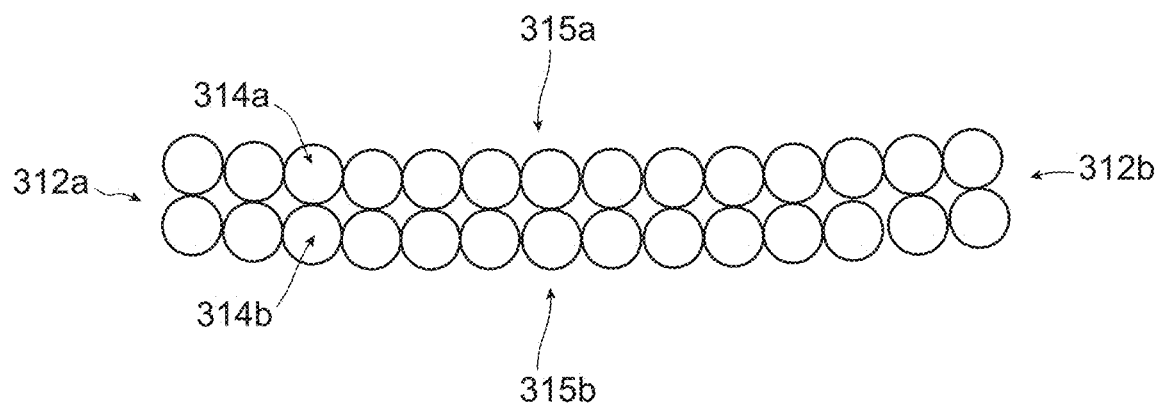
FIG. 6 is an enlarged cross-sectional view of a portion of the mesh shown in FIG. 4A taken along line 6-6.

In some embodiments, the mesh 300 may be formed of a stent, a braid, a lattice, a weave, a laser-cut sheet, and/or any other suitable porous structure. In particular embodiments, including that shown in FIG. 3A, the mesh 300 may be formed of a tubular braid that has been flattened along its longitudinal axis such that opposing sidewalls of the tubular braid are urged toward one another. The resulting mesh structure is thus formed of two braided layers 314a, 314b that meet at folds at the side edges 312a, 312b of the mesh 300, as depicted in the cross-sectional view of FIG. 6. The first layer 314a may comprise the braided wires at the first side 312a of the mesh 300 and the second layer 314b may comprise the braided wires at the second side 312b of the mesh 300.

In some embodiments, the mesh 300 may be formed of a tubular braid that has been heat set after being wrapped around a portion of a spherical mold. For example, in one method of manufacture in accordance with the present technology, the tubular braid is wrapped less than 360 degrees around a spherical mold having a radius of curvature equivalent to the radius of curvature of the resulting mesh 300. As the tubular braid is wrapped around the spherical mold, opposing portions of the tubular sidewall are pressed toward one another along the length of the tubular braid, thereby "flattening" the tubular braid while conforming the braid to the curvature of the spherical mold. The braid can be wrapped no more than about 180 degrees, no more than about 190 degrees, no more than about 200 degrees, no more than about 210 degrees, no more than about 220 degrees, no more than about 225 degrees, no more than about 230 degrees, no more than about 235 degrees, no more than about 240 degrees, no more than about 245 degrees, no more than about 250 degrees, no more than about 255 degrees, no more than about 260 degrees, no more than about 265 degrees, no more than about 270 degrees, no more than about 275 degrees, no more than about 280 degrees, no more than about 285 degrees, no more than about 290 degrees, no more than about 295 degrees, or no more than about 300 degrees around the mold. As such, when the mesh 100 is deployed within an aneurysm, the mesh 100 generally curves around an axis to generally the same degree as the mesh 300 was wrapped around the mold. Because of this, in many embodiments the proximal end 300a of the mesh 300 does not meet the distal end 300b. It may be beneficial to have such an "open" curved mesh structure as it decreases the overall length of the mesh 300, thus making the occlusive device 30 easier to deliver through a catheter to the aneurysm, and also frees up some of the length of the device 30 to be used for the coil 150 (which has significantly less friction with the catheter wall and is easier to push). The "open" curved mesh structure also self-anchors at the aneurysm neck and forms a basket-like structure that captures the coil 150 between the aneurysm dome and the neck. As detailed elsewhere herein, this open configuration provides several benefits over a 360 degree or overlapping configuration, such as reduced risk of compartmentalization, better control of the microcatheter position within the aneurysm sac during delivery, and others.

In other embodiments, the mesh 300 may wrap around the axis 360 degrees or more such that it meets or overlaps itself (i.e., the proximal end 300a extends circumferentially beyond the distal end 300b) along at least a portion of the length of the mesh 300, thereby forming a closed loop (for example, as shown in FIG. 2E).

Depending on the geometry of the aneurysm to be treated, the mesh 300 may have other shapes or configurations and may be formed in a similar manner on molds having other shapes or sizes, such as non-spherical shapes, cylinders, hemispheres, polyhedrons (e.g., cuboids, tetrahedrons (e.g. pyramids), octahedrons, prisms, etc.), prolate spheroids, oblate spheroids, plates (e.g., discs, polygonal plates), bowls, non-spherical surfaces of revolution (e.g., toruses, cones, cylinders, or other shapes rotated about a center point or a coplanar axis), and combinations thereof.

In those embodiments where the mesh 300 comprises a braid, such as the example shown in FIG. 3A, the braid may be formed of a plurality of wires, at least some of which (e.g., 25% of the wires, 50% of the wires, 80% of the wires, 100% of the wires, etc.) are made of one or more shape memory and/or superelastic materials (e.g., Nitinol). In some embodiments, some or all of the wires may be drawn-filled tubes ("DFT") having a radiopaque core (e.g., platinum) surrounded by a shape memory alloy and/or superelastic alloy (e.g., Nitinol, cobalt chromium, etc.). All or a portion of the length of some or all of the wires may have one or more coatings or surface treatments. For example, some or all of the wires may have a lubricious coating or treatment that reduces the delivery force of the mesh 300 as the device 30 is advanced through the delivery catheter. In some embodiments, the coating may be relatively hydrophilic, such as a phosphorocholine compound. Additionally or alternatively, some or all of the wires may have a coating or treatment (the same as the lubricious coating, or a different coating) that enhances blood compatibility and reduces the thrombogenic surface activity of the braid. In these and other embodiments, at least a portion of the wires can be made of other suitable materials.

The coil 150 of the present technology may be formed of one or more wires wound in a helical fashion about an axis to form an elongated tubular member. The wire(s) forming the coil 150 may be circular, square, or rectangular in cross-section, and may have a cross-sectional dimension of from about 0.001 inches to about 0.003 inches, or of from about 0.0015 inches to about 0.0025 inches. In some embodiments, the wire(s) forming the coil 150 has a cross-sectional dimension no greater than 0.003 inches, no greater than 0.0025 inches, or no greater than 0.002 inches. The coil 150 may be circular, square, or rectangular in cross-section, and may have a cross-sectional dimension of from about 0.01 inches to about 0.02 inches, of from about 0.012 inches to about 0.018 inches, or of from about 0.014 inches to about 0.016 inches. In some embodiments, the coil 150 may have a cross-sectional dimension that is no greater than 0.0145 inches, and in some embodiments no greater than 0.0140 inches.

The coil 150 may have a length along the longitudinal axis L of the device 30 that is significantly longer than that of the mesh 300. For example, the coil 150 may have a length of about 2 cm to about 30 cm, about 3 cm to about 25 cm, about 4 cm to about 20 cm. In some embodiments, the length of the coil 150 may depend on the size of the aneurysm being treated. For example: for an aneurysm 4 mm in diameter or less, the coil 150 may have a length of about 6 cm; for an aneurysm 5 mm in diameter or less, the coil 150 may have a length of about 8 cm; for an aneurysm 6 mm in diameter or less, the coil 150 may have a length of about 15 cm; for an aneurysm 7 mm in diameter or less, the coil 150 may have a length of about 15 cm; for an aneurysm 8 mm in diameter or less, the coil 150 may have a length of about 20 cm; and, for an aneurysm 9 mm in diameter or less, the coil 150 may have a length of about 20 cm.

The coil 150 may be made from metals, alloys, polymers, shape memory materials (e.g., Nitinol), platinum, rhodium, palladium, tungsten, gold, silver, cobalt-chromium, and/or various alloys of these materials. In some embodiments, the coil 150 may be heat set to form a tertiary structure (i.e., a pre-determined three-dimensional structure) when in a deployed state. In some embodiments, the coil 150 does not have a tertiary structure. Additional thrombogenic elements (e.g., particles, radial filaments, polymer fibers etc.) may be attached to at least a portion of the coil 150 using any suitable binding technique; e.g., by tying or otherwise adhering them to the coil 150.

In some embodiments, the stiffness of the mesh 300 and/or occlusive device 30 may be generally constant along the longitudinal axis L, and in some embodiments, the stiffness of the mesh 300 and/or occlusive device 30 varies along the longitudinal axis L. For example, the stiffness of one or more portions of the mesh 100 can be different than other portions of the mesh 300 by varying one or more parameters such as the materials, porosity, thickness, wire size, braid count (if applicable), and/or braid pitch (if applicable). Likewise, the stiffness of one or more portions of the coil 150 can be different than other portions of the coil 150 by varying one or more parameters along the length of the coil, such as wire size, pitch, and/or cross-sectional dimension (e.g., diameter). Moreover, in some embodiments the mesh 300 may be generally stiffer than the coil 150 so that the mesh 100 better frames and anchors the device 30 within the aneurysm, and the coil 150 may be flexible and/or malleable enough to pack and fill the aneurysmal sac.

According to some aspects of the technology, the device 30 comprises only the mesh 300 and does not include the coil 150. Although the foregoing embodiments are described with respect to a single continuous mesh and a single coil, these and other embodiments of the occlusive device 30 may include more than one mesh and/or more than one coil. The mesh(es) and coil(s) may be arranged end-to-end (as described above), or one or more of the mesh(es) or coil(s) may be arranged in parallel or otherwise overlapping along at least a portion of their lengths. The mesh(es) and coil(s) may be alternating and/or the occlusive device 101 may include two or more consecutive mesh(es) and/or two or more consecutive coil(s).

Figure 7B:
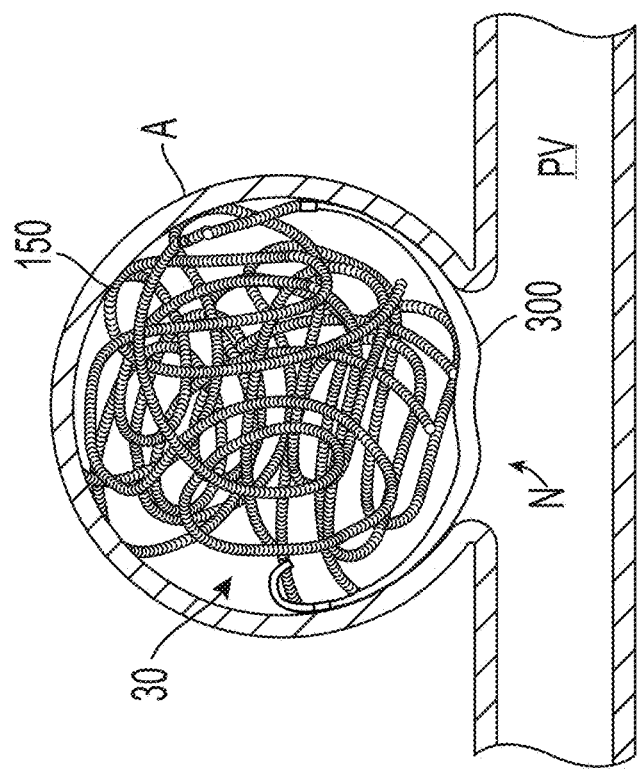
FIGS. 7A and 7B illustrate a method of deploying an occlusive device of the present technology.
Figure 7A:
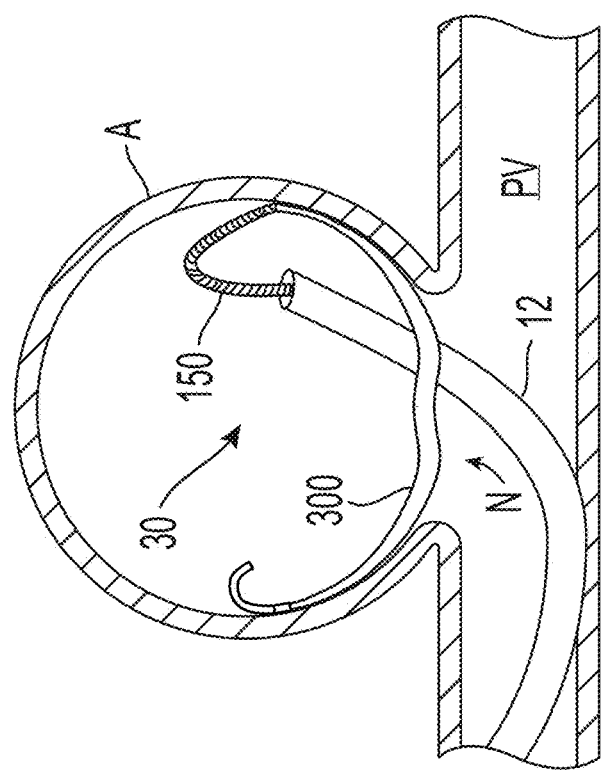

FIGS. 7A and 7B illustrate a method of deploying the occlusive device 30 in accordance with the present technology. In use, the occlusive device 30 may be intravascularly delivered to a location within a blood vessel lumen L adjacent a target aneurysm A in a low-profile configuration (not shown) within a delivery catheter 12 (e.g., a microcatheter). For delivery to the aneurysm, the occlusive device 30 may be positioned within the delivery catheter 12 such that the distal end portion 300b of the mesh 300 is closest to the distal opening of the delivery catheter 12 and thus will be released from the delivery catheter 12 before the coil 150. As a result, as described below, the coil 150 deploys within and fills an interior region at least partially defined by the already-expanded mesh 300.

The distal portion of the delivery catheter 12 is then advanced through the neck N of the aneurysm A to an interior region of the aneurysm A. As shown in FIG. 7A, the occlusive device 30 may be deployed by pushing the occlusive device 30 distally through the distal opening of the delivery catheter 12 towards the inner wall of the aneurysm A. The mesh 300 exits the delivery catheter 12 first and, as it is deployed, the mesh 300 curves around the curved inner surface of the aneurysm A, crosses the neck N, and continues to curve around the other side of the aneurysm A (though less than 360 degrees of the aneurysm). As shown in FIG. 7B, the coil 150 deploys next and fills space in the aneurysm cavity. Then, with the tip of the delivery catheter still within the aneurysm sac, the occlusive device 30 may be detached from the delivery member (such as a pusher member) via one or more of the detachment mechanisms described elsewhere herein.

In some cases, the physician may choose to deliver additional coils or embolic material (such as a liquid embolic) to the aneurysm. In these scenarios, the physician may withdraw the pusher member from the delivery catheter and, while maintaining the tip of the delivery catheter within the aneurysm sac (beyond the mesh positioned across the neck), the physician may push the additional embolic material through the delivery catheter and into the aneurysm.

The methods of the present technology may be performed under fluoroscopy such that the radiopaque portions of the device 30 may be visualized by the physician to ensure proper neck coverage. In those embodiments where the coil 150 is radiopaque (for example, when the coil 150 is a platinum coil), should the physician observe the coil 150 protruding from the neck N during deployment, the physician may pull the occlusive device 30 at least partially back into the delivery catheter 12, reposition, and redeploy in a new position.

Optionally, an embolic element, such as one or more embolic coils, liquid embolics, polymers, hydrogels and/or a framing component can be used in combination with one or more devices to facilitate delivery, engagement with the aneurysm, or increase of the packing density or fill volume. Any of these embodiments can allow increased packing density or fill volume to avoid recanalization of the aneurysm.

When positioned within the aneurysm, the mesh 300 substantially reduces and/or prevents further blood flow from the parent vessel into the aneurysm sac by disrupting blood flow from the parent vessel into the aneurysm. The mesh 300 also provides a scaffold for endothelial cell attachment. The growth and development of an endothelial layer over the neck of an aneurysm can wall off the aneurysm from the parent vessel and allow flow dynamics to equilibrate at the defect. As such, the device 30 is configured to facilitate healing of the defect and preventing recanalization by promoting tissue creation that resists aberrant blood flow and redistributes the flow pressure that may have created the defect. Upon healing with endothelialization, the pressure is evenly distributed along the parent vessel in a manner that precludes recanalization at the defect post-treatment. Moreover, blood from within the parent vessel no longer has access to the walled off defect once the endothelialization process is complete. The mesh 300 is also beneficial even if acting only as an intrasaccular neck bridge as it enables coiling of wide neck aneurysms.

Figure 8A:
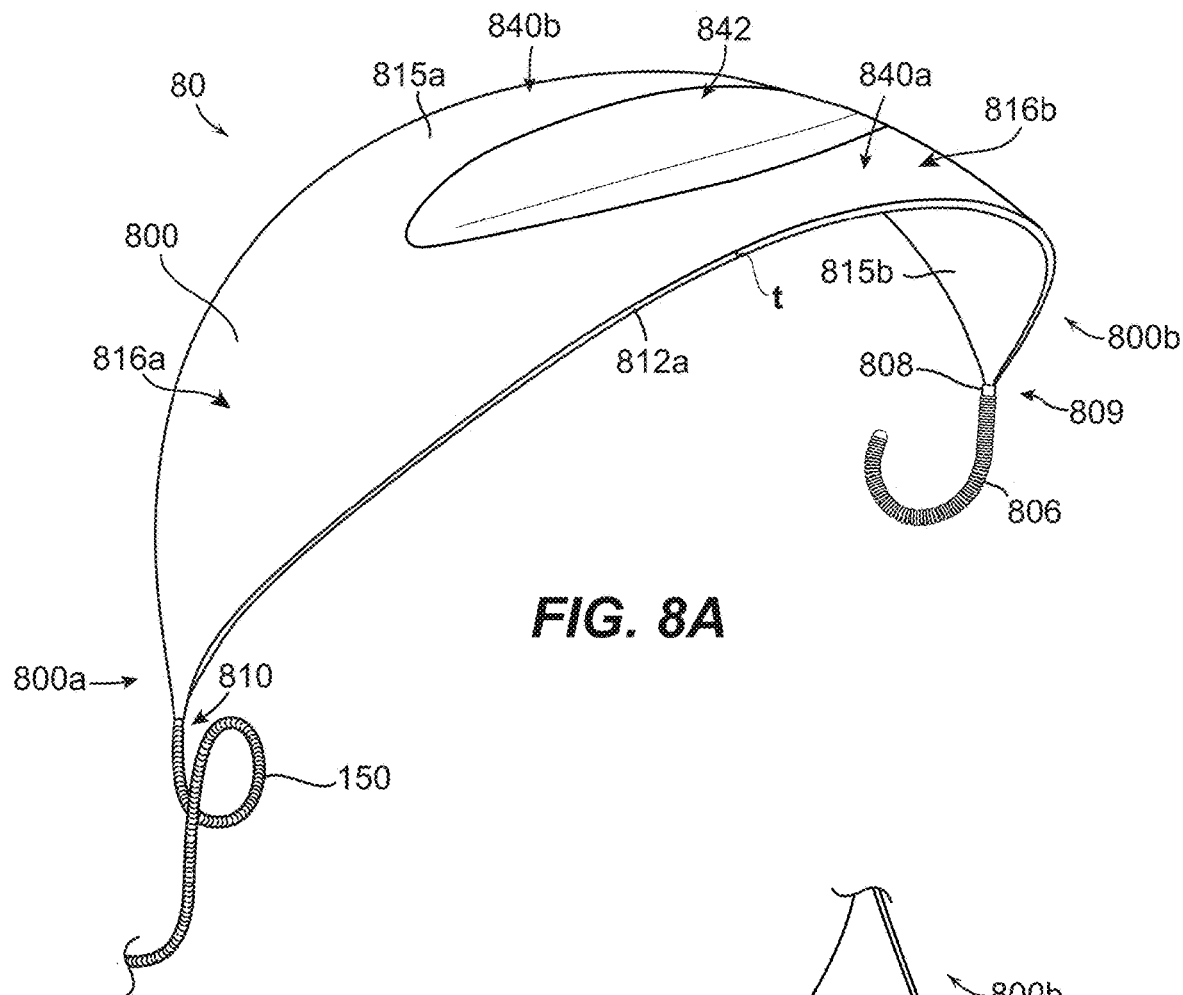
FIG. 8A is an isometric view of an occlusive device in an unconstrained state outside of an aneurysm according to some embodiments of the present technology.
Figure 8B:
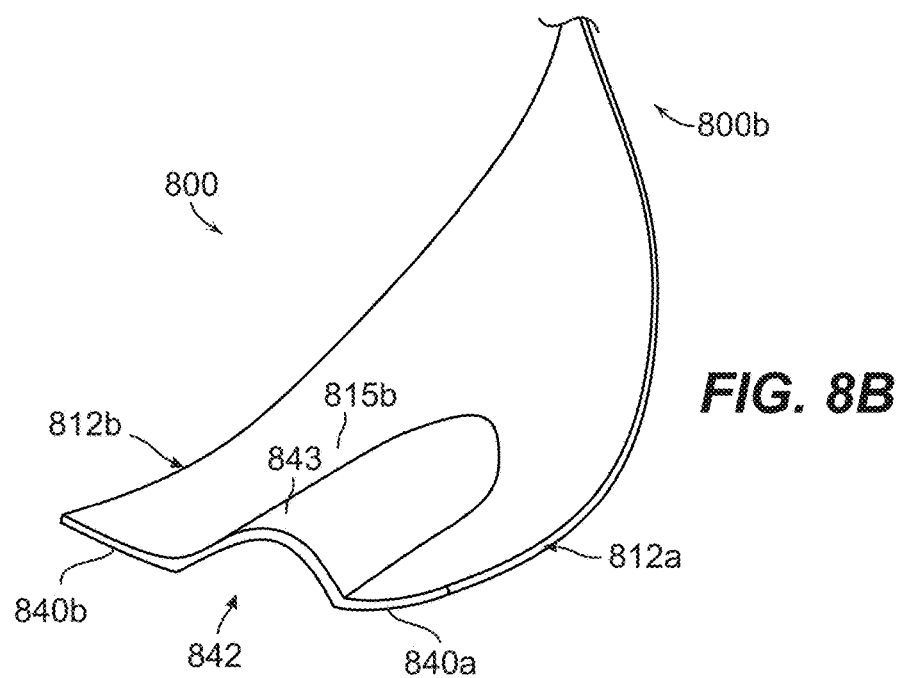
FIG. 8B is top isometric view of the mesh of the occlusive device depicted in FIG. 8A, shown in cross-section.
Figure 8C:
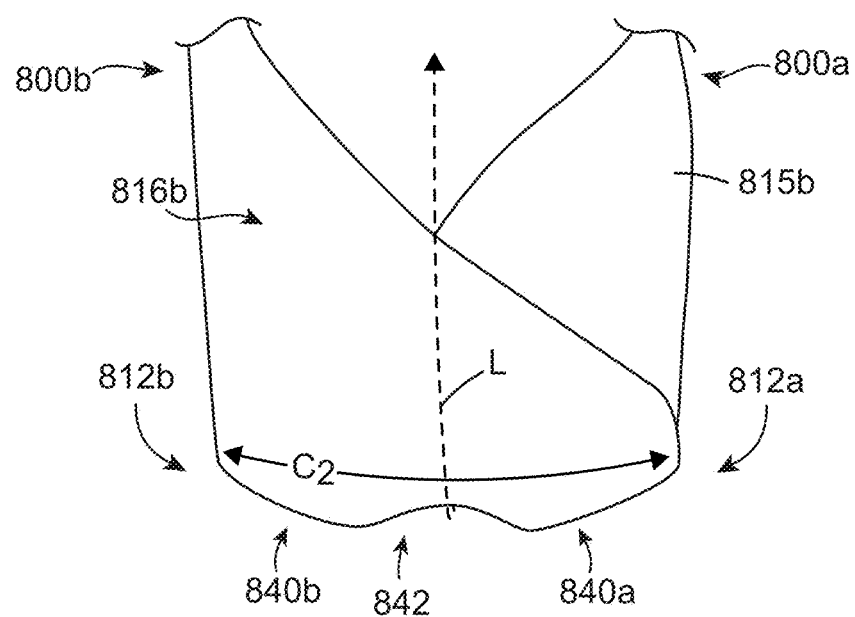
FIG. 8C is an end view of the occlusive device shown in FIG. 8A.

FIGS. 8A-8C show different views of an occlusive device 80 (or "device 80") and portions thereof in accordance with embodiments of the present technology, shown in an expanded, unconstrained state. In FIGS. 8A-8C, the mesh 800 is illustrated as an opaque, non-porous surface so the contour of the mesh 800 may be better appreciated without being obfuscated by the wires of the mesh 800. As shown, the occlusive device 80 may comprise a mesh 800 configured to be positioned across the neck N of the aneurysm and a coil 150 coupled to and extending away from a proximal end portion of the mesh 800. The coil 150 is configured to be deployed between the mesh 800 and the dome of the aneurysm to fill space within the aneurysm cavity and help stabilize and anchor the mesh 800 within the aneurysm. In some embodiments, the occlusive device 80 comprises only the mesh 800, and an embolic material (such as an embolization coil or liquid embolic) may be delivered to the aneurysm separately.

The occlusive device 80 may have several components that are generally similar to the components of occlusive device 30. For example, the occlusive device 80 may include a lead-in member 806 similar to lead-in member 306 and a distal joint 809 similar to distal joint 309. The mesh 800 may be coupled to the coil 150 at an intermediate joint 810 that is generally similar to intermediate joint 310. The proximal portion of the occlusive device 80 may include a detach element (not shown) generally similar to detach element 112. In some embodiments, the occlusive device 80 may not include one or both of the lead-in member 806 and the detach element.

As shown, the mesh 800 may have a proximal end portion 800a proximate the intermediate joint 810, a distal end portion 800b proximate the distal joint 809, and a length measured along the longitudinal axis of the mesh 800 between the intermediate and distal joints 810, 809. The mesh 800 may have opposing side edges 812a and 812b (collectively, "side edges 812") extending longitudinally along its length and a circumferential width $C_2$ (FIG. 8C) extending between its side edges 812. The mesh 800 may be curved along both its longitudinal dimension and its width dimension. The radius of curvature along the width $C_2$ of the mesh 800 may be constant or may vary, and the radius of curvature along the length of the mesh 800 may be constant or may vary. In some embodiments, the mesh 800 comprises a constantly increasing radius of curvature such that the second tapered portion 816b (or distal portion) of the mesh 800 may have a smaller radius curvature than the first tapered portion 816a (or proximal portion). The distal portion having a smaller radius of curvature helps guide the mesh 800 across the neck of the aneurysm during deployment, while the proximal portion having a larger radius of curvature helps secure and stabilize the mesh 800 within the aneurysm while the coil 150 is deployed.

As shown in FIGS. 8A-8C, the mesh 800 may include a first side 815a, a second side 815b opposite the first side 815a, and a thickness t (FIG. 8A) measured between the first and second sides 815a and 815b. When the occlusive device 80 is positioned within an aneurysm, the first side 815a is configured to face towards the parent vessel PV and the second side 815b is configured to face the aneurysm cavity. The mesh 800 may have a generally constant thickness t along its length such that the contour of the first side 815a follows the contour of the second side 815b (and vice versa). In some embodiments, the mesh 800 may have a thickness t that varies along all or a portion of its length. In particular embodiments, the mesh 800 does not define an interior volume in the unconstrained, expanded state and/or in the deployed state.

As shown, the mesh 800 may include proximal and distal tapered portions 816a and 816b (collectively, tapered portions 816) along which the width $C_2$ tapers proximally towards the intermediate joint 810 and distally towards the distal joint 809, respectively. In some embodiments, the side edges 812 may be curved along their respective lengths such that they extend at an angle relative to one another along the entire length of the mesh 800 between the tapered portions 816 such that the mesh 800 has a petal- or orange-peel shape. In some embodiments, the side edges 812 may be parallel to one another along at least a portion of the length of the mesh 800 between the tapered portions 816 (for example as shown in FIG. 1B). As such, in these and other embodiments, the mesh 800 may have a width $C_2$ that is generally constant along at least a portion of the length of the mesh 800. In some embodiments, the mesh 800 does not have any tapered portions and maintains a generally constant width $C_2$ along its entire length.

The mesh 800 may have one or more longitudinally-extending divots and/or ridges that resist and redistribute the outwardly-directed forces exerted by the coil 150 (and/or other embolic filling material) on the neck-covering portion of the mesh 800. For example, the mesh 800 may include one or more divots 842 extending along its longitudinal axis L, positioned between curved shoulder portions 840a and 840b. In the example provided in FIGS. 8A-8C, the mesh 800 includes a single divot 842 extending along an intermediate region of the mesh 800 between the tapered portions 816. The divot 842 may have a radius of curvature that is less than a radius of curvature of the shoulder portions 840a, 840b. As a result, the shoulder portions 840a, 840b may engage and conform to the curved aneurysm wall tissue proximate the neck while the protrusion 843 side of the divot 842 absorbs and redistributes downward forces (toward the parent vessel) from inside the aneurysm cavity.

In some embodiments, one or both ends of the divot 842 may extend to substantially the proximal or distal terminus of the mesh 800. The divot 842 may have a semi-circular cross-sectional shape (as shown in FIGS. 8B and 8C), or may have other suitable shapes. The divot 842 may be defined by curved sidewalls and/or linear sidewalls of the mesh 800. In some embodiments, the divot 842 may extend between the first and second end portions 800a and 800b such that the divot 842 spans substantially the entire length of the mesh 800. Although only a single divot 842 is shown in FIGS. 8A-9, in some embodiments the mesh 800 may include more divots (e.g., two divots, three divots, four divots, etc.). In those embodiments having multiple divots, the divots may be co-extensive with one another, or may have different lengths and/or occupy different lengths or latitudes of the mesh 800.

As depicted in FIGS. 8B and 8C, in some embodiments the divot 842 may extend towards the second side 815b of the mesh 800 such that the opening of the divot 842 is at the first side 815a (e.g., the parent vessel-facing side) and the second side 815b of the mesh 800 (e.g., the aneurysm-facing side) includes a raised portion 843 (FIG. 8B) that corresponds to the divot 842. As such, the mesh 800 is configured to be positioned within an aneurysm such that the portion of the mesh 800 forming the divot 842 faces the parent vessel such that the divot 842 is concave towards the parent vessel and convex towards the aneurysm cavity. As such, at least along an intermediate portion and/or non-tapering portion of the mesh 800, the mesh 800 undulates between its side edges 812a and 812b.

When the mesh 800 is positioned over the neck of an aneurysm and the coil 150 (or other embolic material) exerts an outwardly-directed force (i.e., towards the parent vessel) on the portion of the mesh 800 spanning the neck, the convex or raised portion 843 at the second side 815b of the mesh 800 absorbs the force and redistributes the force laterally towards the side edges 812 of the mesh 800. As such, in response to the outwardly-directed forces, the curvature of the raised portion 843 lessens and the shoulder portions 840a and 840b of the mesh 800 get pushed farther up and around the inner surface of the aneurysm wall. This way, more of the mesh 800 engages the inner surface of the aneurysm wall, which further secures and stabilizes the mesh 800 within the aneurysm. Even more importantly, the deformation of the mesh 800 does not break the plane of the aneurysm neck and thus does not protrude into the parent vessel. Accordingly, the meshes of the present technology are configured to absorb and deform in response to outwardly-directed forces without causing a prolapse of the mesh 800 into the parent vessel.

Figure 8D:
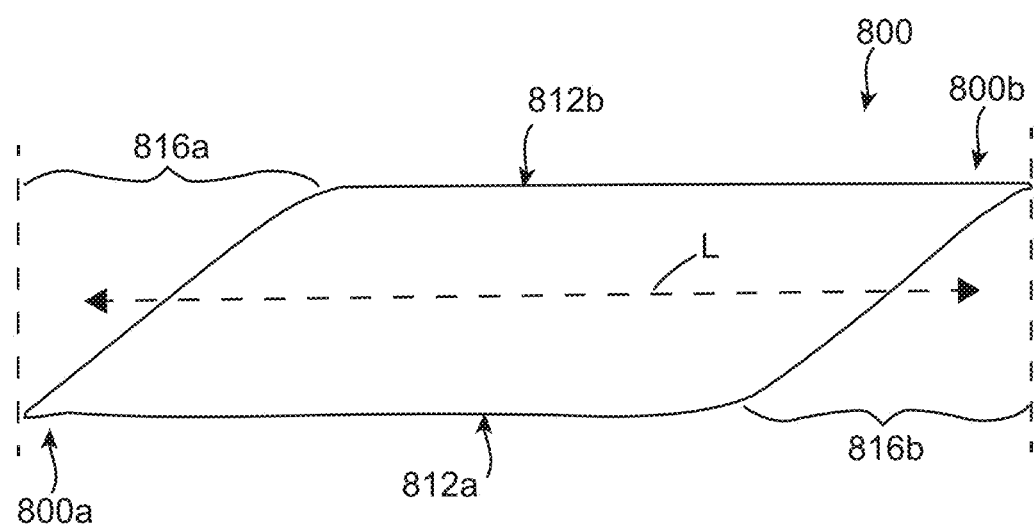
FIG. 8D is a top view of the mesh shown in FIG. 8A, depicted as held in an unfurled, laid-flat configuration.
Figure 9:
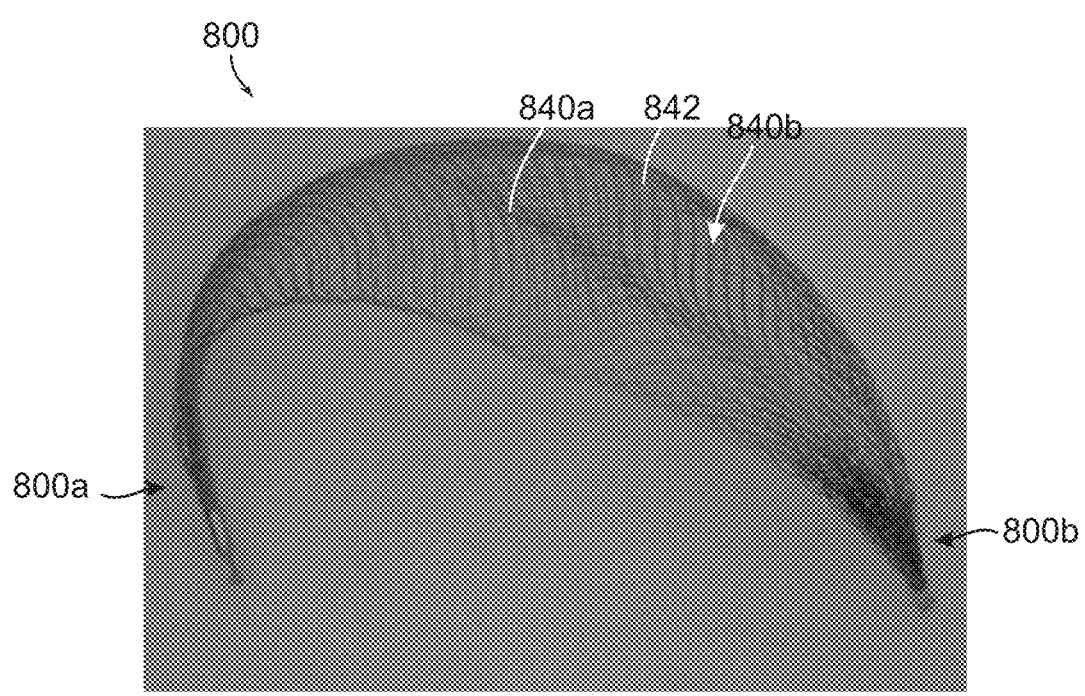
FIG. 9 is an isometric view of a portion of an occlusive device in an unconstrained state in accordance with the present technology.

FIG. 8D is a top view of the mesh 800 in an unfurled, laid-flat configuration. While in an unconstrained state the mesh 800 would assume the shape shown in FIG. 8A, FIG. 8D depicts the mesh 800 if it was laid on a flat surface in its heat set configuration and had its ends held down. (The divot is not shown in FIG. 8D for simplicity of explanation.) As best visualized in FIGS. 8C and 8D, in some embodiments the mesh 800 may have tapered portions 816a, 816b that taper in the direction of opposing side edges 812a, 812b. For example, the first or proximal tapered portion 816a may taper in a proximal direction (towards intermediate joint 810) and towards the first side edge 812a, and the second or distal tapered portion 816b may taper in a distal direction (towards distal joint 809) and towards the second side edge 812b. In some embodiments, the tapered portions 816a, 816b may taper in the opposite fashion, such that the first tapered portion 816a tapers in a proximal direction (towards intermediate joint 810) towards the second side edge 812b, and the second tapered portion 816b may taper in a distal direction (towards distal joint 809) towards the first side edge 812a. In any case, the proximal and distal ends 800a, 800b of the mesh 800 thus may be offset from the central longitudinal axis L of the mesh 800 in different directions. This "double offset" feature reduces the possibility of the mesh impinging on the catheter tip during deployment as the portion of the mesh 800 being deployed will follow the distal offset and thus "get out of the way" of the more proximal portion of the mesh 800 as it is being deployed. The double offset feature also reduces the likelihood of compartmentalization (i.e., when the embolic filler material, such as coils, are deployed in a single location and not uniformly distributed throughout the aneurysm cavity). Any of the meshes detailed herein (e.g., mesh 100, mesh 300, mesh 1000, etc.) may also have offset end portions.

The mesh 800 may be formed of a stent, a braid, a lattice, a weave, a fabric, a laser-cut sheet, and/or any other suitable porous structure. In some embodiments, the mesh 800 is not a porous structure, such as a flexible metal or plastic sheet. The mesh 800 may comprise any of the meshes described elsewhere herein, such as mesh 100, mesh 300, and mesh 1000. Likewise, the coil 150 of the occlusive device 80 can be any of the coils described herein. In some embodiments, the device 80 comprises only the mesh 800 and does not include the coil 150.

The mesh 800 may be delivered to an aneurysm (such as a cerebral aneurysm) and deployed within the aneurysm as detailed above with respect to mesh 300 and FIGS. 7A and 7B.

Figure 10:
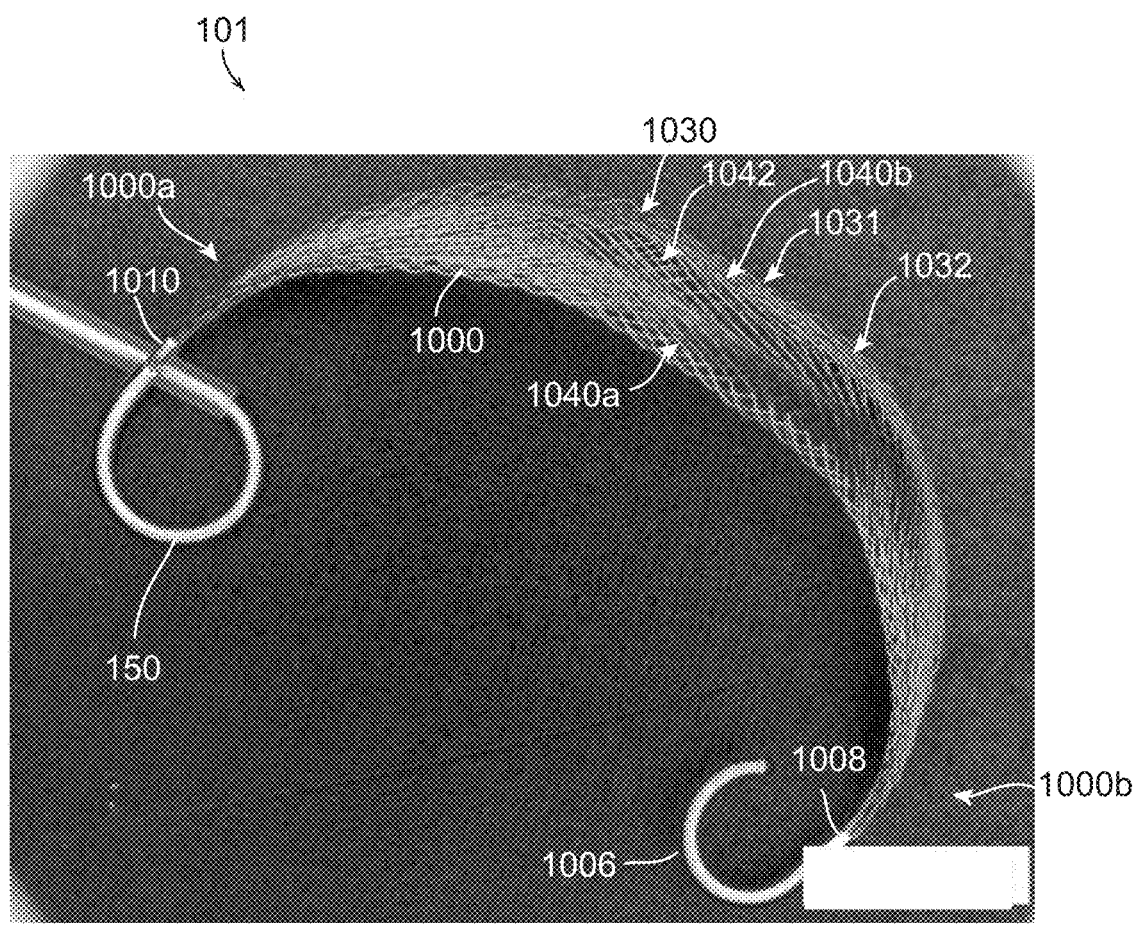
FIG. 10 is an isometric view of a portion of an occlusive device in an unconstrained state in accordance with the present technology.

FIG. 10 is an isometric view of a portion of an occlusive device 101 (or "device 101") in accordance with embodiments of the present technology, shown in an expanded, unconstrained state. The occlusive device 101 may comprise a mesh 1000 configured to be positioned across the neck N of the aneurysm and a coil 150 coupled to and extending away from an end portion of the mesh 1000. Similar to the description provided above with reference to occlusive device 30 and FIG. 3B, the coil 150 is configured to be deployed between the mesh 1000 and the dome of the aneurysm to fill space within the aneurysm cavity. In some embodiments, the occlusive device 101 comprises only the mesh 1000, and an embolic material (such as one or more embolization coils) may be delivered to the aneurysm separately. As described in greater detail below, the mesh 1000 may have one or more longitudinally-extending divots 1042 and one or more laterally-extending undulations 1030, 1031, 1032 that resist and redistribute the outwardly-directed forces exerted by the coil (or other embolic filling material) on the neck-covering portion of the mesh 1000.

The occlusive device 101 may have several components that are generally similar to the components of occlusive device 10. For example, the occlusive device 101 may include a lead-in member 1006 similar to lead-in member 106 and a distal joint 1009 similar to distal joint 109. The mesh 1000 may be coupled to the coil 150 via an intermediate joint 1010 that is generally similar to intermediate joint 110. The proximal portion of the occlusive device 101 may include a detach element (not shown) generally similar to detach element 112 that is configured to be detachably coupled to a delivery device. In some embodiments, the occlusive device 101 may not include one or more of the lead-in member 1006, the distal joint 1009, the intermediate joint 1010, and the detach element.

Figure 11A:
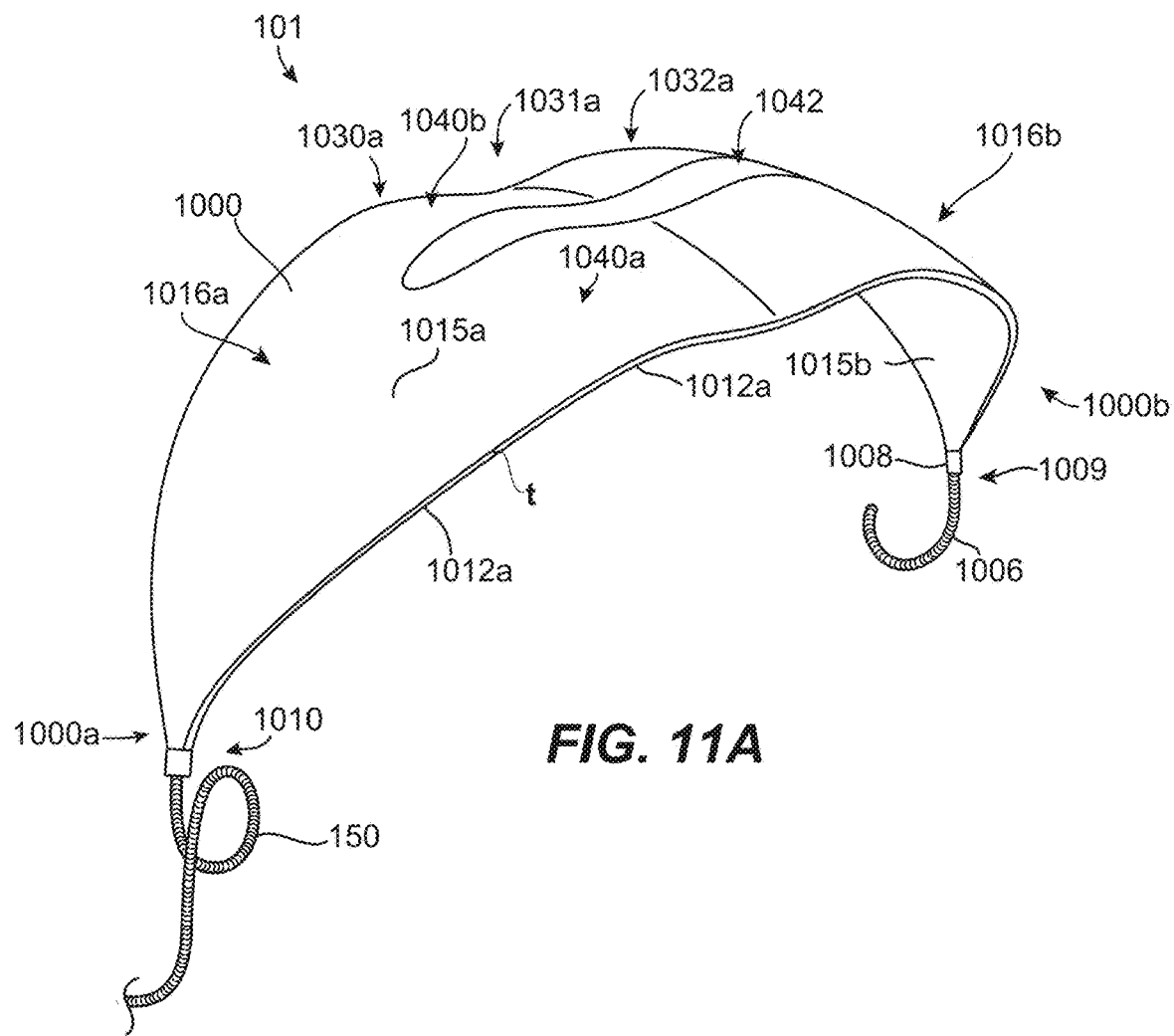
FIG. 11A is a bottom isometric view of a portion of an occlusive device in an unconstrained state outside of an aneurysm according to some embodiments of the present technology.
Figure 11B:
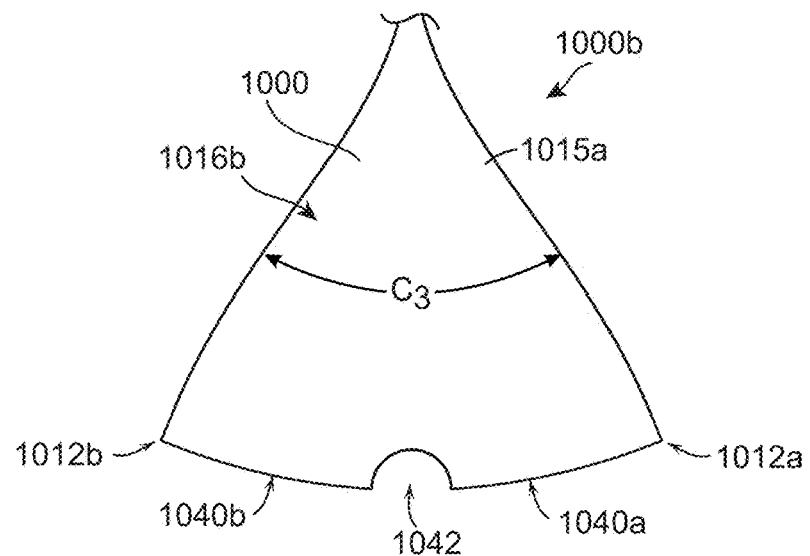
FIG. 11B is an end view of the occlusive device shown in FIG. 11A.
Figure 11C:
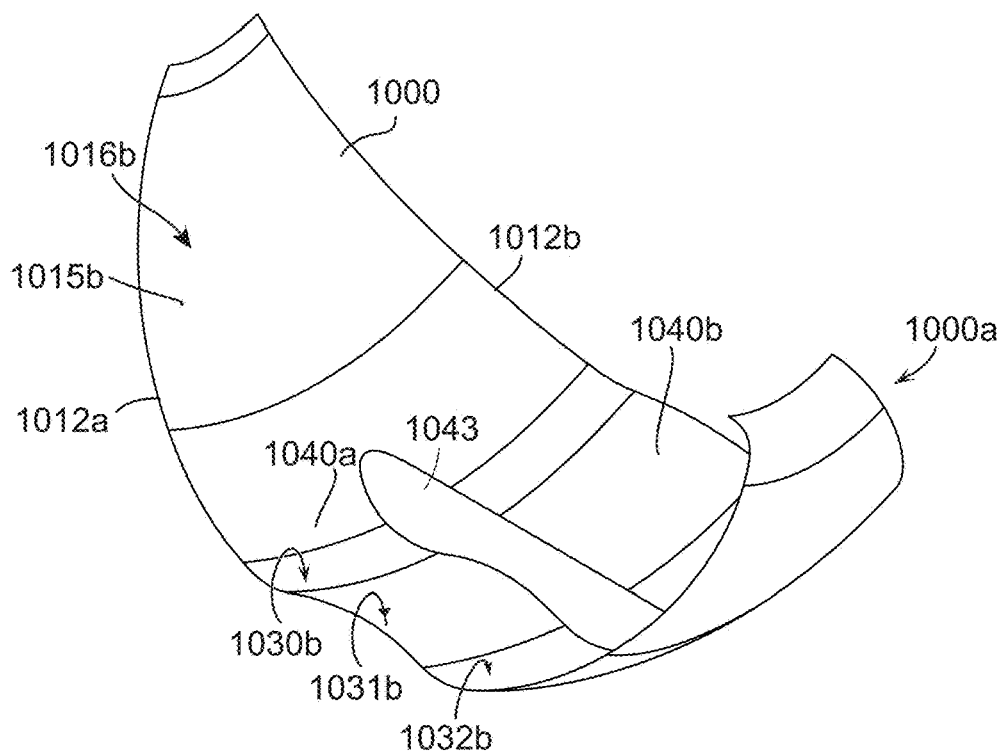
FIG. 11C is top isometric view of the mesh of the occlusive device depicted in FIG. 11A.

FIGS. 11A-11C show different views of portions of the occlusive device 101 in an unconstrained, expanded state with the mesh 1000 illustrated as an opaque, non-porous surface so that the contour of the mesh 1000 may be better appreciated without being obfuscated by the wires of the mesh 1000. As shown, the mesh 1000 may have a proximal end portion 1000a proximate the joint 1010, a distal end portion 1000b proximate the distal joint 1009, and a length measured along the longitudinal axis of the mesh 1000 between the intermediate joint 1010 and the distal joint 1009. The mesh 1000 may have opposing side edges 1012a and 1012b (collectively, "side edges 1012") extending longitudinally along its length and a circumferential width $C_3$ (FIG. 11B) extending between its side edges 1012. The mesh 1000 may be curved along both its longitudinal dimension (see FIG. 11A) and its width dimension (see FIG. 11B). The radius of curvature along the width $C_3$ of the mesh 1000 may be constant or may vary, and the radius of curvature along the length of the mesh 1000 may be constant or may vary. In some embodiments, the mesh 1000 comprises a constantly increasing radius of curvature such that the second tapered portion 1016b (or distal portion) of the mesh 1000 may have a smaller radius curvature than the first tapered portion 1016a (or proximal portion). The distal portion having a smaller radius of curvature helps guide the mesh 1000 across the neck of the aneurysm during deployment, while the proximal portion having a larger radius of curvature helps secure and stabilize the mesh 1000 within the aneurysm while the coil 150 is deployed.

As shown in FIGS. 11A-11C, the mesh 1000 may include a first side 1015a, a second side 1015b opposite the first side 1015a, and a thickness t (FIG. 11A) measured between the first and second sides 1015a and 1015b. When the occlusive device 101 is positioned within an aneurysm, the first side 1015a is configured to face towards the parent vessel PV and the second side 1015b is configured to face the aneurysm cavity. The mesh 1000 may have a generally constant thickness t along its length such that the contour of the first side 1015a follows the contour of the second side 1015b (and vice versa). In some embodiments, the mesh 1000 may have a thickness t that varies along all or a portion of its length. In particular embodiments, the mesh 1000 does not define an interior volume in the unconstrained, expanded state and/or in the deployed state.

As shown, the mesh 1000 may include proximal and distal tapered portions 1016a and 1016b (collectively, tapered portions 1016) along which the width $C_3$ tapers towards the intermediate joint 1010 and the distal joint 1009, respectively. In some embodiments, the side edges 1012 may extend at an angle relative to one another along the entire length of the mesh 1000 between the tapered portions 1016 such that the mesh 1000 has a petal or orange-peel shape. In some embodiments, the side edges 1012 may be parallel to one another along at least a portion of the length of the mesh 1000 between the tapered portions 1016 (for example as shown in FIG. 1B). As such, in these and other embodiments, the mesh 1000 may have a width $C_3$ that is generally constant along at least a portion of the length of the mesh 1000. In some embodiments, the mesh 1000 does not have any tapered portions and maintains a generally constant width $C_3$ along its entire length.

Figure 11D:
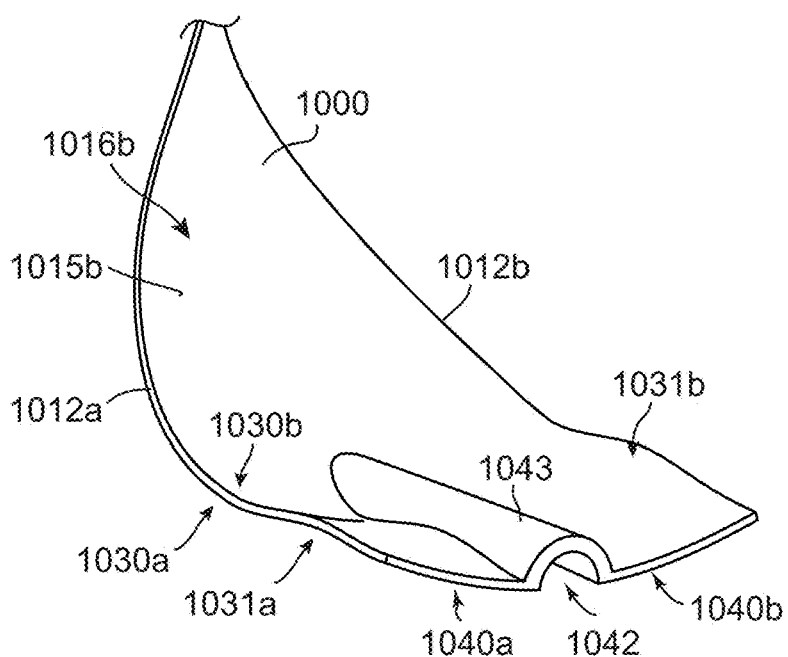
FIG. 11D is top isometric view of the mesh of the occlusive device depicted in FIG. 11A, shown in cross-section.

The mesh 1000 may include one or more divots 1042 extending along its longitudinal axis L, positioned between shoulder portions 1040a and 1040b. In the example provided in FIGS. 11A-11D, the mesh 1000 includes a single divot 1042 extending along an intermediate region of the mesh 1000 between the tapered portions 1016. The divot 1042 may have a semi-circular cross-sectional shape (as shown in FIGS. 11B and 11D), or may have other suitable shapes. The divot 1042 may be defined by curved sidewalls and/or linear sidewalls of the mesh 1000. In some embodiments, the divot 1042 may extend between the first and second end portions 1000a and 1000b such that the divot 1042 spans substantially the entire length of the mesh 1000. Although only a single divot 1042 is shown in FIGS. 11A-11D, in some embodiments the mesh 1000 may include more divots (e.g., two divots, three divots, four divots, etc.). In those embodiments having multiple divots, the divots may be co-extensive with one another, or may have different lengths and/or occupy different lengths or latitudes of the mesh 1000.

As depicted in FIGS. 11B and 11D, in some embodiments the divot 1042 may extend towards the second side 1015b of the mesh 1000 such that the opening of the divot 1042 is at the first side 1015a (e.g., the parent vessel-facing side) and the second side 1015b of the mesh 1000 (e.g., the aneurysm-facing side) includes a raised portion 1043 (FIGS. 11C and 11D) that corresponds to the divot 1042. As such, the mesh 1000 is configured to be positioned within an aneurysm such that the portion of the mesh 1000 forming the divot 1042 faces the parent vessel such that the divot 1042 is concave towards the parent vessel and convex towards the aneurysm cavity. As such, at least along an intermediate portion of the mesh 1000, the mesh 1000 undulates between its side edges 1012a and 1012b.

The mesh 1000 may also include one or more laterally-extending undulations. For example, in the embodiment shown in FIGS. 11A-11D, the first side 1015a of the mesh 1000 includes first and second peaks 1030a and 1032a separated by a valley 1031a. The mesh 1000 is configured to be positioned over the neck of an aneurysm such that the first and second peaks 1030a and 1032a are convex towards the parent vessel while the valley 1031a is concave towards the parent vessel. As best shown in FIGS. 11C and 11D, the second side 1015b of the mesh 1000 includes first and second valleys 1030b and 1032b separated by a peak 1031b (only second valley 1032a is visible in FIG. 11C). Because the thickness t of the mesh 1000 is generally constant along the length of the mesh 1000 (at least in the present example), the axial locations of the first and second peaks 1030a and 1032a correspond to the axial locations of the first and second valleys 1030b and 1032b, and the axial location of the valley 1031a corresponds to the axial location of the peak 1031b. The mesh 300 is configured to be positioned over the neck of an aneurysm such that the first and second valleys 1030b and 1032b are concave towards the aneurysm cavity while the peak 1031b is convex towards the aneurysm cavity.

In the example shown in FIGS. 11C and 11D, the longitudinally-extending divot 1042 extends through each of the laterally-extending undulations 1030, 1031, and 1032. According to several aspects of the technology, the divot 1042 may run through or intercept less than all of the undulations 1030, 1031, and 1032. In some embodiments, the mesh 1000 may comprise more than one divot, and one, some, or all of the more than one divot may extend through one, some, or all of the undulations.

In some embodiments, such as the example shown in FIGS. 10-11D, the shoulder portions 1040a, 1040b comprise at least a portion of each of the laterally-extending undulations 1030, 1031, and 1032. As such, the shoulder portions 1040a, 1040b undulate in a longitudinal direction. Moreover, the shoulder portions 1040a, 1040b may curve along their circumferential widths and have a corresponding radius of curvature, and the protrusion 1043 may also have a radius of curvature. In some embodiments, the radius of curvature of the shoulder portions 1040a, 1040b may be greater than the radius of curvature of the protrusion 1043. In such embodiments, the mesh 1000 may absorb more force initially via the protrusion 1043.

When the mesh 1000 is positioned over the neck of an aneurysm and the coil 150 (or other embolic material) exerts an outwardly-directed force (i.e., towards the parent vessel) on the portion of the mesh 1000 spanning the neck, the convex or raised portions 1031 and 1043 at the second side 1015b of the mesh 1000 absorb the force. The raised portion 1031 redistributes the force longitudinally and upwardly along the tapered portions 1016 of the mesh 1000, while the raised portion 1043 redistributes the force laterally towards the side edges 1012 of the mesh 1000. As such, in response to the outwardly-directed forces, the curvature of the raised portions 1031 and 1043 lessen and the first and second end portions 1000a and 1000b and shoulders 1040a and 1040b get pushed farther up and around the inner surface of the aneurysm wall. This way, more of the mesh 1000 engages the inner surface of the aneurysm wall, which further secures and stabilizes the mesh 1000 within the aneurysm. Even more importantly, the deformation of the mesh 1000 does not break the plane of the aneurysm neck and thus does not protrude into the parent vessel. Accordingly, the meshes of the present technology are configured to absorb and deform in response to outwardly-directed forces without causing a prolapse of the mesh 1000 into the parent vessel PV.

The mesh 1000 may be formed of a stent, a braid, a lattice, a weave, a laser-cut sheet, and/or any other suitable porous material or structure. The mesh 1000, for example, may comprise any of the meshes described elsewhere herein, such as mesh 100, mesh 300, and mesh 800. Likewise, the coil 150 of the occlusive device 101 can be any of the coils described herein. In some embodiments, the device 101 comprises only the mesh 1000 and does not include the coil 150.

The mesh 1000 may be delivered to an aneurysm (such as a cerebral aneurysm) and deployed within the aneurysm as detailed above with respect to mesh 300 and FIGS. 7A and 7B.

Figure 12C:
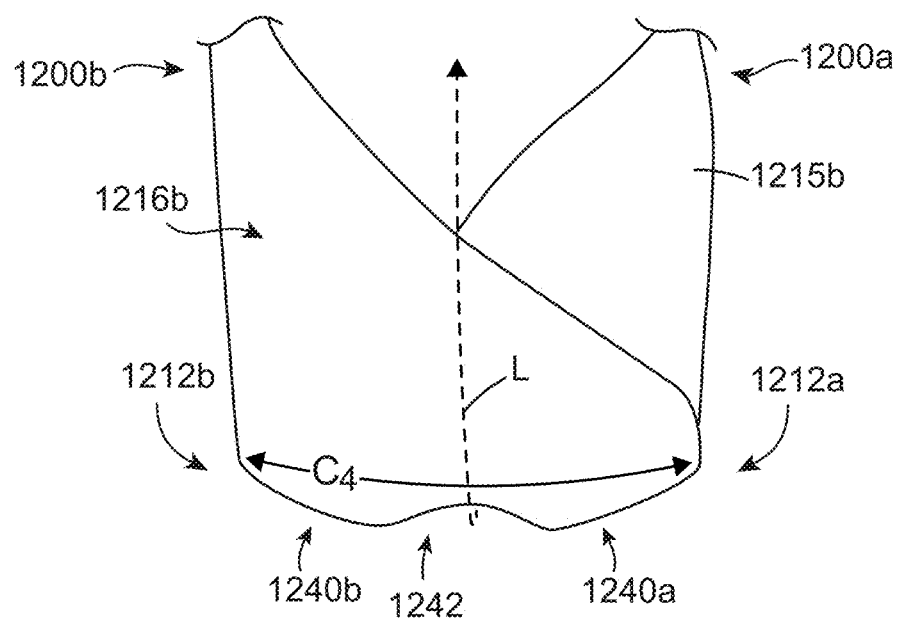

FIGS. 12A-12C show different views of an occlusive device 120 (or "device 120") and portions thereof in accordance with embodiments of the present technology, shown in an expanded, unconstrained state. In FIGS. 12A-12C, the mesh 1200 is illustrated as an opaque, non-porous surface so the contour of the mesh 1200 may be better appreciated without being obfuscated by the wires of the mesh 1200. As shown, the occlusive device 120 may comprise a mesh 1200 configured to be positioned across the neck N of the aneurysm and a coil 150 coupled to and extending away from a proximal end portion of the mesh 1200. The coil 150 is configured to be deployed between the mesh 1200 and the dome of the aneurysm to fill space within the aneurysm cavity and help stabilize and anchor the mesh 1200 within the aneurysm. In some embodiments, the occlusive device 120 comprises only the mesh 1200, and an embolic material (such as an embolization coil or liquid embolic) may be delivered to the aneurysm separately.

The occlusive device 120 may have several components that are generally similar to the components of occlusive device 30. For example, the occlusive device 120 may include a lead-in member 1206 similar to lead-in member 306 and a distal joint 1209 similar to distal joint 309. The mesh 1200 may be coupled to the coil 150 at an intermediate joint 1210 that is generally similar to intermediate joint 310. The proximal portion of the occlusive device 120 may include a detach element (not shown) generally similar to detach element 112. In some embodiments, the occlusive device 120 may not include one or both of the lead-in member 1206 and the detach element.

As shown, the mesh 1200 may have a proximal end portion 1200a proximate the intermediate joint 1210, a distal end portion 1200b proximate the distal joint 1209, and a length measured along the longitudinal axis of the mesh 1200 between the intermediate and distal joints 1210, 1209. The mesh 1200 may have opposing side edges 1212a and 1212b (collectively, "side edges 1212") extending longitudinally along its length and a circumferential width $C_4$ (FIG. 12C) extending between its side edges 1212.

Figure 13A:
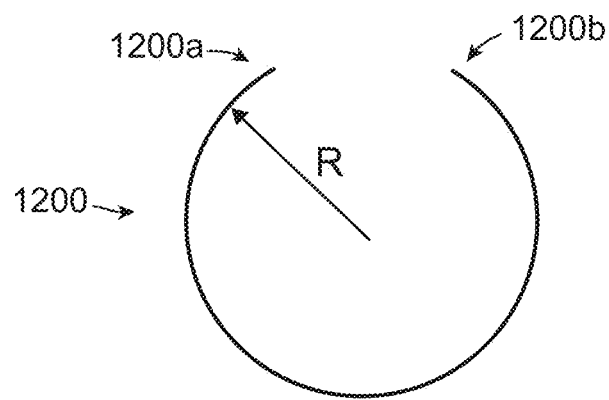
FIGS. 13A and 13B are schematic views of meshes of the present technology having constant and varying radii of curvature, respectively.
Figure 13B:
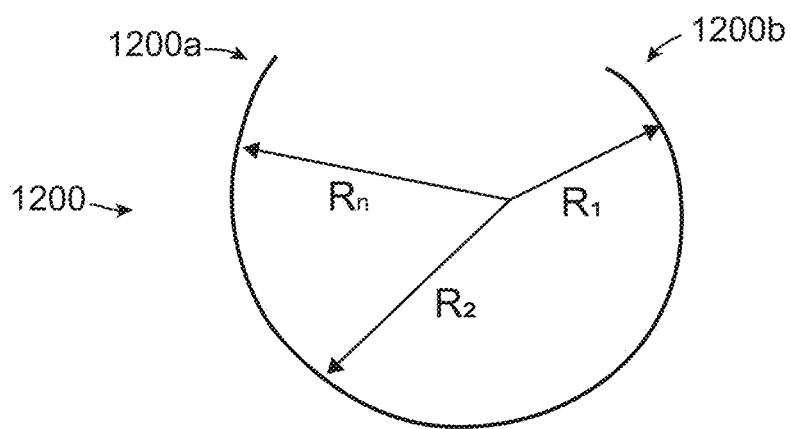

The mesh 1200 may be curved along both its longitudinal dimension and its width dimension. The radius of curvature along the width $C_4$ of the mesh 1200 may be constant or may vary, and the radius of curvature along the length of the mesh 1200 may be constant (see, for example, FIG. 13A) or may vary (see, for example, FIG. 13B). In some embodiments, the mesh 1200 comprises a constantly increasing radius of curvature such that the second tapered portion 1216b (or distal portion) of the mesh 1200 may have a smaller radius curvature than the first tapered portion 1216a (or proximal portion). The distal portion having a smaller radius of curvature helps guide the mesh 1200 across the neck of the aneurysm during deployment, while the proximal portion having a larger radius of curvature helps secure and stabilize the mesh 1200 within the aneurysm while the coil 150 is deployed.

As shown in FIGS. 12A-12C, the mesh 1200 may include a first side 1215a, a second side 1215b opposite the first side 1215a, and a thickness t (FIG. 12A) measured between the first and second sides 1215a and 1215b. When the occlusive device 120 is positioned within an aneurysm, the first side 1215a is configured to face towards the parent vessel PV and the second side 1215b is configured to face the aneurysm cavity. The mesh 1200 may have a generally constant thickness t along its length such that the contour of the first side 1215a follows the contour of the second side 1215b (and vice versa). In some embodiments, the mesh 1200 may have a thickness t that varies along all or a portion of its length. In particular embodiments, the mesh 1200 does not define an interior volume in the unconstrained, expanded state and/or in the deployed state in the aneurysm.

As shown, the mesh 1200 may include proximal and distal tapered portions 1216a and 1216b (collectively, tapered portions 1216) along which the width $C_4$ tapers proximally towards the intermediate joint 1210 and distally towards the distal joint 1209, respectively. In some embodiments, the side edges 1212 may be curved along their respective lengths such that the width $C_4$ of the mesh 1200 along the length between the tapered portions 1216 varies. In some embodiments, the side edges 1212 may be parallel to one another along all or a portion of the length of the mesh 1200 between the tapered portions 1216. As such, in these and other embodiments, the mesh 1200 may have a width $C_4$ that is generally constant along at least a portion of the length of the mesh 1200. In some embodiments, the mesh 1200 does not have any tapered portions and maintains a generally constant width $C_4$ along its entire length.

As best shown in FIG. 12A, the device 120 may include a guide (here a curved tail 1260, also referred to as "tail 1260") extending between the proximal tapered portion 1216*a* of the mesh 1200 and the coil 150. In such embodiments, the proximal end 1200*a* of the mesh 1200 corresponds to the proximal end of the tail 1260. As shown in the cross-sectional end view of FIG. 12B, the curved tail 1260 may comprise a radially compacted, curved or bent portion of the mesh 1200 that connects the proximal end 1262 of the proximal tapered portion 1216*a* to the distal end 150*b* of the coil 150. As such, the mesh of the proximal tapered portion 1216*a* is continuous and/or integral with the tail 1260. In some embodiments, the curved tail 1260 can be a separate component coupled to the mesh 1200 and/or coil 150, and/or the curved tail 1260 can have other suitable shapes and/or configurations. As described in greater detail below with respect to FIGS. 15A-18F, the curved tail 1260 may be configured to re-orient the mesh 1200 as it is being released into the aneurysm such that the mesh 1200 drops in over the neck.

The mesh 1200 may have one or more longitudinally-extending divots and/or ridges that resist and redistribute the outwardly-directed forces exerted by the coil 150 (and/or other embolic filling material) on the neck-covering portion of the mesh 1200. For example, the mesh 1200 may include one or more divots 1242 extending along its longitudinal axis L, positioned between curved shoulder portions 1240*a* and 1240*b*. In the example provided in FIGS. 12A-12C, the mesh 1200 includes a single divot 1242 extending along an intermediate region of the mesh 1200 between the tapered portions 1216. The divot 1242 may have a radius of curvature that is less than a radius of curvature of the shoulder portions 1240*a*, 1240*b*. As a result, the shoulder portions 1240*a*, 1240*b* may engage and conform to the curved aneurysm wall tissue proximate the neck while the protrusion 1243 side of the divot 1242 absorbs and redistributes downward forces (toward the parent vessel) from inside the aneurysm cavity.

In some embodiments, one or both ends of the divot 1242 may extend to substantially the proximal or distal terminus of the mesh 1200. The divot 1242 may have a semi-circular cross-sectional shape (as shown in FIGS. 12B and 12C), or may have other suitable shapes. The divot 1242 may be defined by curved sidewalls and/or linear sidewalls of the mesh 1200. In some embodiments, the divot 1242 may extend between the first and second end portions 1200*a* and 1200*b* such that the divot 1242 spans substantially the entire length of the mesh 1200. Although only a single divot 1242 is shown in FIGS. 12A-12D, in some embodiments the mesh 1200 may include more divots (e.g., two divots, three divots, four divots, etc.). In those embodiments having multiple divots, the divots may be co-extensive with one another, or may have different lengths and/or occupy different lengths or latitudes of the mesh 1200.

As depicted in FIGS. 12B and 12C, in some embodiments the divot 1242 may extend towards the second side 1215*b* of the mesh 1200 such that the opening of the divot 1242 is at the first side 1215*a* (e.g., the parent vessel-facing side) and the second side 1215*b* of the mesh 1200 (e.g., the aneurysm-facing side) includes a raised portion 1243 (FIG. 12B) that corresponds to the divot 1242. As such, the mesh 1200 is configured to be positioned within an aneurysm such that the portion of the mesh 1200 forming the divot 1242 faces the parent vessel such that the divot 1242 is concave towards the parent vessel and convex towards the aneurysm cavity. As such, at least along an intermediate portion and/or non-tapering portion of the mesh 1200, the mesh 1200 undulates between its side edges 1212*a* and 1212*b*.

When the mesh 1200 is positioned over the neck of an aneurysm and the coil 150 (or other embolic material) exerts an outwardly-directed force (i.e., towards the parent vessel) on the portion of the mesh 1200 spanning the neck, the convex or raised portion 1243 at the second side 1215*b* of the mesh 1200 absorbs the force and redistributes the force laterally towards the side edges 1212 of the mesh 1200. As such, in response to the outwardly-directed forces, the curvature of the raised portion 1243 lessens and the shoulder portions 1240*a* and 1240*b* of the mesh 1200 get pushed farther up and around the inner surface of the aneurysm wall. This way, more of the mesh 1200 engages the inner surface of the aneurysm wall, which further secures and stabilizes the mesh 1200 within the aneurysm. Even more importantly, the deformation of the mesh 1200 does not break the plane of the aneurysm neck and thus does not protrude into the parent vessel. Accordingly, the meshes of the present technology are configured to absorb and deform in response to outwardly-directed forces without causing a prolapse of the mesh 1200 into the parent vessel.

Figure 12D:
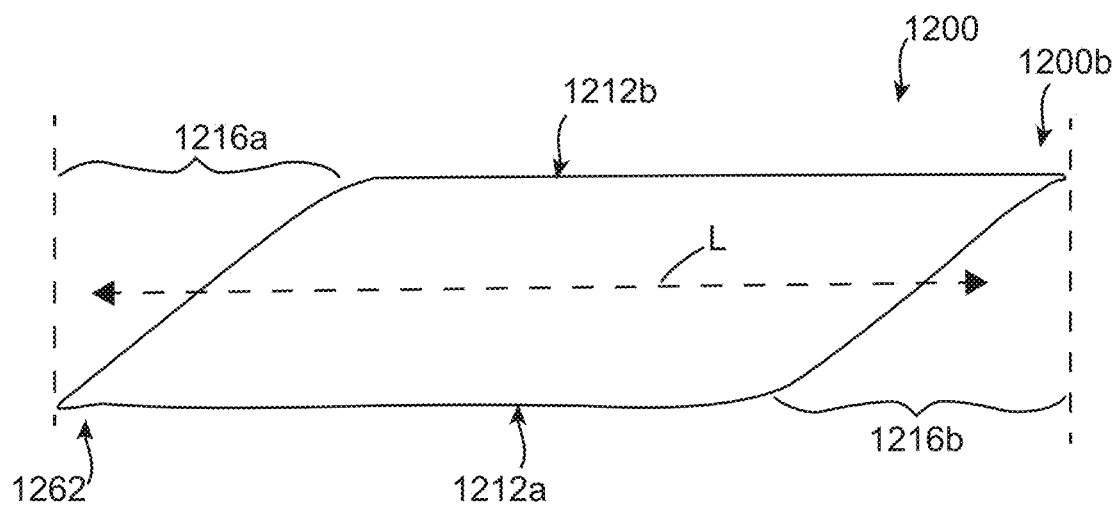

FIG. 12D is a top view of the mesh 1200 in an unfurled, laid-flat configuration. While in an unconstrained state the mesh 1200 would assume the shape shown in FIG. 12A, FIG. 12D depicts the mesh 1200 as if it was laid on a flat surface in its heat set configuration and had its ends held down. As previously mentioned, the divot is not depicted in FIG. 12D for ease of illustration.

As best visualized in FIGS. 12C and 12D, in some embodiments the mesh 1200 may have tapered portions 1216*a*, 1216*b* that taper in the direction of opposing side edges 1212*a*, 1212*b*. For example, the first or proximal tapered portion 1216*a* may taper in a proximal direction (towards intermediate joint 1210) and towards the first side edge 1212*a*, and the second or distal tapered portion 1216*b* may taper in a distal direction (towards distal joint 1209) and towards the second side edge 1212*b*. In some embodiments, the tapered portions 1216*a*, 1216*b* may taper in the opposite fashion, such that the first tapered portion 1216*a* tapers in a proximal direction (towards intermediate joint 1210) towards the second side edge 1212*b*, and the second tapered portion 1216*b* may taper in a distal direction (towards distal joint 1209) towards the first side edge 1212*a*. In any case, the proximal and distal ends 1200*a*, 1200*b* of the mesh 1200 thus may be offset from the central longitudinal axis L of the mesh 1200 in different directions. This "double offset" feature reduces the possibility of the mesh impinging on the catheter tip during deployment as the portion of the mesh 1200 being deployed will follow the distal offset and thus "get out of the way" of the more proximal portion of the mesh 1200 as it is being deployed. The double offset feature also reduces the likelihood of compartmentalization (i.e., when the embolic filler material, such as coils, are deployed in a single location and not uniformly distributed throughout the aneurysm cavity), as the offset ends are less likely to overlap within the aneurysm. Any of the meshes detailed herein (e.g., mesh 100, mesh 300, mesh 1000, etc.) may also have offset end portions.

The mesh 1200 may be formed of a stent, a braid, a lattice, a weave, a fabric, a laser-cut sheet, and/or any other suitable porous structure. In some embodiments, the mesh 1200 is not a porous structure, such as a flexible metal or plastic sheet. The mesh 1200 may comprise any of the meshes described elsewhere herein, such as mesh 100, mesh 300, and mesh 1000. Likewise, the coil 150 of the occlusive device 120 can be any of the coils described herein. In some embodiments, the device 120 comprises only the mesh 1200 and does not include the coil 150.

Figure 14:
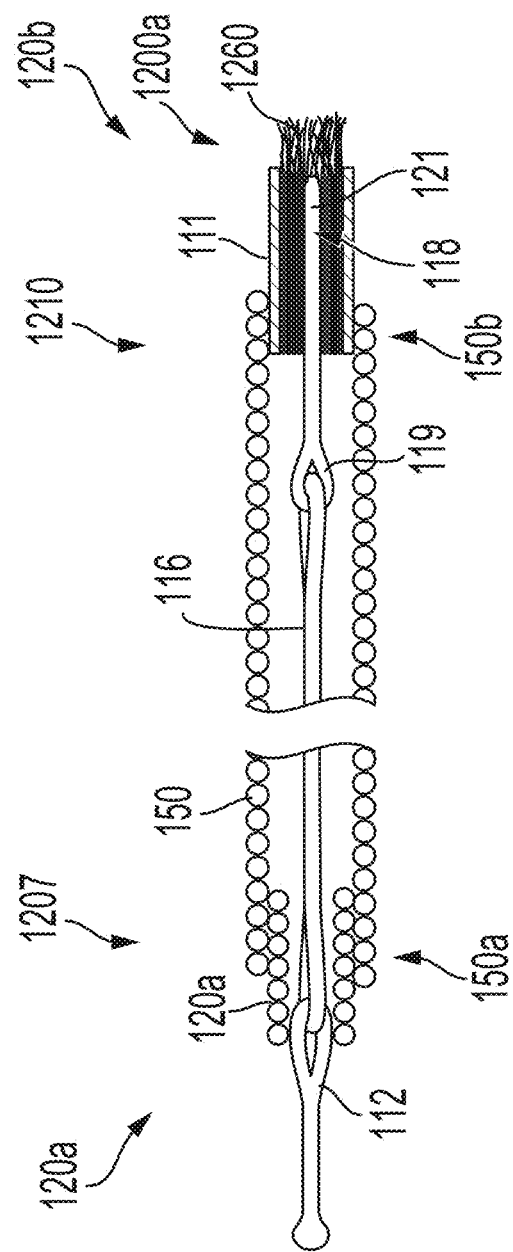
FIG. 14 is a cross-sectional view of a proximal joint and an intermediate joint of an occlusive device of the present technology.

FIG. 14 is a schematic illustration showing the proximal and intermediate joints 1207, 1210 of the occlusive device 120. As shown in FIG. 14, the intermediate joint 1210 may be configured to flex, bend, twist, rotate, or otherwise articulate such that the distal end 150b of the coil 150 may move and be positioned at an angle relative to the proximal end 1200a of the mesh 1200. Similar to intermediate joint 110, intermediate joint 1210 may comprise the distal end portion 150b of the coil 150, a proximal end portion of the band 111, and at least a portion of connector 118. Unlike intermediate joint 110, however, intermediate joint 1210 does not include a distal securing element 120b and instead the distal end portion of the coil 150b extends over and surrounds a proximal end portion of the band 111. Thus, at least at the joint 1210, in some embodiments the coil 150 may have a greater diameter than that of the band 111. In some embodiments, the band 111 and proximal portion of the mesh 1200a within (i.e., proximal portion of curved tail 1260) may be crimped to a smaller diameter (for example, 50% of its diameter in the configuration of FIG. 1D), then swaged to smoothen any edges that may catch on the catheter lumen or distal opening during delivery. The coil 150 may then be welded to the band 111 to secure the connection. The positioning of the coil 150 over the band 111 allows for the removal of the distal securing element 120b, which reduces the length and diameter of the joint, thereby making the joint 1210 more flexible than joint 1210. For example, the straight portion of the joint 1210 may be less than or equal to 2 mm, less than or equal to 1.5 mm, or less than or equal to 1 mm.

Moreover, as shown in FIG. 14, the coupling region between the distal end portion of the intermediate member 116 and the coupling region 119 of the connector 118 may be disposed within the lumen of the coil 150. In some embodiments, the coupling region between the intermediate member 116 and the coupling region 119 may be disposed within the band 111.

Although mesh 1200 is shown having intermediate joint 1210, mesh 1200 may include other joints or coupling means, such as joint 110 or other configurations. For example, in some embodiments the distal end portion 150b of the coil 150 may be disposed within the lumen of the band 111. In those embodiments where the distal end portion 150b of the coil 150 and the proximal end portion 1200a of the mesh 1200 (and/or a component thereof, such as band 111) are co-extensive with one another, the joint may include an additional securing and/or stabilization member (such as securing element 120a or securing element 120b) that extends between the overlapping coil and mesh.

Figure 15A:
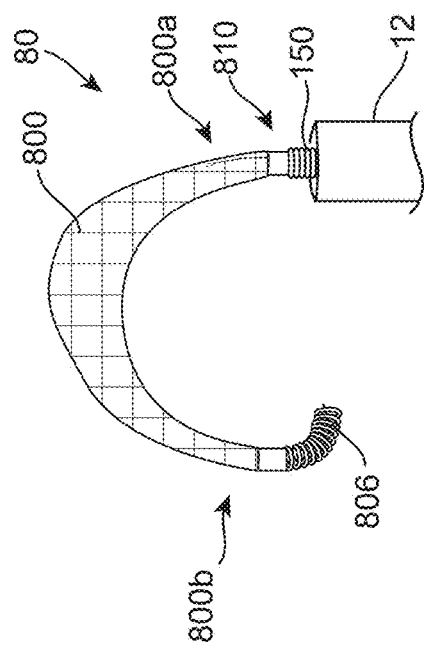
FIG. 15A depicts an occlusive device of the present technology in a partially deployed configuration.
Figure 15E:
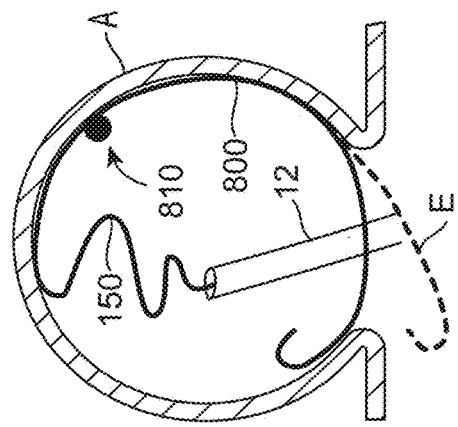
FIGS. 15B-15F illustrate schematically a method of positioning the occlusive device of FIG. 15A over the neck of an aneurysm.
Figure 15D:
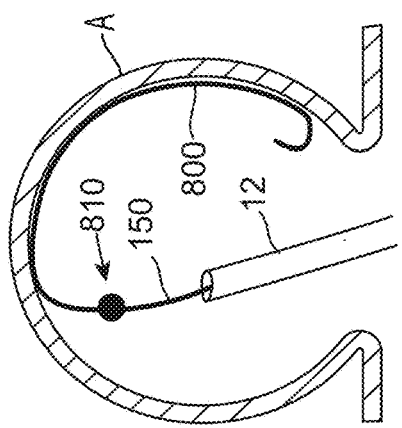
Figure 15C:
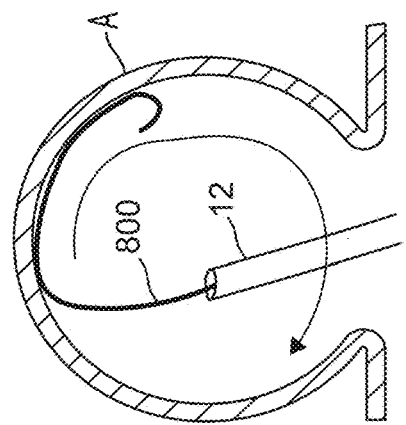
Figure 15B:
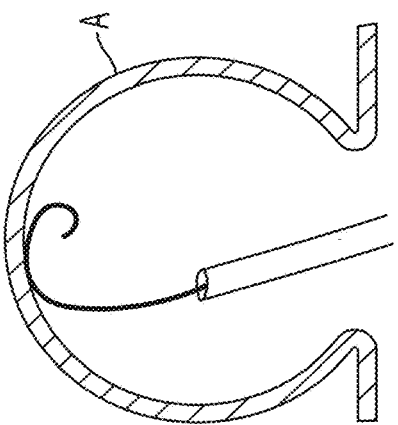

In some cases it may be beneficial to include a guide near the intermediate joint of the occlusive devices herein to aid positioning of the mesh over the neck of the aneurysm. Without a guide, the physician may have to push the device around the dome of the aneurysm to position the mesh over the neck of the aneurysm. For example, FIG. 15A is a side view of the mesh 800 of the occlusive device 80 of FIG. 8A in a partially deployed state, shown being released from a delivery catheter 12 (such as a microcatheter) outside of the constraints of an aneurysm to better view its preset shape. In this embodiment, the occlusive device 80 and/or mesh 800 does not include a guide at its joint 810. (It will be appreciated that in other embodiments the mesh 800 may include a guide.) In FIG. 15A, the occlusive device 80 is shown at the moment when the joint 810 is clearing the distal end of the delivery catheter 12 and the distal end of the coil 150 is beginning to protrude.

Figure 15F:
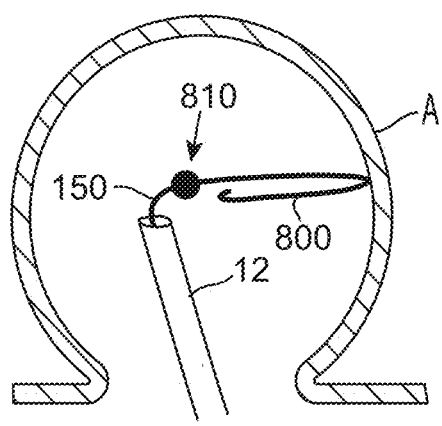

As shown schematically in FIGS. 15B to 15E, to position the mesh 800 over the neck of the aneurysm A, often times the physician must rely on pushing the device 80 around the dome of the aneurysm A. While this method can be successful (as shown in FIGS. 15B to 15E) and the shape of the meshes of the present technology help bias the device into the correct positioning, pushing the device around the dome often requires several attempts as it is highly dependent on the positioning of the microcatheter and the anatomy/curvature of the aneurysm sac, and their respective impacts on the shape of the mesh 800 and direction of rotation about the dome that the device 80 takes. Proper positioning across the neck can be especially challenging in small neck aneurysms where the turn radius is tight, which may cause the mesh 800 to herniate into the parent vessel rather than cross the neck (as depicted by the example herniating mesh E in FIG. 15E). Another common example of a deployment that may require repositioning is shown in FIG. 15F. In some cases the release of the joint 810 may orient the mesh 800 such that it rotates around a plane within the aneurysm A that does not cover the neck. In these and other scenarios, the physician would need to pull all or some of the device 80 back into the delivery catheter 12 and re-deploy until the proper orientation of the mesh is achieved.

Figure 16A:
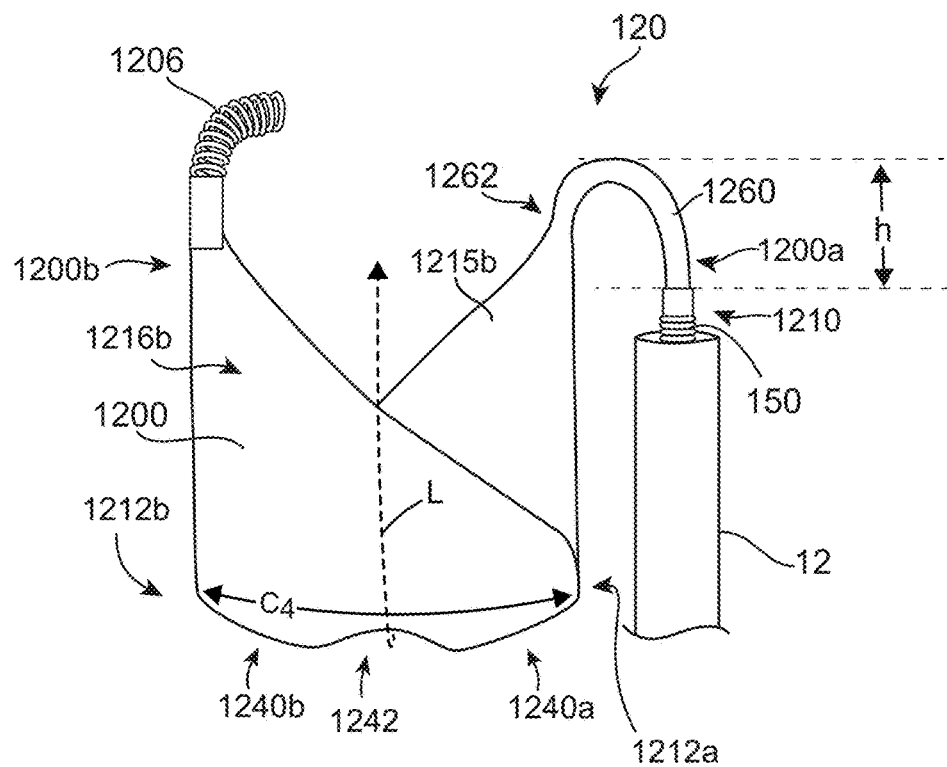
FIGS. 16A and 16B are end and top views, respectively, of a partially deployed occlusive device having a tail in accordance with the present technology.
Figure 16B:
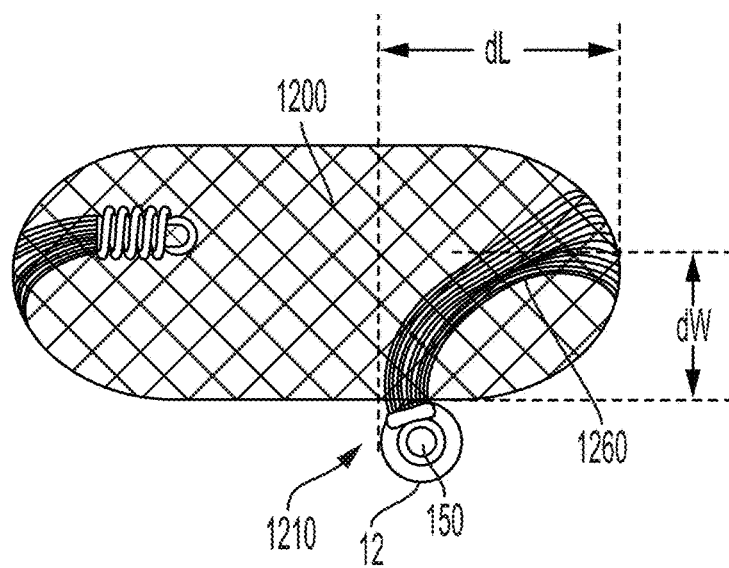

FIGS. 16A and 16B are end and top views, respectively, of the occlusive device 120 described with respect to FIGS. 12A-14 that includes a guide in the form of curved tail 1260. (It will be appreciated that a guide, including that in the form of a curved tail, may be included in any of the occlusive devices described herein, including occlusive devices 10, 30, 80, and 101.) In FIGS. 16A and 16B, the occlusive device 120 is in a partially deployed state, shown being released from a delivery catheter 12 (such as a 0.017 inch microcatheter) outside of the constraints of an aneurysm to better view its preset shape. In FIGS. 16A and 16B, the occlusive device 120 is shown at the moment when the joint 1210 is clearing the distal end of the delivery catheter 12 and the distal end of the coil 150 is beginning to protrude.

The guides of the present technology, including curved tail 1260, are configured to position the meshes disclosed herein (such as mesh 1200) over the neck of the aneurysm, thereby reducing the complexity and time required to fully deploy the occlusive device (such as occlusive device 120). The guides of the present technology reduce the need to rely on the dome of the aneurysm to guide the mesh over the neck. Less reliance on the aneurysm wall during delivery is also beneficial for treating amorphous/multi-lobe aneurysms, as well as ruptured aneurysms whose wall might not allow the mesh to "ride" on. Details regarding the structure of the guides are discussed below with reference to FIGS. 16A to 17B, and details regarding the deployment of the guides are discussed below with reference to FIGS. 18A to 18F.

Figure 17A:
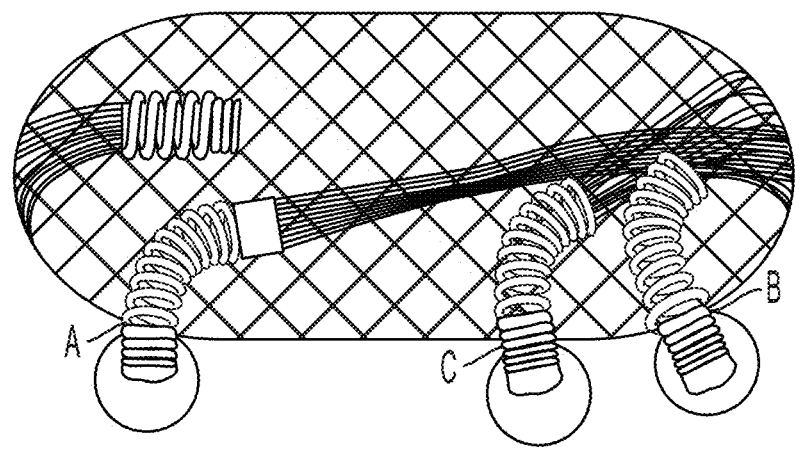
FIGS. 17A and 17B are schematic illustrations of a mesh of the present technology showing different tail configurations.
Figure 17B:
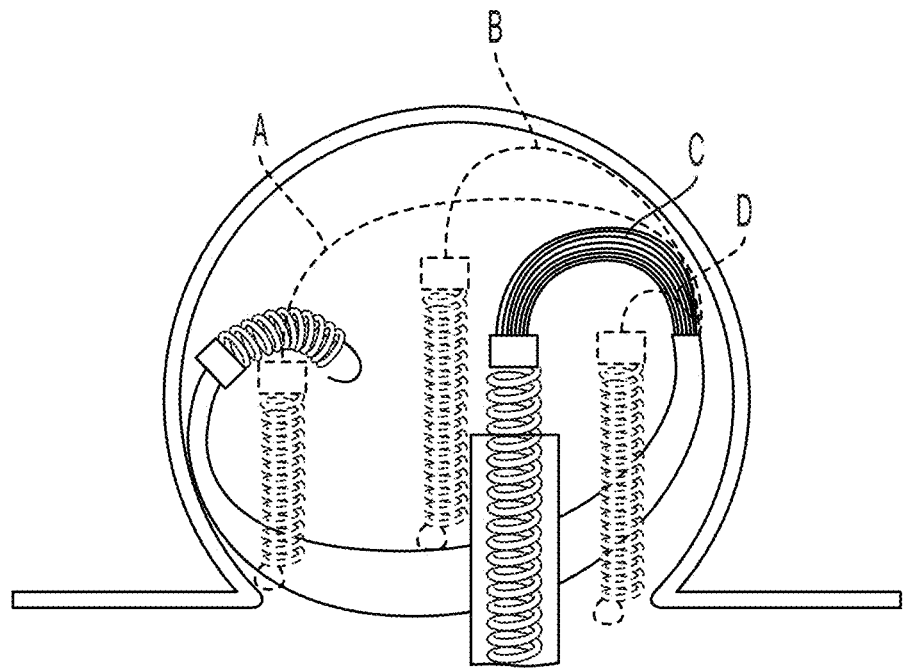

As shown in FIGS. 16A and 16B, the curved tail 1260 can be configured to position a lateral edge 1212a or 1212b of deployed mesh as close as possible to the delivery catheter 12 so that the mesh does not interfere with the deployment of the coil 150, and so that the angle of the tail 1260 does not push the mesh away from the neck laterally or away from the neck towards a side of the aneurysm. This positioning with respect to the delivery catheter 12 is also beneficial to ensure the mesh 1200 does not interfere with the deployment of the coil 150 into the aneurysm cavity between the neck and the dome. Proper positioning of the mesh 1200 within the aneurysm may be achieved by one or more of a height h (FIG. 16A), a longitudinal length dL (FIG. 16B), a lateral length dW (FIG. 16B), and a radius of curvature of the curved tail 1260 (as shape set and without any deformation caused by deployment). As discussed below with reference to FIGS. 18A-18F, when released, the preset curve of the tail 1260 causes the mesh 1200 to "flip around" or "drop in" at an angle relative to the more proximal portion of the occlusive device 120 such that the concave surface of the mesh 1200 faces the dome of the aneurysm and the convex surface of the mesh 1200 is positioned across the neck of the aneurysm. This positioning is achieved upon release of the tail 1260 and without having to push the mesh 1200 around the wall of the aneurysm. FIGS. 17A and 17B, for example shown different configurations for the tail 1260 in accordance with the present technology.

FIGS. 18A-18F illustrate a method of positioning the occlusive device 120 within an aneurysm A having a neck N open to a blood vessel V in accordance with an embodiment of the present technology. The occlusive device 120 is intravascularly delivered to a location within a blood vessel lumen PV adjacent a target aneurysm A (such as a cerebral aneurysm) in a low-profile configuration (not shown) within a delivery catheter 12. The occlusive devices of the present technology are configured to be delivered through a microcatheter as small as 0.017 inches, which enables delivery of the occlusive devices to the smaller, more distal blood vessels. This is in contrast to conventional intrasaccular devices which typically require a microcatheter of at least 0.021 inches.

Figure 18C:
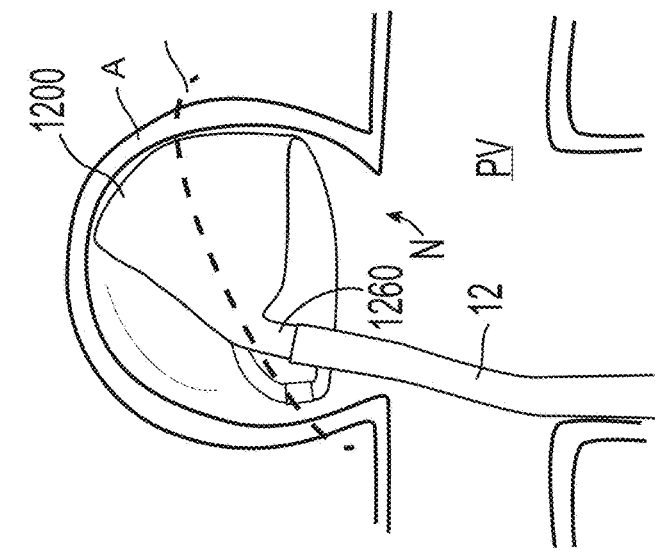
FIGS. 18A-18F illustrate an example method for delivering an occlusive device of the present technology to a cerebral aneurysm.
Figure 18B:
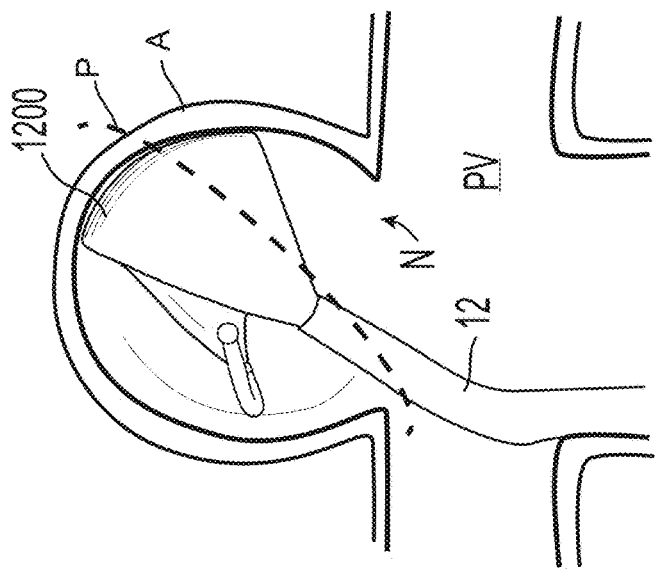
Figure 18A:
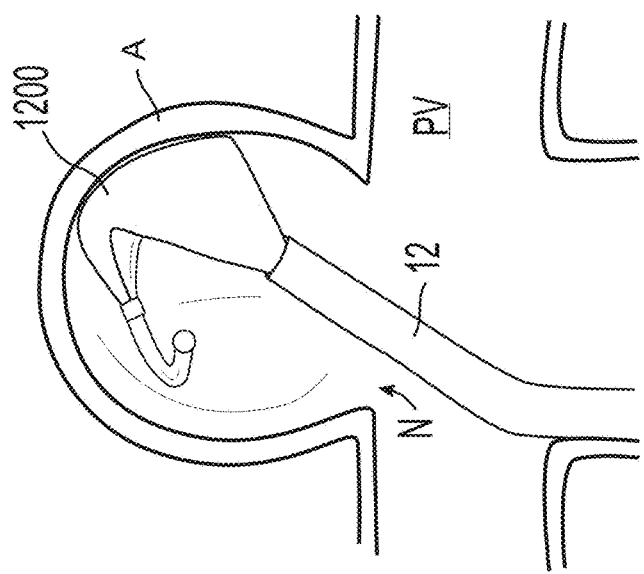
Figure 18F:
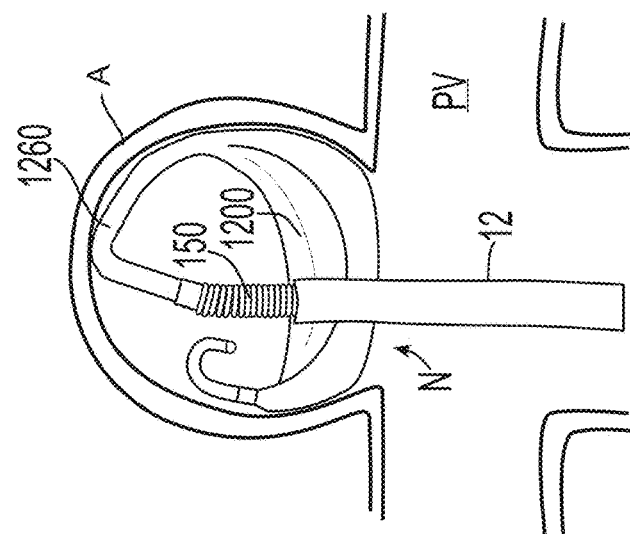
Figure 18E:
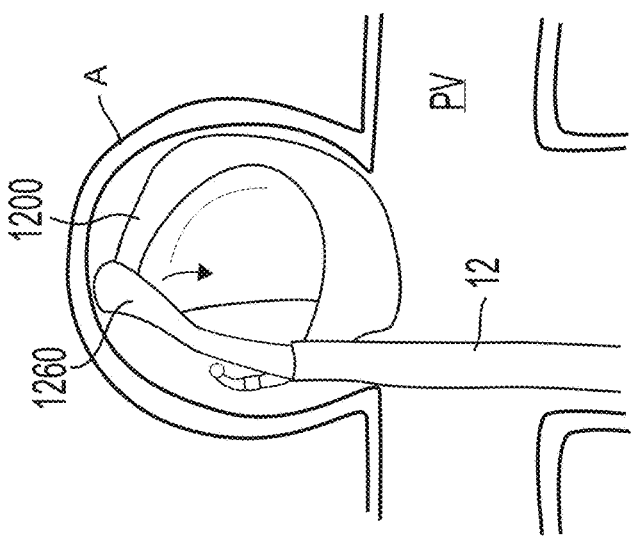
Figure 18D:
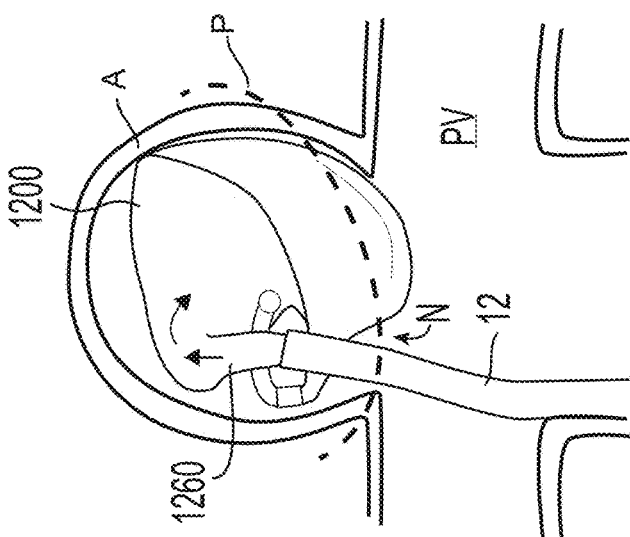

The distal portion of the delivery catheter 12 is then advanced through the neck N of the aneurysm A to an interior region of the aneurysm A. As shown in FIGS. 18A and 18B, the occlusive device 120 is then deployed by pushing the occlusive device 120 distally through the distal opening of the delivery catheter 12 towards a wall of the aneurysm A. Initially, before the tail 1260 is released, the mesh 1200 contacts the aneurysm wall and begins to slide around the curved inner surface of the aneurysm A. As illustrated by FIGS. 18C-18F, however, as the tail 1260 is released, the preset curve of the tail 1260 forces the mesh 1200 to "flip around" or "drop in" at an angle relative to the more proximal portion of the occlusive device 120 such that the concave surface of the mesh 1200 faces the dome of the aneurysm and the convex surface of the mesh 1200 is positioned across the neck of the aneurysm.

Then, with the tip of the delivery catheter still within the aneurysm sac, the occlusive device 120 may be detached from the delivery member (such as a pusher member) via one or more of the detachment mechanisms described elsewhere herein.

In some cases, the physician may choose to deliver additional coils or embolic material (such as a liquid embolic) to the aneurysm. In these scenarios, the physician may withdraw the pusher member from the delivery catheter and, while maintaining the tip of the delivery catheter within the aneurysm sac (beyond the mesh positioned across the neck), the physician may push the additional embolic material through the delivery catheter and into the aneurysm.

Although the foregoing embodiments are described with respect to a single continuous mesh and a single coil, these and other embodiments of the occlusive device 10 may include more than one mesh and/or more than one coil. The mesh(es) and coil(s) may be arranged end-to-end (as described above), or one or more of the mesh(es) or coil(s) may be arranged in parallel or otherwise overlapping along at least a portion of their lengths. The mesh(es) and coil(s) may be alternating and/or the occlusive device 10 may include two or more consecutive mesh(es) and/or two or more consecutive coil(s).

Example Methods of Manufacturing

Figure 19A:
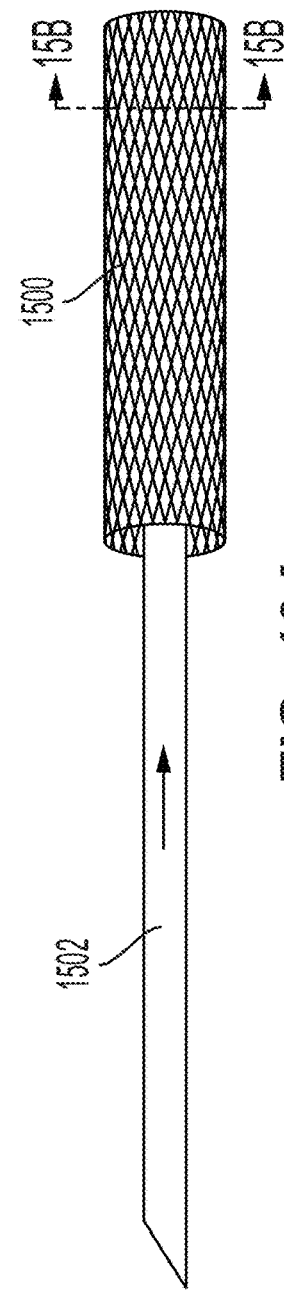
FIGS. 19A-19E show an example method for flattening a tubular mesh in accordance with the present technology.
Figure 19B:
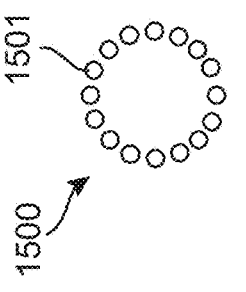

FIGS. 19A-19B depict an example method for forming a contoured mesh in accordance with the present technology. As previously discussed, in some embodiments the mesh of the occlusive device may be formed of a tubular mesh that has been flattened and contoured to produce the novel shapes of the present technology. FIGS. 19A-19E depict one example method for flattening a tubular mesh prior to contouring the mesh in accordance with the present technology. As shown in FIGS. 19A and 19B, the method may begin with inserting a flat mandrel 1502 into the lumen of a tubular mesh 1200. The tubular mesh 1500 may, for example, comprise a plurality of braided filaments 1501, as discussed elsewhere herein. In some embodiments, the mesh 1500 may have other forms, such as a laser-cut stent. Moreover, while the mandrel 1502 shown in FIG. 19A has a rectangular shape, in some embodiments the mandrel 1502 may have other shapes. Preferably the mandrel has a substantially constant thickness so that the resulting mesh layers have substantially the same contouring and thus follow one another.

Figure 19C:
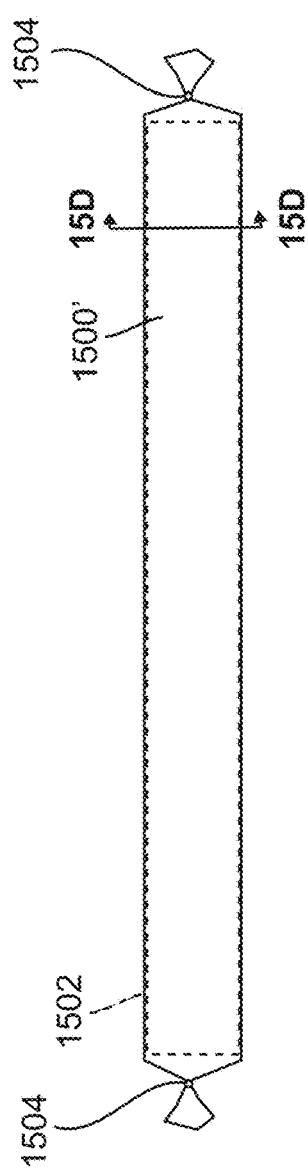
Figure 19D:
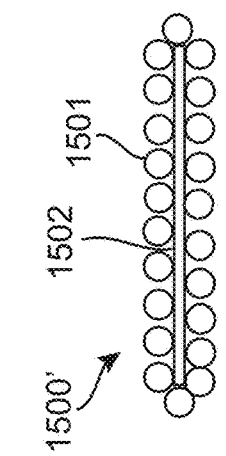
Figure 19E:
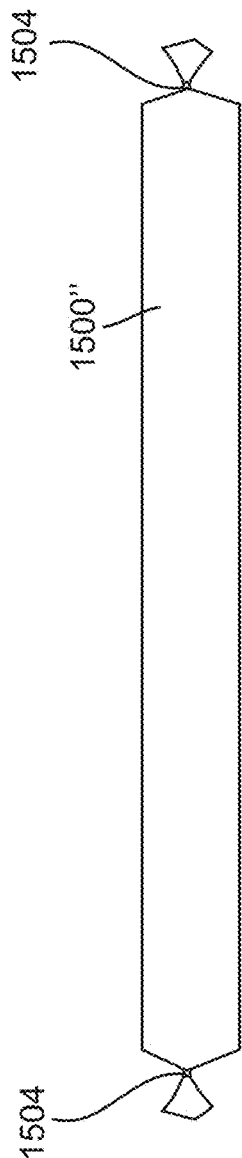

In any case, as shown in FIGS. 19C and 19D, the method may include stretching the mesh 1500 over the flat mandrel 1502 so that the mesh 1500 conforms to the flattened shape of the mandrel. The mesh 1500 may be positioned on the mandrel 1502 such that the distal and/or proximal ends of the mesh 1500 extend beyond the distal and/or proximal ends of the mandrel 1502. Should the mesh 1500 be positioned such that the ends of the stretched mesh 1500' go beyond the ends of the mandrel 1502, a coupling element 1504 may be employed to hold the ends of the stretched mesh 1500' together. The coupling element 1504 may be, for example, a wire tie, adhesive, a marker band, and/or other suitable coupling elements. The mandrel 1502 then holds the stretched mesh 1500' in the desired shape or configuration (here, straight with a constant thickness) while subjected to a heat treatment such that the strands of the mesh 1500' assume or are otherwise shape-set to the contour of the mandrel 1502. When released from a compressed state, the resulting mesh 1500" will self-expand and return to the heat-set configuration, as shown in FIG. 19E.

Figure 20:
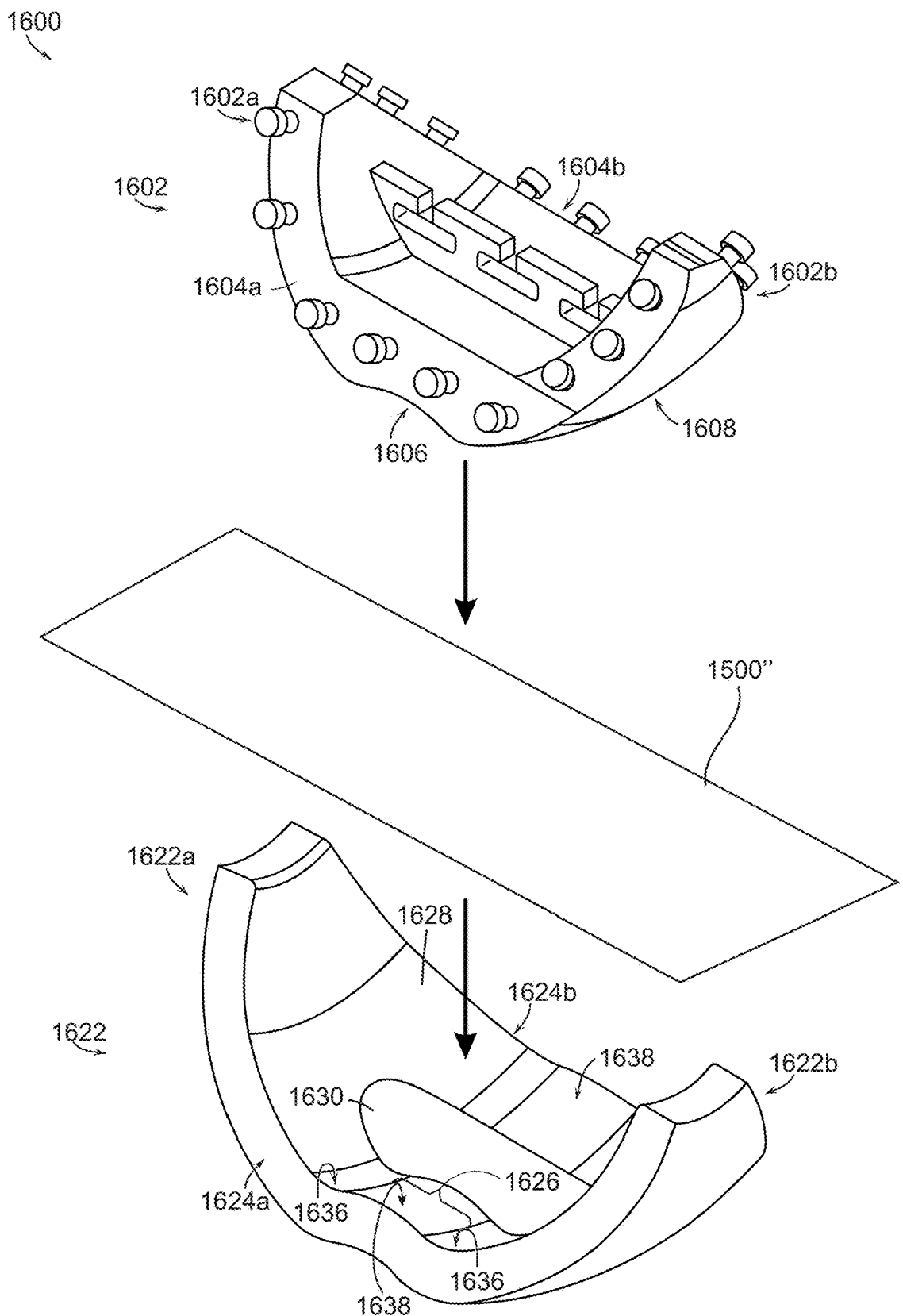
FIG. 20 shows a forming assembly configured in accordance with the present technology.

To impart additional contouring on the flattened, two-layer mesh 1500", the mesh 1500" may be heat set an additional time while being held in the desired shape. FIG. 20 illustrates one example of a forming assembly 1600 (or "assembly 1600") for forming a contoured mesh of the present technology, shown in an unassembled state. As shown, the assembly 1600 may comprise a first member 1602 and a second member 1622 configured to mate with the first member 1602. The first and second members 1602 and 1622 may be configured to receive the mesh strip 1500" therebetween in order to hold the mesh 1500" in a desired shape during the heat set.

Figure 21A:
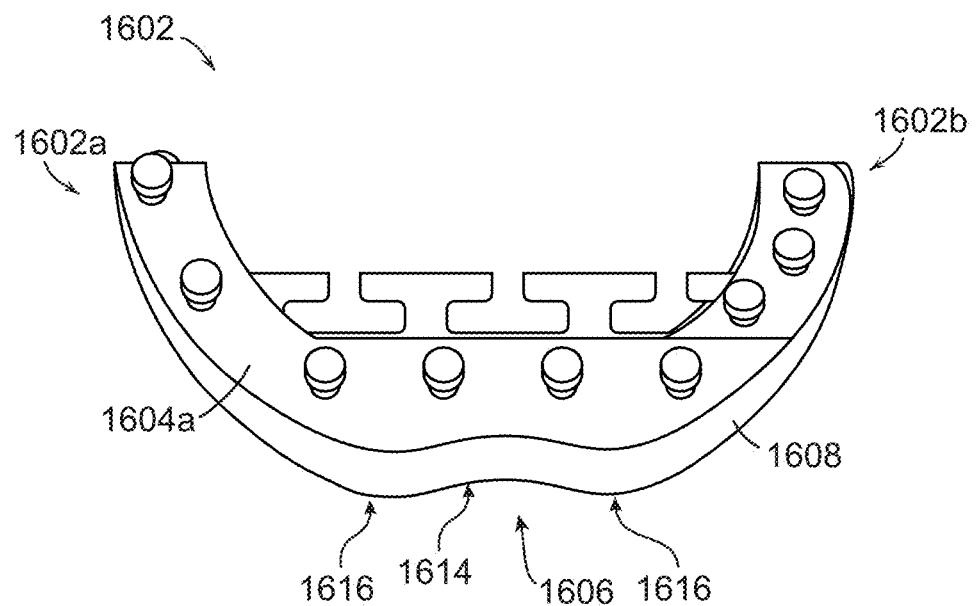
FIGS. 21A and 21B are side and end views, respectively, of the first member of the forming assembly of FIG. 20.
Figure 21B:
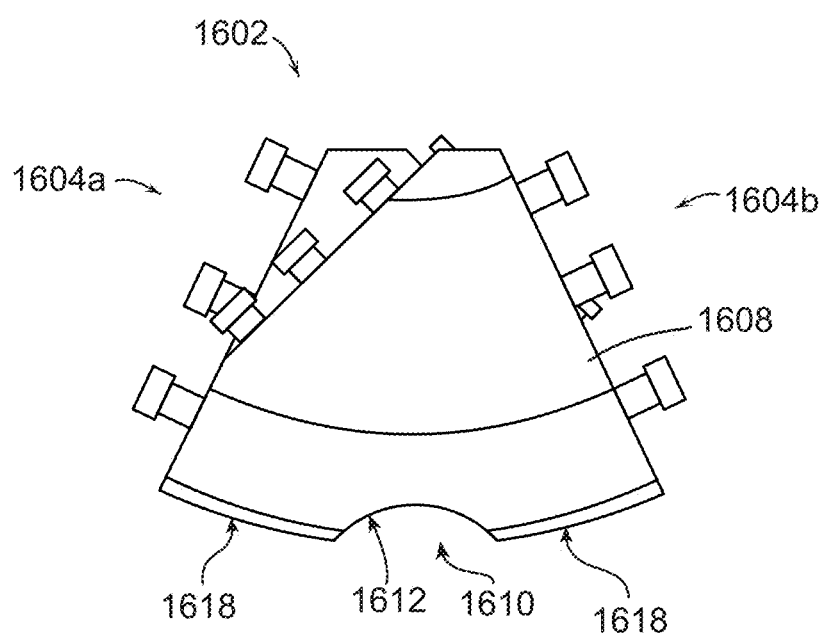

FIGS. 21A and 21B are side and end views, respectively, of the first member 1602 of the assembly 1600. Referring to FIGS. 20-21B together, the first member 1602 may comprise a mating surface 1608 bound by a first side edge 1604*a*, a second side edge 1604*b* opposite the first side edge 1604*a* along a width of the surface 1608, a first end 1602*a*, and a second end 1602*b* opposite the first end 1602*a* along a longitudinal axis of the surface 1608. The mating surface 1608 may be generally curved along its longitudinal axis between the first and second ends 1602a and 1602b, and the mating surface 1608 may be generally curved along its width between the first and second side edges 1604a and 1604b. During heat set of the mesh 1500″, the mating surface 1608 may be proximate the side of the mesh 1500″ that is ultimately configured to face the aneurysm cavity when the occlusive device is positioned within the aneurysm.

In some embodiments, the first member 1602 may comprise a longitudinal divot 1610 (see FIG. 21B) extending longitudinally along at least a portion of the length of the first member 1602. The longitudinal divot 1610 may be defined by a recessed portion 1612 of the mating surface 1608 and positioned between two shoulder portions 1618. In some embodiments, the first member 1602 comprises multiple longitudinal divots. In particular embodiments, the first member 1602 does not include a longitudinal divot. In such embodiments, the curvature of the mating surface 1608 along its width is generally constant.

In some embodiments, the first member 1602 may comprise a lateral divot 1606 (see FIGS. 20 and 21A) and lateral protrusions 1616 that extend laterally along at least a portion of the width of the first member 1602 between the first and second side edges 1604a and 1604b. The lateral divot 1606 may be defined by a recessed portion 1614 of the mating surface 1608. In some embodiments, the first member 1602 comprises multiple lateral divots and/or protrusions. In particular embodiments, the first member 1602 does not include a lateral divot. In such embodiments, the curvature of the mating surface 1608 along its length is generally constant.

Depending on the desired shape, the first member 1602 may comprise one or more lateral divots and/or protrusions and no longitudinal divots, one or more longitudinal divots and no lateral divots or protrusions, or one or more lateral divots and/or protrusions and one or more longitudinal divots. In the embodiment depicted in FIGS. 20-21B, the first member 1602 includes a lateral divot, two lateral protrusions, and a longitudinal divot. In such embodiments including one or more divots extending along the width and length of the surface 1608, the shoulders 1618 of the longitudinal divot 1610 may have a greater radius of curvature than the protrusions 1616 alongside the lateral divot 1614. In some embodiments, the shoulders 1618 of the longitudinal divot 1610 may have a lesser radius of curvature than the protrusions 1616 alongside the lateral divot 1614. In some embodiments, the respective radii of curvature of the shoulders 1618 and the protrusions 1616 may be substantially the same.

Figure 22A:
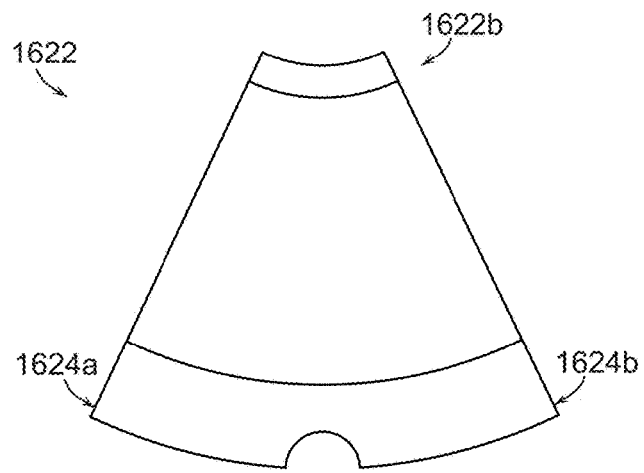
FIGS. 22A and 22B are end and side views, respectively, of the second member of the forming assembly of FIG. 20.
Figure 22B:
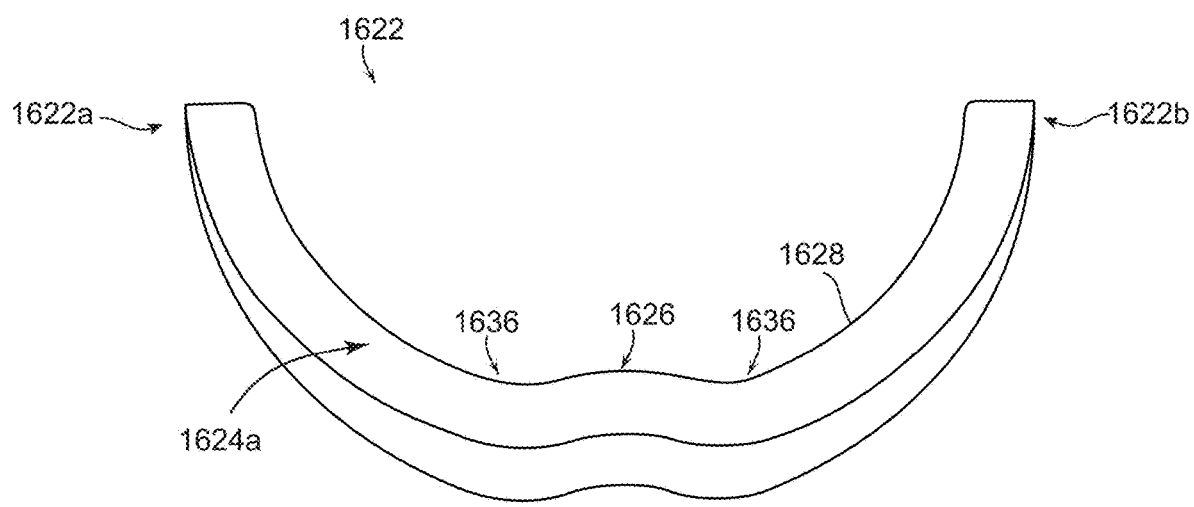

FIGS. 22A and 22B are end and side views, respectively, of the second member 1602 of the assembly 1600. Referring to FIGS. 20, 22A, and 22B together, the second member 1622 may comprise a mating surface 1628 bound by a first side edge 1624a, a second side edge 1624b opposite the first side edge 1624a along a width of the surface 1628, a first end 1622a, and a second end 1622b opposite the first end 1622a along a longitudinal axis of the surface 1628. The mating surface 1628 may be generally curved along its longitudinal axis between the first and second ends 1622a and 1622b, and the mating surface 1628 may be generally curved along its width between the first and second side edges 1624a and 1624b. During heat set of the mesh 1500″, the mating surface 1628 may be proximate the side of the mesh 1500″ that is ultimately configured to face the parent vessel when the occlusive device is positioned within the aneurysm.

In some embodiments, the second member 1622 may comprise a longitudinal protrusion 1630 (see FIG. 21B) extending longitudinally along at least a portion of the length of the second member 1622. The protrusion 1630 may extend in the direction of the general concavity of the second member 1622, and may be positioned between two shoulder portions 1638 (FIG. 20). In some embodiments, the second member 1622 comprises multiple longitudinal protrusions. In particular embodiments, the second member 1622 does not include a longitudinal protrusion. In such embodiments, the curvature of the mating surface 1628 along its width is generally constant.

In some embodiments, the second member 1622 may comprise a lateral protrusion 1626 (see FIGS. 19 and 21B) and lateral dips 1636 that extend laterally along at least a portion of the width of the second member 1622 between the first and second side edges 1624a and 1624b. In some embodiments, the second member 1622 comprises multiple lateral divots and/or protrusions. In particular embodiments, the second member 1622 does not include a lateral divot. In such embodiments, the curvature of the mating surface 1628 along its length is generally constant.

Depending on the desired shape, the second member 1622 may comprise one or more lateral protrusions and/or dips and no longitudinal protrusions, one or more longitudinal protrusions and no lateral dips or protrusions, or one or more lateral divots and/or protrusions and one or more longitudinal protrusions. In the embodiment depicted in FIGS. 20, 22A, and 22B, the second member 1622 includes a lateral protrusion, two lateral dips, and a longitudinal protrusion. In such embodiments including one or more divots extending along the width and length of the surface 1628, the shoulder portions 1638 of the longitudinal protrusion 1630 may have a greater radius of curvature than the dips 1636 alongside the lateral protrusion 1626. In some embodiments, the shoulder portions 1638 of the longitudinal protrusion 1630 may have a lesser radius of curvature than the dips 1636 alongside the lateral protrusion 1626. In some embodiments, the respective radii of curvature of the shoulder portions 1638 and the dips 1636 may be substantially the same.

In use, the flattened mesh 1500″ may be sandwiched between the respective mating surfaces 1608 and 1628 of the first and second members 1602 and 1622 such that the flattened mesh 1500″ conforms to the divots, dips, and protrusions of the surfaces 1608, 1628. The first and second members 1602 and 1622 may be fixed in place, and the entire assembly (including the mesh) may be heat-treated so that the resulting mesh assumes the heat-set shape. Mesh 1000 described herein with respect to FIGS. 10-11D is one example of a mesh of the present technology formed by the assembly 1600.

In some embodiments, the mesh may not be flattened prior to the contouring. For example, according to some methods of the present technology, the mesh may be positioned between the first and second members 1602, 1622 (or other forming apparatus) in a tubular and/or non-heat set state. As such, the single heat set simultaneously flattens and contours the mesh 1500″.

Figure 23:
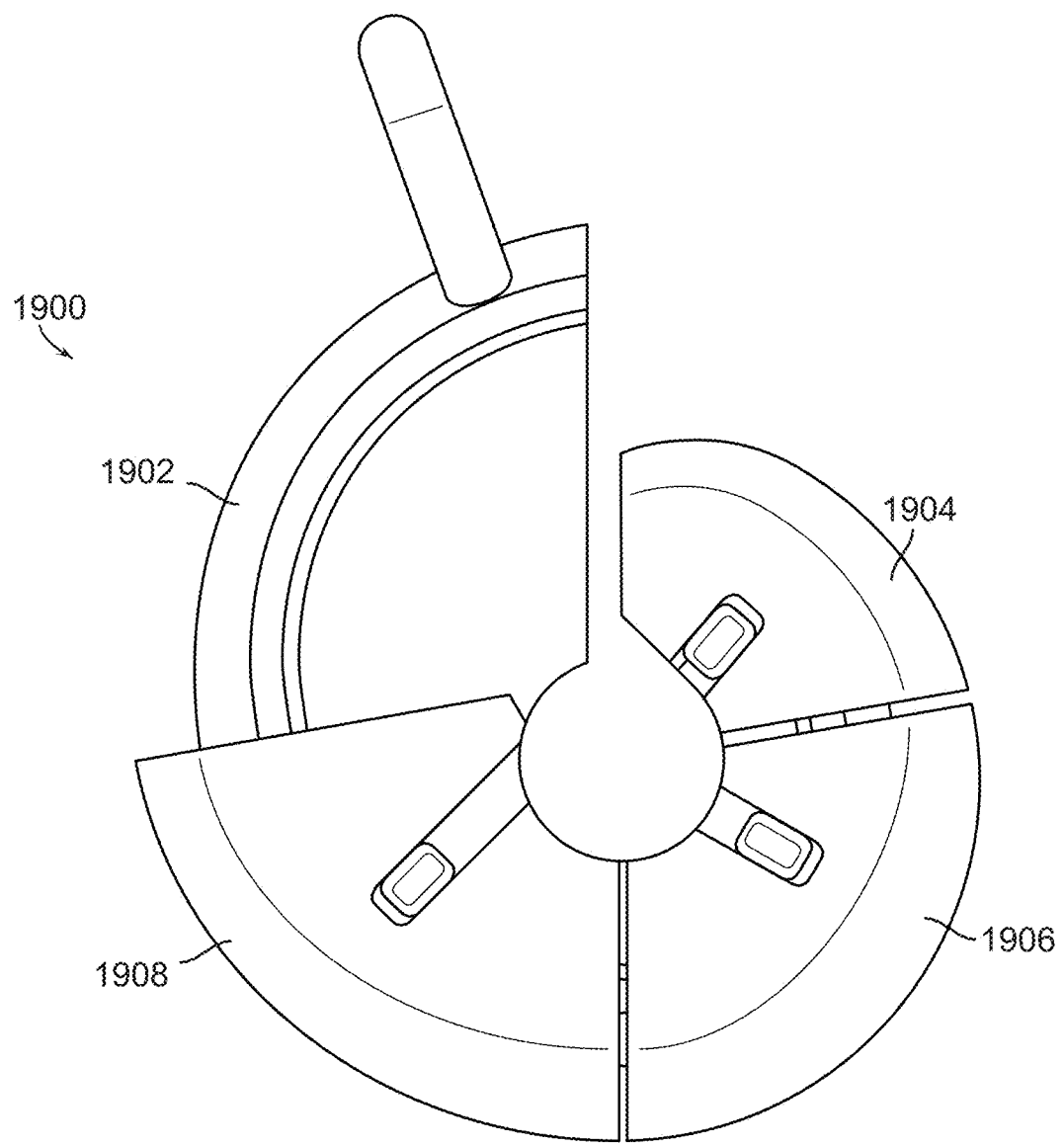
FIG. 23 is a top view of a forming assembly configured in accordance with the present technology.

FIG. 23 is a top view of a forming assembly 1900 (or "assembly 1900") configured in accordance with the present technology. In FIG. 23, the assembly 1900 is shown in an assembled configuration, without a mesh between the base and outer members. As shown, the assembly 1900 may comprise a base 1902 and first, second, and third outer members 1904, 1906, and 1908. Each of the outer members has a mating surface (not visible in FIG. 23) that matches the contour of the mating surface (not visible in FIG. 23) of the base 1900. In some embodiments, each of the mating surfaces of the outer members may have a different radius of curvature. In some embodiments, some or all of the mating surfaces have the same radii of curvature.

While FIG. 23 depicts an assembly 1900 comprising three outer members, in some embodiments the assembly 1900 may comprise more or fewer outer members. For example, in some embodiments, the assembly 1900 may comprise a single outer member having the same or different circumferential span as the combined outer members 1904, 1906, 1908. In some embodiments the assembly 1900 may comprise two outer members together having the same or different circumferential span as the combined outer members 1904, 1906, 1908. In some embodiments, the assembly 1900 may comprise four, five, six, seven, eight, or nine outer members, together having the same or different circumferential span as the combined outer members 1904, 1906, 1908.

According to some embodiments, the radius of curvature of the individual outer members may increase from the first outer member to the second outer member to the third outer member such that the radius of curvature of the first outer member 1904 is less than the radius of curvature of the second outer member 1906 which is less than the radius of curvature of the third outer member 1908. In some embodiments, the radius of curvature of the individual outer members may decrease from the first outer member to the second outer member to the third outer member such that the radius of curvature of the first outer member 1904 is greater than the radius of curvature of the second outer member 1906 which is greater than the radius of curvature of the third outer member 1908. In particular embodiments, the radius of curvature may vary along an individual one, some, or all outer member. In some embodiments, the radius of curvature may be generally constant along an individual one, some, or all of the outer members.

According to some embodiments, the radius of curvature of the individual portions of the mating surface of the base 1902 that correspond to the outer members 1904, 1906, 1908 may increase from a portion corresponding to where the first outer member mates to the portion corresponding to where the second outer member mates to the portion corresponding to where the third outer member mates such that the radius of curvature of the portion of the mating surface of the base 1902 corresponding to the first outer member 1904 is less than the radius of curvature of the portion of the mating surface of the base 1902 corresponding to the second outer member 1906 which is less than the radius of curvature of the portion of the mating surface of the base 1902 corresponding to the third outer member 1908. In some embodiments, the radius of curvature of the individual portions of the mating surface of the base 1902 that correspond to the outer members 1904, 1906, 1908 may decrease from a portion corresponding to where the first outer member 1904 mates to the portion corresponding to where the second outer member 1906 mates to a portion corresponding to where the third outer member 1908 mates such that the radius of curvature of the portion of the mating surface of the base 1902 corresponding to the first outer member 1904 is greater than the radius of curvature of the portion of the mating surface of the base 1902 corresponding to the second outer member 1906 which is greater than the radius of curvature of the portion of the mating surface of the base 1902 corresponding to the third outer member 1908. In particular embodiments, the radius of curvature may vary or remain generally constant along the mating surface of the base 1902.

Figure 24A:
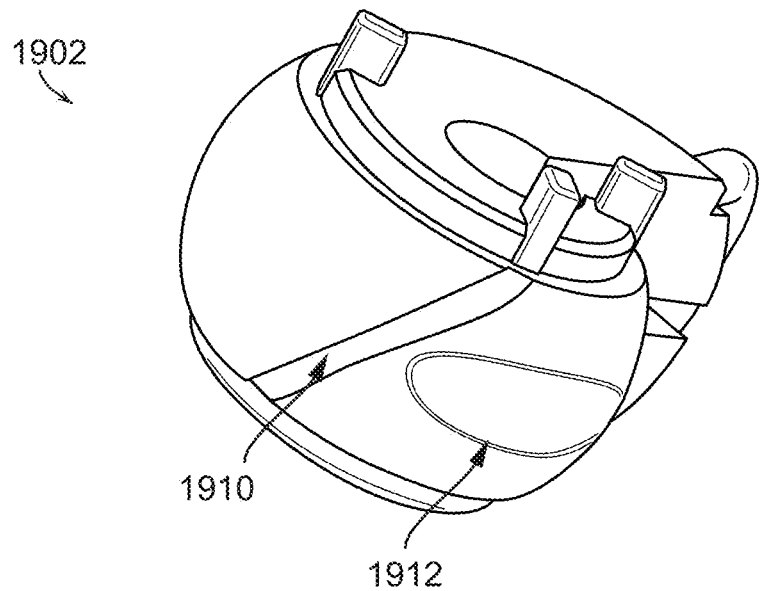
FIGS. 24A and 24B show a base of a forming assembly in accordance with the present technology.
Figure 24B:
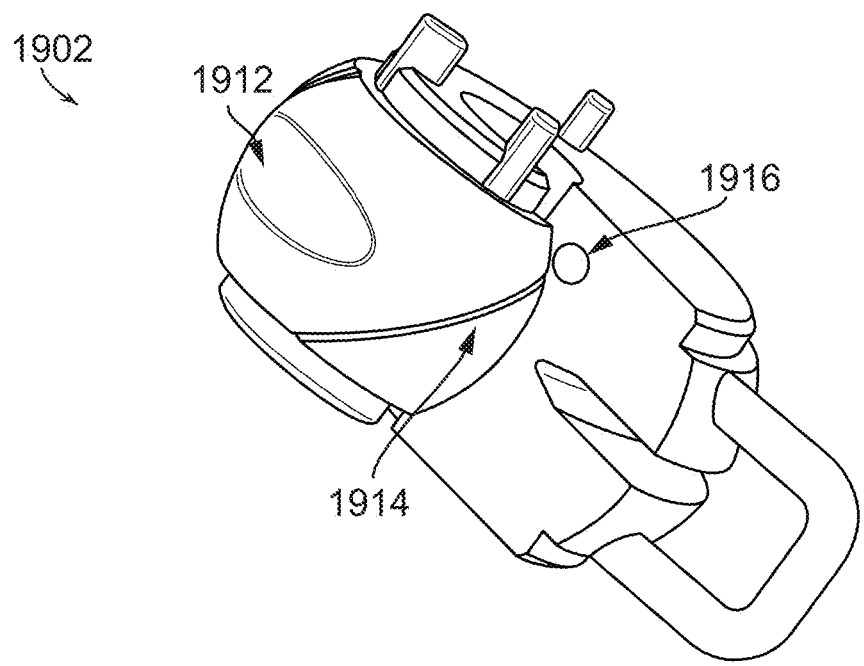

FIGS. 24A and 24B are isolated views of the base 1902 of the forming assembly 1900. As shown, the base 1902 may include first, second, and third (only visible in FIG. 24B) recesses/grooves 1910, 1912, 1914 in its mating surface. The first recess 1910 may extend diagonally across the width of the surface. During the shape setting process, a flattened mesh (such as flattened mesh 1500") may be positioned on the base 1902 such that a side edge of the mesh is forced to sit within or along the diagonal groove 1910 (see FIG. 27A) (e.g., via compressive forces and/or the use of adhesives), thereby forming one of the tapered portions (such as the proximal tapered portion). The second recess 1912 may extend generally parallel with the circumference of the base 1902 and may have a width that tapers towards its ends, as shown in FIG. 24B. In some embodiments, the second recess 1912 may have a generally constant width (not shown). The second recess 1912 may correspond to a longitudinal divot in the mesh, such as that in mesh 800 and mesh 1200. The third recess 1914 may extend diagonally across the width of the surface. The first and third grooves 1910, 1914 may extend generally parallel to one another and/or wrap around the surface in the same direction, or the grooves 1912, 1914 may extend in different directions. During the shape setting process, a flattened mesh (such as flattened mesh 1500") may be positioned on the base 1902 such that a side edge of the mesh is forced to sit within or along the diagonal groove 1914 (e.g., via compressive forces and/or the use of adhesives), thereby forming the other of the tapered portions (such as the distal tapered portion). The base 1902 may further include a channel 1916 through which the end of the mesh extending from the tapered portion may be threaded.

Figure 25:
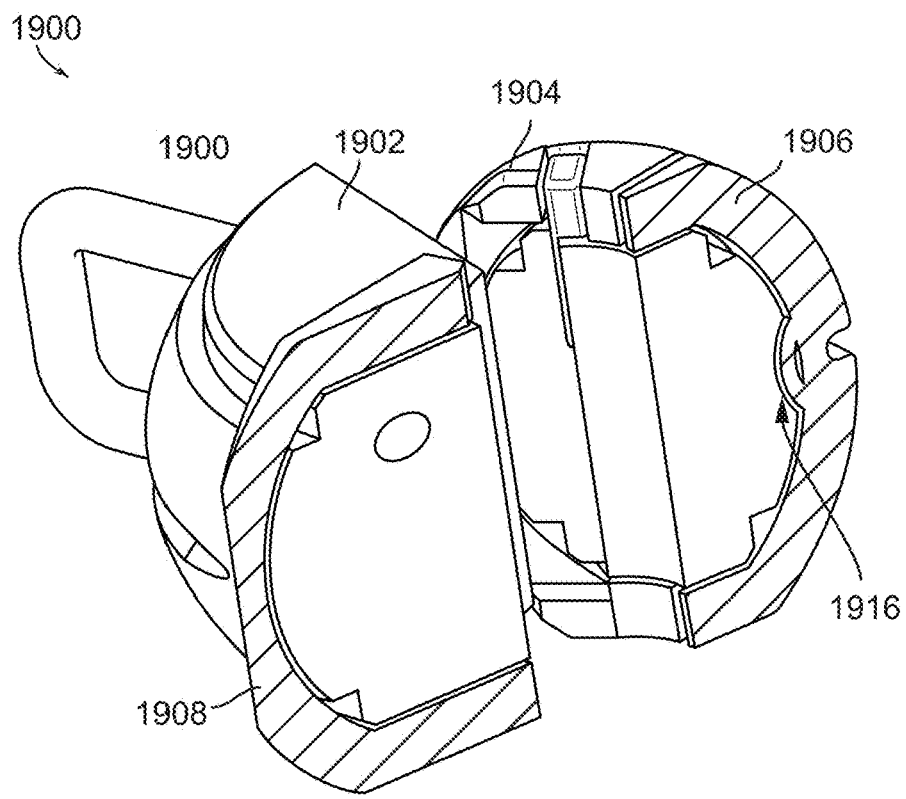
FIG. 25 is an isometric cross-sectional view of the forming assembly in an assembled configuration in accordance with the present technology.
Figure 26:
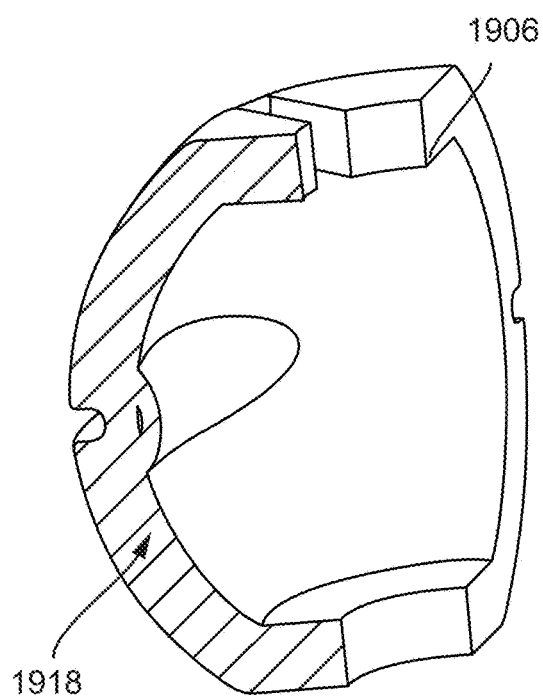
FIG. 26 is an isolated, isometric view of the second outer member of the forming assembly shown in FIG. 23.

FIG. 25 is an isometric cross-sectional view of the forming assembly 1900 in an assembled configuration. FIG. 26 is an isolated, isometric view of the second outer member 1906 of the forming assembly 1900. As best shown in FIGS. 24A-26 together, the mating surface of the base 1902 may have a circumferentially-extending recess and the mating surfaces of outer members have a corresponding protrusion along their mating surfaces (or vice versa). In some embodiments, the recess (or protrusion) extends along only the second outer member 1906 such that portions of the mesh laterally adjacent the resulting divot may have substantially the same radius of curvature (at least in those embodiments where the second outer member has a generally constant radius of curvature along its non-recessed mating surface). In some embodiments, the recess (or protrusion) extends along a portion of the second outer member 1906 and one or both of the first and third outer members 1906, 1908. In such embodiments, when each of the mating surfaces of the outer members (and corresponding portions of the mating surface of the base 1902) have different radii of curvature, the edges of the divot will thus having at least two different radii of curvature, one corresponding to the second outer member 1906 and the other(s) corresponding to the first 1904 and/or third 1908 outer members.

Figure 27A:
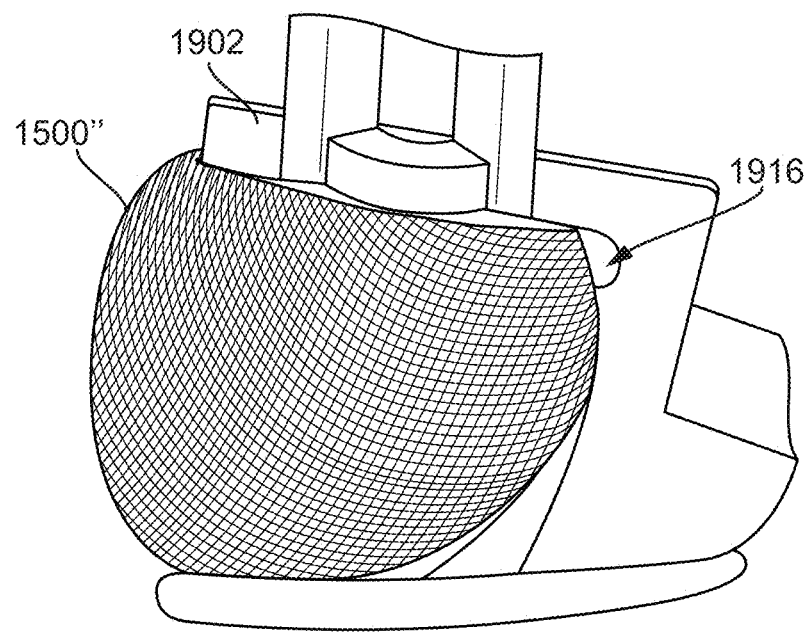
FIGS. 27A and 27B are different views showing a mesh shaped around the base of a forming assembly of the present technology, prior to application of an outer member.
Figure 27B:
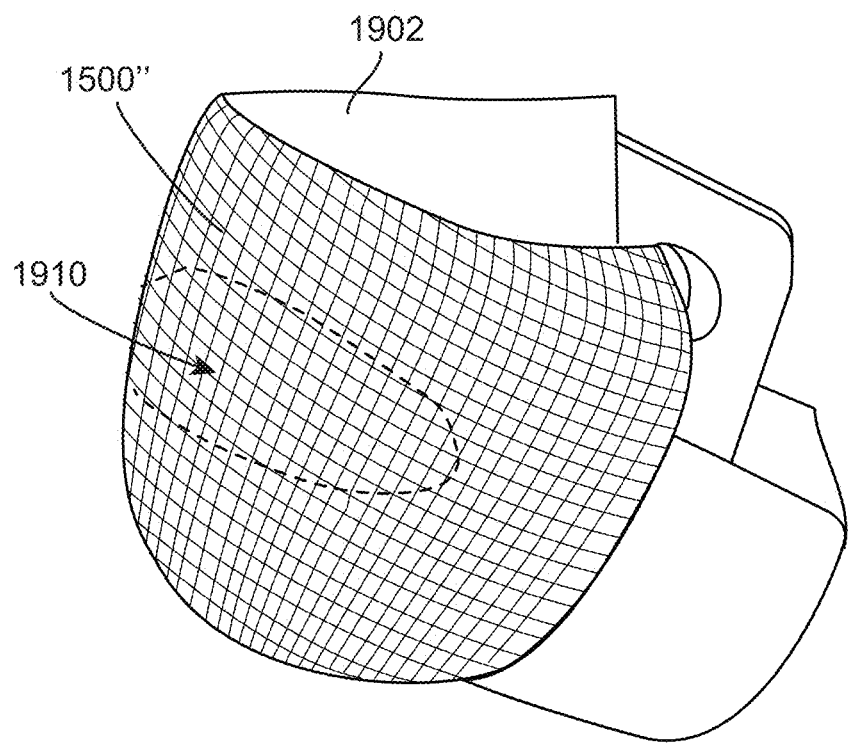
Figure 28A:
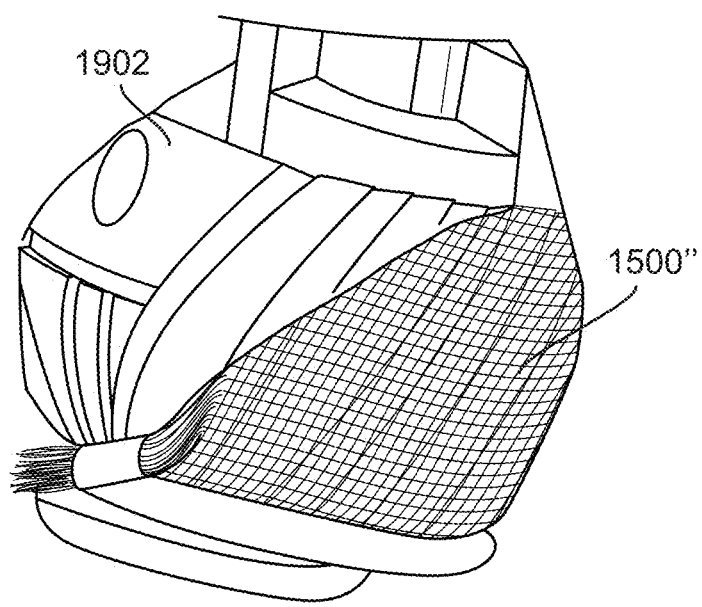
FIGS. 28A and 28B are different views showing a mesh shaped around the base of a forming assembly of the present technology, prior to application of an outer member.
Figure 28B:
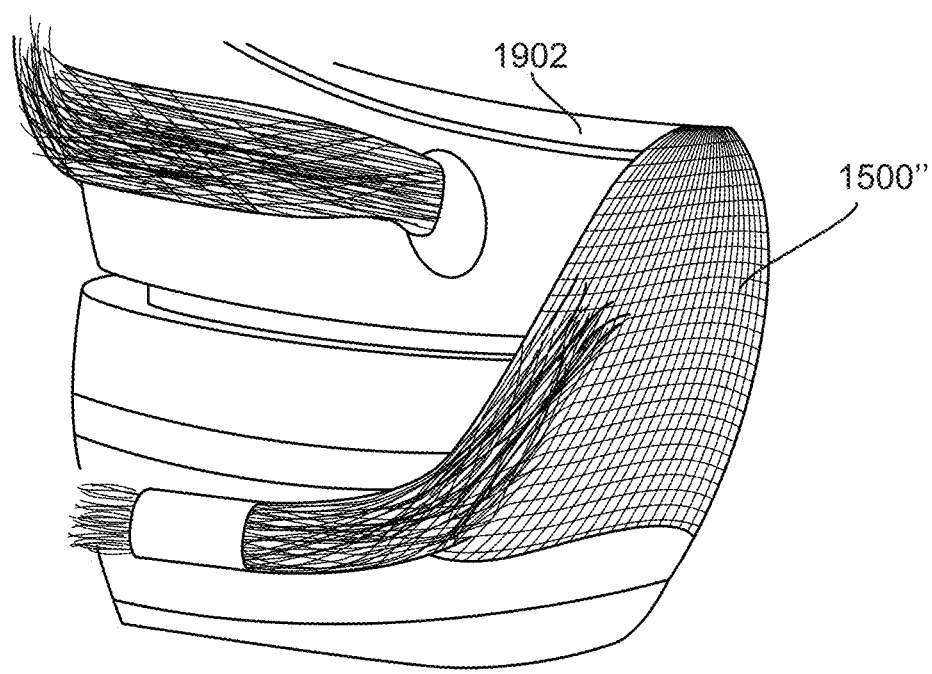

In use, a flattened mesh (such as flattened mesh 1500") may be sandwiched between the respective mating surfaces of the base 1902 and outer members 1904, 1906, 1908 such that the flattened mesh 1500" conforms to the contour of the surfaces, and such that the side edges of the proximal and distal portions of the mesh are angled towards in opposing directions. The first, second, and third outer members 1904, 1906, 1908 may be fixed in place, and the entire assembly (including the mesh) may be heat-treated so that the resulting mesh assumes the heat-set shape. FIGS. 27A-27B are different views showing a mesh shaped around the base of a forming assembly of the present technology, prior to application of an outer member. Mesh 800 described herein with respect to FIGS. 8A-9 and mesh 1200 described with respect to FIGS. 12A-12D are non-exclusive examples of meshes of the present technology that may be formed by the assembly 1900.

CONCLUSION

Although many of the embodiments are described above with respect to systems, devices, and methods for treating a cerebral aneurysm, the technology is applicable to other applications and/or other approaches. For example, the occlusive devices, systems, and methods of the present technology can be used to treat any vascular defect and/or fill or partially fill any body cavity or lumen or walls thereof, such as to treat parent vessel occlusion, endovascular aneurysms outside of the brain, arterial-venous malformations, embolism, atrial and ventricular septal defects, patent ductus arteriosus, and patent foramen ovale. Additionally, several other embodiments of the technology can have different states, components, or procedures than those described herein. It will be appreciated that specific elements, sub-structures, advantages, uses, and/or other features of the embodiments described can be suitably interchanged, substituted or otherwise configured with one another in accordance with additional embodiments of the present technology. A person of ordinary skill in the art, therefore, will accordingly understand that the technology can have other embodiments with additional elements, or the technology can have other embodiments without several of the features shown and described above with reference to FIGS. 1A-28B.

The descriptions of embodiments of the technology are not intended to be exhaustive or to limit the technology to the precise form disclosed above. Where the context permits, singular or plural terms may also include the plural or singular term, respectively. Although specific embodiments of, and examples for, the technology are described above for illustrative purposes, various equivalent modifications are possible within the scope of the technology, as those skilled in the relevant art will recognize. For example, while steps are presented in a given order, alternative embodiments may perform steps in a different order. The various embodiments described herein may also be combined to provide further embodiments.

Moreover, unless the word "or" is expressly limited to mean only a single item exclusive from the other items in reference to a list of two or more items, then the use of "or" in such a list is to be interpreted as including (a) any single item in the list, (b) all of the items in the list, or (c) any combination of the items in the list. Additionally, the term "comprising" is used throughout to mean including at least the recited feature(s) such that any greater number of the same feature and/or additional types of other features are not precluded. It will also be appreciated that specific embodiments have been described herein for purposes of illustration, but that various modifications may be made without deviating from the technology. Further, while advantages associated with certain embodiments of the technology have been described in the context of those embodiments, other embodiments may also exhibit such advantages, and not all embodiments need necessarily exhibit such advantages to fall within the scope of the technology. Accordingly, the disclosure and associated technology can encompass other embodiments not expressly shown or described herein.

REFERENCES

The references, patents, and published patent applications listed below, and all references cited in the specification above are hereby incorporated by reference in their entirety, as if fully set forth herein.

[1] Brown R D Jr, Broderick J P. Unruptured intracranial aneurysms: epidemiology, natural history, management options, and familial screening. Lancet Neurol 2014; 13:393-404.

[2] Bor A S, Rinkel G J, van Norden J, Wermer M J. Long-term, serial screening for intracranial aneurysms in individuals with a family history of aneurysmal subarachnoid haemorrhage: a cohort study. Lancet Neurol 2014; 13:385-392.

[3] Guglielmi G, Viñuela F, Duckwiler G, Dion J, Lylyk P, Berenstein A, et al. Endovascular treatment of posterior circulation aneurysms by electrothrombosis using electrically detachable coils. J Neurosurg 1992; 77:515-524.

[4] Molyneux A, Kerr R, Stratton I, Sandercock P, Clarke M, Shrimpton J, et al. International Subarachnoid Aneurysm Trial (ISAT) of neurosurgical clipping versus endovascular coiling in 2143 patients with ruptured intracranial aneurysms: a randomised trial. Lancet 2002; 360:1267-1274.

[5] Molyneux A J, Kerr R S, Yu L M, Clarke M, Sneade M, Yarnold J A, et al. International subarachnoid aneurysm trial (ISAT) of neurosurgical clipping versus endovascular coiling in 2143 patients with ruptured intracranial aneurysms: a randomised comparison of effects on survival, dependency, seizures, rebleeding, subgroups, and aneurysm occlusion. Lancet 2005; 366:809-817.

[6] Wiebers D O, Whisnant J P, Huston J 3rd, Meissner I, Brown R D Jr, Piepgras D G, et al. Unruptured intracranial aneurysms: natural history, clinical outcome, and risks of surgical and endovascular treatment. Lancet 2003; 362:103-110.

We claim:

1. An occlusive device for treating an aneurysm, wherein a neck of the aneurysm opens to a blood vessel, the device comprising:
    a mesh having a low-profile state for intravascular delivery to the aneurysm and a deployed state, the mesh comprising—
        a first end portion, a second end portion, and a length extending between the first and second end portions,
        a first lateral edge, a second lateral edge, and a width extending between the first and second lateral edges, and
        a first side, a second side opposite the first side, and a thickness extending therebetween, and
    wherein, in the deployed state, the mesh has a first surface at the first side and a second surface at the second side,
        the first surface is bound between opposing first longitudinal ends and opposing first side edges, the first surface having a first length between the first longitudinal ends and a first width between the first side edges, wherein the first surface has a first convex region and a first concave region; and
        the second surface is bound between opposing second longitudinal ends and opposing second side edges, the second surface having a second length between the second longitudinal ends and a second width between the second side edges, wherein the second surface has a second convex region and a second concave region, and wherein the mesh is configured to be positioned within the aneurysm in the deployed state such that the mesh extends over the neck of the aneurysm.

2. The device of claim 1, wherein the first concave region is surrounded by the first convex region.

3. The device of claim 1, wherein the second convex region is surrounded by the second concave region.

4. The device of claim 1, wherein:
the first concave region is surrounded by the first convex region, and
the second convex region is surrounded by the second concave region.

5. The device of claim 1, wherein the mesh is a flattened tubular braid.

6. The device of claim 1, wherein the first convex region has a radius of curvature that increases continuously along the first length.

7. The device of claim 1, wherein the second concave region has a radius of curvature that increases continuously along the second length.

8. The device of claim 1, wherein a radius of curvature of the first convex region is greater than a radius of curvature of the first concave region.

9. The device of claim 1, wherein a radius of curvature of the second convex region is less than a radius of curvature of the second concave region.

10. The device of claim 1, wherein the first concave region and the second convex region correspond to a longitudinal divot extending along at least a portion of the length of the mesh.

11. The device of claim 1, wherein the mesh comprises a first layer and a second layer that meet at the first and second lateral edges.

12. The device of claim 1, wherein the mesh has a generally constant thickness along its length.

13. An occlusive device for treating an aneurysm, wherein a neck of the aneurysm opens to a blood vessel, the device comprising:
a mesh having a low-profile state for intravascular delivery to the aneurysm and a deployed state, the mesh comprising—
a first end portion, a second end portion, and a length extending between the first and second end portions, and
a first lateral edge, a second lateral edge, and a width extending between the first and second lateral edges; a first side, a second side opposite the first side, and a thickness therebetween; and
an elongated embolic element coupled to the mesh;
wherein the mesh has a predetermined shape in the deployed state in which (a) the mesh is curved along its width, (b) the mesh is curved along its length, and (c) the mesh has a first region, a second region, and a third region extending along its width such that the first region is closest to the first lateral edge and the third region is closest to the second lateral edge, the second region being disposed between the first and third regions, and
wherein, wherein the mesh is in an expanded, unconstrained configuration, the first and third regions of the mesh are concave towards the first side and the second region of the mesh is convex towards the first side,
wherein the occlusive device is configured to be positioned within the aneurysm such that the mesh extends over the neck of the aneurysm and the elongated embolic element is positioned between a dome of the aneurysm and the mesh.

14. The occlusive device of claim 13, wherein the occlusive device is configured to be positioned in the aneurysm in a deployed state such that the first side of the mesh faces a dome of the aneurysm and a second side of the mesh faces the neck of the aneurysm.

15. The occlusive device of claim 13, wherein the mesh and the embolic element are coupled end-to-end.

16. The occlusive device of claim 13, wherein the mesh and the embolic element are coupled end-to-end and such that, when positioned within a delivery catheter for intravascular delivery to the aneurysm, the mesh is distal of the embolic element in the delivery catheter so that the mesh is delivered to the aneurysm before the embolic element.

17. The occlusive device of claim 13, wherein the embolic element is a coil.

18. The occlusive device of claim 13, wherein the embolic element and the mesh are coupled at a joint, and wherein the embolic element and the mesh are configured to bend and twist relative to one another at the joint.

19. The occlusive device of claim 18, wherein the first end portion of the mesh includes a band, and wherein an end portion of the embolic element is positioned over at least a portion of the band at the joint.

20. The occlusive device of claim 13, wherein the mesh is formed of a flattened tubular braid.

\* \* \* \* \*

UNITED STATES PATENT AND TRADEMARK OFFICE
CERTIFICATE OF CORRECTION

PATENT NO. : 11,129,621 B2
APPLICATION NO. : 16/718165
DATED : September 28, 2021
INVENTOR(S) : Hamel et al.

Page 1 of 1

It is certified that error appears in the above-identified patent and that said Letters Patent is hereby corrected as shown below:

On the Title Page

Item (56), in Column 2, under "Other Publications", Line 1, delete "Endovascular" and insert -- Endosaccular --, therefor.

Signed and Sealed this
Twenty-eighth Day of December, 2021

Drew Hirshfeld
*Performing the Functions and Duties of the*
*Under Secretary of Commerce for Intellectual Property and*
*Director of the United States Patent and Trademark Office*